(12) United States Patent
Yamamoto

(10) Patent No.: US 10,942,134 B2
(45) Date of Patent: Mar. 9, 2021

(54) MEASUREMENT DEVICE, METHOD OF OPERATING MEASUREMENT DEVICE, AND RECORDING MEDIUM

(71) Applicant: OLYMPUS CORPORATION, Tokyo (JP)

(72) Inventor: Naoki Yamamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 232 days.

(21) Appl. No.: 16/137,613

(22) Filed: Sep. 21, 2018

(65) Prior Publication Data

US 2019/0094153 A1  Mar. 28, 2019

(30) Foreign Application Priority Data

Sep. 26, 2017 (JP) ................. 2017-185006

(51) Int. Cl.
| | |
|---|---|
| *G01N 21/93* | (2006.01) |
| *G06K 9/46* | (2006.01) |
| *G01B 11/24* | (2006.01) |
| *A61B 1/07* | (2006.01) |
| *G02B 23/24* | (2006.01) |
| *A61B 5/107* | (2006.01) |

(Continued)

(52) U.S. Cl.
CPC ......... *G01N 21/93* (2013.01); *A61B 1/00009* (2013.01); *A61B 1/07* (2013.01);
(Continued)

(58) Field of Classification Search
CPC ........ A61B 2562/0219; A61B 1/00009; A61B 1/07; A61B 5/1076; A61B 5/1112;
(Continued)

(56) References Cited

U.S. PATENT DOCUMENTS 9,492,059 B2 * 11/2016 Sasaki ................ A61B 1/00009
9,672,608 B2 *  6/2017 Hamada ............. H04N 5/23254
(Continued)

FOREIGN PATENT DOCUMENTS

| | | |
|---|---|---|
| JP | 2001-153617 A | 6/2001 |
| JP | 2006-058311 A | 3/2006 |

(Continued)

OTHER PUBLICATIONS

Notice of Allowance dated Nov. 4, 2020 received in Japanese Patent Application No. 2017-185006.

*Primary Examiner* — Elias Desta
(74) *Attorney, Agent, or Firm* — Scully, Scott, Murphy & Presser, P.C.

(57) ABSTRACT

A reference designation point setting unit sets a plurality of reference designation points. A reference calculation unit calculates one of a reference line and a reference plane used in a measurement mode indicated by measurement mode information, on the basis of the plurality of reference designation points. A measurement point setting unit sets a measurement point. A reference point calculation unit calculates a plurality of reference points leading to higher reliability of a measurement result instead of a plurality of reference designation points, on the basis of the image in which the measurement point is set, the plurality of reference designation points, the measurement mode, and the measurement point. The reference calculation unit calculates one of a new reference line and a new reference plane on the basis of the plurality of reference points.

20 Claims, 41 Drawing Sheets

(51) Int. Cl.
*A61B 1/00* (2006.01)
*G01N 21/954* (2006.01)
*G01N 21/88* (2006.01)

(52) U.S. Cl.
CPC ............ *A61B 5/1076* (2013.01); *G01B 11/24* (2013.01); *G02B 23/24* (2013.01); *G06K 9/4604* (2013.01); *G01N 21/8851* (2013.01); *G01N 21/954* (2013.01)

(58) Field of Classification Search
CPC ........ A61B 5/1118; A61B 5/74; G06N 20/00; G01B 11/24; G02B 23/24; G06K 9/4604; G01N 21/8851; G01N 21/954
See application file for complete search history.

(56) References Cited

U.S. PATENT DOCUMENTS 10,508,902 B2 * 12/2019 Tabuchi ................ G01B 21/04
2010/0145650 A1   6/2010 Nahum et al.

FOREIGN PATENT DOCUMENTS

| JP | 2006-329684 A | 12/2006 |
| JP | 2007-212268 A | 8/2007 |
| JP | 2010-256247 A | 11/2010 |
| JP | 5530225 B2 | 6/2014 |
| JP | 2014-140402 A | 8/2014 |
| JP | 2016-080674 A | 5/2016 |

* cited by examiner

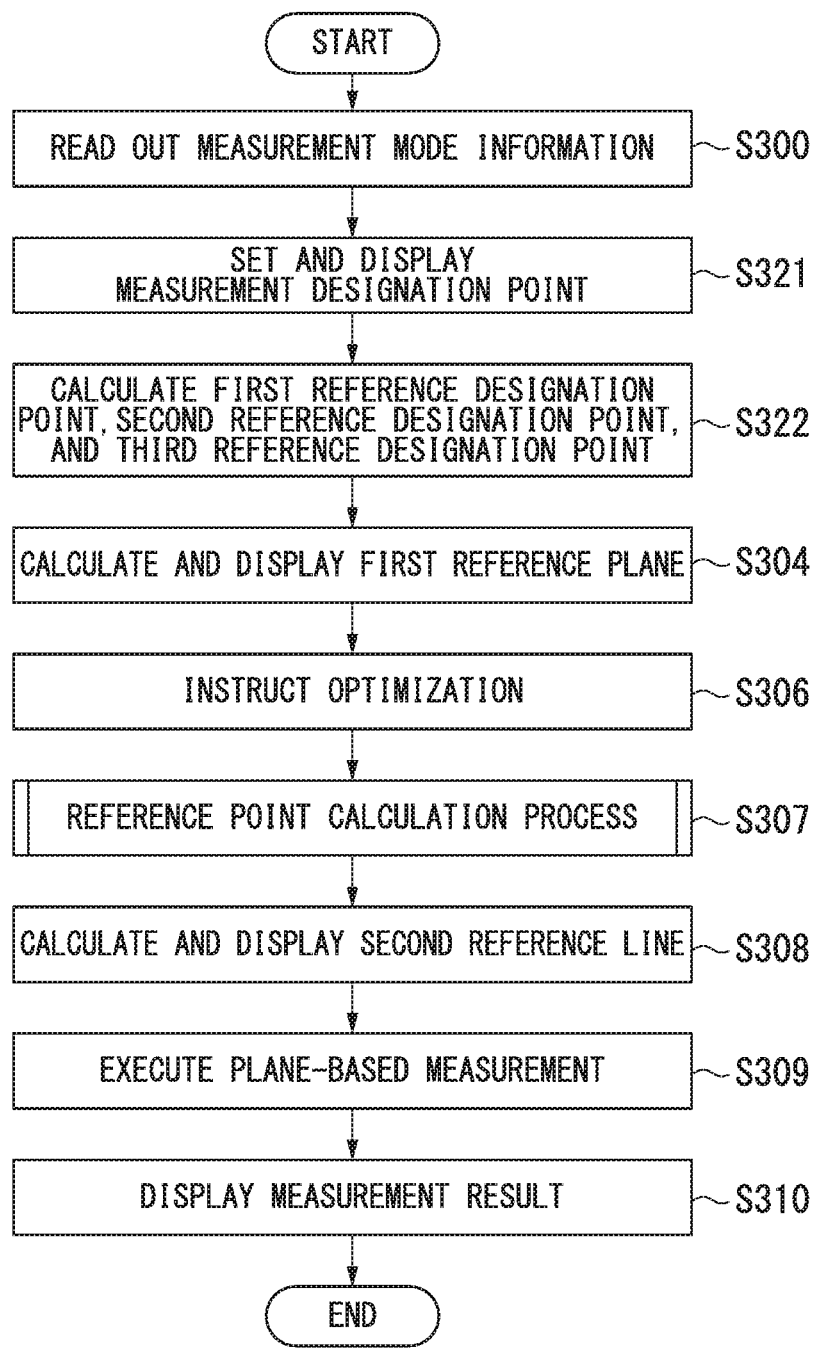

MEASUREMENT DEVICE, METHOD OF OPERATING MEASUREMENT DEVICE, AND RECORDING MEDIUM

BACKGROUND OF THE INVENTION

Field of the Invention

The present invention relates to a measurement device, a method of operating a measurement device, and a recording medium.

Priority is claimed on Japanese Patent Application No. 2017-185006, filed on Sep. 26, 2017, the content of which is incorporated herein by reference

Description of Related Art

Industrial endoscope devices have been used in the observation and inspection of internal damage and corrosion of boilers, pipes and the like. In such an endoscope device, multiple types of optical adaptors for observing and inspecting various substances to be observed are prepared. The optical adaptor is mounted on the tip portion of an endoscope, and can be replaced. In inspection using such an endoscope device, there is a desire to quantitatively measure the size of the defect and damage of a subject. To meet such a desire, an endoscope device provided with a three-dimensional measurement function is present.

For example, an endoscope device is provided with a function of measuring geometric dimensions on the basis of information of a point designated on an image by a user. For example, in distance measurement between two points, a three-dimensional distance between two measurement points designated by a user is measured. In line-based measurement, a reference line is set on the basis of two reference points designated by a user, and a three-dimensional distance from a measurement point designated by a user to the reference line is measured. In plane-based measurement, a reference plane is set on the basis of three reference points designated by a user, and a three-dimensional distance from a measurement point designated by a user to the reference plane is measured.

There are two problems in the designation of the measurement point and the reference point. A first problem is that it is troublesome for a user to accurately designate the measurement point and the reference point. A second problem is that the positions of the measurement point and the reference point at which more accurate measurement results are obtained are not easily perceived by a user.

A measurement endoscope device disclosed in Japanese Unexamined Patent Application, First Publication No. 2006-329684 extracts a plurality of feature points, and presents the extracted feature points to a user. In addition, the measurement endoscope device causes the user to select one or more feature points from the presented feature points. Thereby, the measurement endoscope device makes it possible to reduce the time and effort of an operation when the user designates a measurement point.

An endoscope device disclosed in Japanese Patent No. 5530225 automatically sets three reference points on the circumference of a circle centering on one measurement point designated by a user. After the user designates the measurement point, a circle centering on the measurement point and passing through the position of a cursor is displayed. The user can change the positions of the three reference points by moving the cursor on an image. The user designates the three reference points by performing an operation such as a click. The user performs an operation such as a click when designating the measurement point and when designating the three reference points. In a case where the user designates four points one by one, four operations are required. On the other hand, in the endoscope device disclosed in Japanese Patent No. 5530225, the number of times of the user's operation may be just two. Thereby, the endoscope device makes it possible to reduce the time and effort of the user's operation in plane-based measurement.

A device disclosed in Japanese Unexamined Patent Application, First Publication No. 2016-80674 automatically sets a measurement point within a region surrounded by a reference line which is set on the basis of three reference points designated by a user. The measurement point is set at a position where a distance from a reference plane based on the three reference points is largest. Thereby, the device makes it possible to reduce the time and effort of the user's operation in plane-based measurement.

FIGS. 41A and 41B show an example of a measurement point and reference points in line-based measurement. An image G11 shown in FIGS. 41A and 41B includes images of a subject OB11 and a subject OB12. A first reference point P901, a second reference point P902, and a measurement point P903 are set on the edge of the subject OB11 which is a characteristic place. In FIGS. 41A and 41B, a reference line L901 based on the first reference point P901 and the second reference point P902 is shown. In addition, in FIGS. 41A and 41B, an auxiliary line L902 based on the measurement point P903 and the reference line L901 is shown.

The error of a reference line has a tendency to increase as a distance between two reference points decreases. Therefore, it is preferable that a distance between two reference points is large. A distance between the first reference point P901 and the second reference point P902 in FIG. 41B is larger than a distance between the first reference point P901 and the second reference point P902 in FIG. 41A. From this viewpoint, in FIG. 41B, the reliability of a measurement result is higher than in FIG. 41A.

The error of a reference line is small between two reference points. In a case where an intersection point of a perpendicular line from a measurement point to a reference line with the reference line is not located between two reference points, the error of a reference line at the intersection point has a tendency to increase. Therefore, it is preferable that the intersection point is located between two reference points. The intersection point of a perpendicular line from the measurement point to the reference line with the reference line is a point closest to the measurement point on the reference line. In FIG. 41A, an intersection point P904 of a perpendicular line from the measurement point P903 to the reference line L901 with the reference line L901 is not located between the first reference point P901 and the second reference point P902. In FIG. 41B, the intersection point P904 of a perpendicular line from the measurement point P903 to the reference line L901 with the reference line L901 is located between the first reference point P901 and the second reference point P902. Therefore, from this viewpoint, in FIG. 41B, the reliability of a measurement result is also higher than in FIG. 41A.

Appropriate measurement points and reference points differ from each other depending on a measurement mode. It is necessary for a user to determine appropriate measurement points and reference points on the basis of a determination criterion for each measurement mode.

SUMMARY OF THE INVENTION

According to a first aspect of the present invention, a measurement device includes an image acquisition unit, a display control unit, an information reading unit, a reference designation point setting unit, a reference calculation unit, a measurement point setting unit, a measurement unit, and a reference point calculation unit. The image acquisition unit acquires a first image of a subject. The display control unit causes a monitor to display at least one of the first image and a second image based on the first image. The information reading unit reads out measurement mode information indicating a measurement mode from a recording medium having the measurement mode information recorded therein. The reference designation point setting unit sets a plurality of reference designation points in one of the first image and the second image displayed on the monitor, on the basis of a first position designated by a user in one of the first image and the second image displayed on the monitor. The reference calculation unit calculates one of a reference line and a reference plane on the basis of the plurality of reference designation points. The reference line and the reference plane are used in the measurement mode indicated by the measurement mode information. The measurement point setting unit sets a measurement point in one of the first image and the second image displayed on the monitor, on the basis of a second position designated by the user in one of the first image and the second image displayed on the monitor. The measurement unit executes measurement of the subject. The reference point calculation unit calculates a plurality of reference points leading to higher reliability of a measurement result instead of the plurality of reference designation points, on the basis of one of the first image and the second image in which the measurement point is set, the plurality of reference designation points, the measurement mode, and the measurement point. The reference calculation unit calculates one of a new reference line and a new reference plane on the basis of the plurality of reference points. The measurement unit executes the measurement on the basis of one of the new reference line and the new reference plane, the measurement point, and the measurement mode.

According to a second aspect of the present invention, in the first aspect, the reference point calculation unit may calculate a portion of the plurality of reference points using a point, located at the same position as that of the reference designation point included in the plurality of reference designation points, as the reference point.

According to a third aspect of the present invention, in the first or second aspect, the reference point calculation unit may calculate the plurality of reference points such that distances between the plurality of reference points increase.

According to a fourth aspect of the present invention, in the first or second aspect, the plurality of reference points may be at least three reference points. The reference point calculation unit may calculate the at least three reference points such that an area of a polygon with vertices at the at least three reference points increases.

According to a fifth aspect of the present invention, in the first or second aspect, the reference point calculation unit may calculate the plurality of reference points such that one of a first intersection point and a second intersection point comes close to a centroid of the plurality of reference points. The first intersection point may be an intersection point of a perpendicular line from the measurement point to the new reference line with the new reference line. The second intersection point may be an intersection point of a perpendicular line from the measurement point to the new reference plane with the new reference plane.

According to a sixth aspect of the present invention, in the first or second aspect, the reference point calculation unit may calculate the plurality of reference points such that a degree to which the new reference line approximates an end of the subject becomes higher.

According to a seventh aspect of the present invention, in the first or second aspect, the reference point calculation unit may calculate the plurality of reference points such that a degree to which the new reference plane approximates a surface of the subject becomes higher.

According to an eighth aspect of the present invention, in the first or second aspect, the reference point calculation unit may calculate at least one reference point included in the plurality of reference points such that distances between the plurality of reference points become larger than distances between the plurality of reference designation points.

According to a ninth aspect of the present invention, in the first or second aspect, the plurality of reference designation points may be at least three reference designation points. The plurality of reference points may be at least three reference points. The reference point calculation unit may calculate the at least three reference points such that a first area becomes larger than a second area. The first area may be an area of a polygon with vertices at the at least three reference points. The second area may be an area of a polygon with vertices at the at least three reference designation points.

According to a tenth aspect of the present invention, in the first or second aspect, the reference point calculation unit may calculate the plurality of reference points such that a first distance becomes smaller than a second distance. The first distance may be a distance between one of a first intersection point and a second intersection point and a centroid of the plurality of reference points. The first intersection point may be an intersection point of a perpendicular line from the measurement point to the new reference line with the new reference line. The second intersection point may be an intersection point of a perpendicular line from the measurement point to the new reference plane with the new reference plane. The second distance may be a distance between one of a third intersection point and a fourth intersection point and a centroid of the plurality of reference designation points. The third intersection point may be an intersection point of a perpendicular line from the measurement point to the reference line with the reference line. The fourth intersection point may be an intersection point of a perpendicular line from the measurement point to the reference plane with the reference plane.

According to an eleventh aspect of the present invention, in the first or second aspect, the reference point calculation unit may calculate the plurality of reference points such that a first degree becomes higher than a second degree. The first degree may be a degree to which one of the new reference line and the new reference plane determined on the basis of the plurality of reference points approximates a surface of the subject. The second degree may be a degree to which one of the reference line and the reference plane determined on the basis of the plurality of reference designation points approximates the surface of the subject.

According to a twelfth aspect of the present invention, in the first or second aspect, the reference point calculation unit may calculate at least one reference point included in the plurality of reference points such that a position of the at least one reference point satisfies a criterion according to characteristics of the measurement mode indicated by the measurement mode information.

According to a thirteenth aspect of the present invention, in the twelfth aspect, the reference point calculation unit may set a plurality of temporary reference points in one of the first image and the second image displayed on the monitor. The reference point calculation unit may select combinations, each including at least two temporary reference points included in the plurality of temporary reference points. The reference point calculation unit may calculate an evaluation value indicating a degree to which the at least two temporary reference points included in the combination are suitable for the criterion, for each combination. In a case where a first degree indicated by the evaluation value of a first combination is higher than a second degree indicated by the evaluation value of a second combination, the reference point calculation unit may set at least one of the at least two temporary reference points included in the first combination as the reference point.

According to a fourteenth aspect of the present invention, in the first or second aspect, the display control unit may cause the monitor to display the plurality of reference points on at least one of the first image and the second image.

According to a fifteenth aspect of the present invention, in the first or second aspect, the display control unit may cause the monitor to display one of the reference line and the reference plane determined on the basis of the plurality of reference points on at least one of the first image and the second image.

According to a sixteenth aspect of the present invention, in the first or second aspect, the display control unit may cause the monitor to display the plurality of reference points and the plurality of reference designation points on at least one of the first image and the second image.

According to a seventeenth aspect of the present invention, in the first or second aspect, the display control unit may cause the monitor to display the new reference line determined on the basis of the plurality of reference points and the reference line determined on the basis of the plurality of reference designation points on at least one of the first image and the second image.

According to an eighteenth aspect of the present invention, in the first or second aspect, the display control unit may cause the monitor to display the new reference plane determined on the basis of the plurality of reference points and the reference plane determined on the basis of the plurality of reference designation points on at least one of the first image and the second image.

According to a nineteenth aspect of the present invention, a method of operating a measurement device includes an image acquisition step, a display step, an information reading step, a reference designation point setting step, a first reference calculation step, a measurement point setting step, a reference point calculation step, a second reference calculation step, and a measurement step. In the image acquisition step, an image acquisition unit acquires a first image of a subject. In the display step, a display control unit causes a monitor to display at least one of the first image and a second image based on the first image. In the information reading step, an information reading unit reads out measurement mode information indicating a measurement mode from a recording medium having the measurement mode information recorded therein. In the reference designation point setting step, a reference designation point setting unit sets a plurality of reference designation points in one of the first image and the second image displayed on the monitor, on the basis of a first position designated by a user in one of the first image and the second image displayed on the monitor. In the first reference calculation step, a reference calculation unit calculates one of a reference line and a reference plane on the basis of the plurality of reference designation points. The reference line and the reference plane are used in the measurement mode indicated by the measurement mode information. In the measurement point setting step, a measurement point setting unit sets a measurement point in one of the first image and the second image displayed on the monitor, on the basis of a second position designated by the user in one of the first image and the second image displayed on the monitor. In the reference point calculation step, a reference point calculation unit calculates a plurality of reference points leading to higher reliability of a measurement result instead of the plurality of reference designation points, on the basis of one of the first image and the second image in which the measurement point is set, the plurality of reference designation points, the measurement mode, and the measurement point. In the second reference calculation step, the reference calculation unit calculates one of a new reference line and a new reference plane on the basis of the plurality of reference points. In the measurement step, a measurement unit executes measurement of the subject on the basis of one of the new reference line and the new reference plane, the measurement point, and the measurement mode.

According to a twentieth aspect of the present invention, a computer-readable non-transitory recording medium saves a program for causing a computer to execute an image acquisition step, a display step, an information reading step, a reference designation point setting step, a first reference calculation step, a measurement point setting step, a reference point calculation step, a second reference calculation step, and a measurement step. In the image acquisition step, the computer acquires a first image of a subject. In the display step, the computer causes a monitor to display at least one of the first image and a second image based on the first image. In the information reading step, the computer reads out measurement mode information indicating a measurement mode from a recording medium having the measurement mode information recorded therein. In the reference designation point setting step, the computer sets a plurality of reference designation points in one of the first image and the second image displayed on the monitor, on the basis of a first position designated by a user in one of the first image and the second image displayed on the monitor. In the first reference calculation step, the computer calculates one of a reference line and a reference plane on the basis of the plurality of reference designation points. The reference line and the reference plane being used in the measurement mode indicated by the measurement mode information. In the measurement point setting step, the computer sets a measurement point in one of the first image and the second image displayed on the monitor, on the basis of a second position designated by the user in one of the first image and the second image displayed on the monitor. In the reference point calculation step, the computer calculates a plurality of reference points leading to higher reliability of a measurement result instead of the plurality of reference designation points, on the basis of one of the first image and the second image in which the measurement point is set, the plurality of reference designation points, the measurement mode, and the measurement point. In the second reference calculation step, the computer calculates one of a new reference line and a new reference plane on the basis of the plurality of reference points. In the measurement step, the computer executes measurement of the subject on the basis of one of the new reference line and the new reference plane, the measurement point, and the measurement mode.

BRIEF DESCRIPTION OF THE DRAWINGS

FIG. 26 is a flow diagram showing a procedure of three-dimensional measurement in a sixth embodiment of the present invention.

DETAILED DESCRIPTION OF THE INVENTION

Hereinafter, embodiments of the present invention will be described with reference to the drawings. In the following, an example in which a measurement device is an endoscope device will be described. The measurement device is not limited to an endoscope device insofar as being a device having a measurement function. Each unit constituting the endoscope device and other devices may be connected to each other either using wires or wirelessly.

First Embodiment

Figure 1:
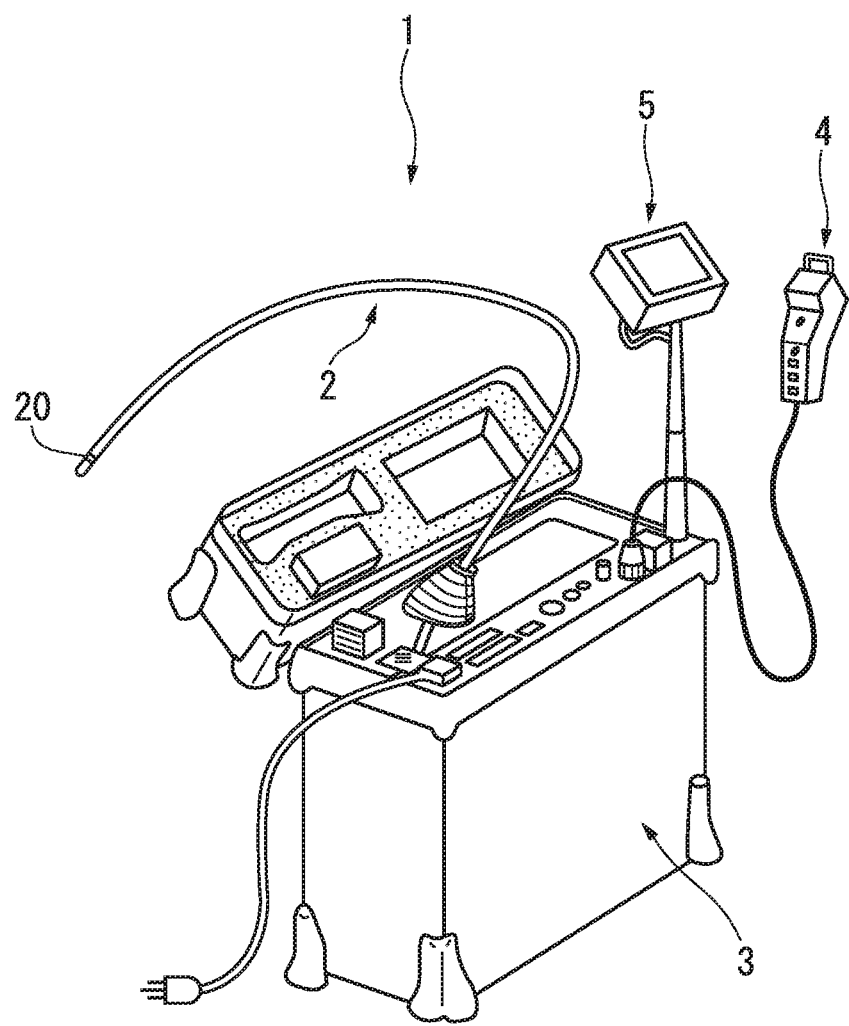
FIG. 1 is a perspective view showing an entire configuration of an endoscope device according to a first embodiment of the present invention.

FIG. 1 shows the outer appearance of an endoscope device 1 (measurement device) according to a first embodiment of the present invention. The endoscope device 1 captures an optical image of a subject, and measures geometric features of the subject on the basis of the image. An inspector can perform the replacement of an optical adaptor mounted on the tip of an insertion portion 2, the selection of a built-in measurement processing program, and the addition of a measurement processing program, in order to observe and measure various subjects.

As shown in FIG. 1, the endoscope device 1 includes the insertion portion 2, a main body unit 3, an operation unit 4, and a display unit 5.

The insertion portion 2 is inserted into a subject. The insertion portion 2 has an elongated tubular shape bendable from a tip 20 across a base end. The insertion portion 2 captures an optical image of a measurement portion, and outputs an imaging signal to the main body unit 3. An optical adaptor is to be mounted on the tip 20 of the insertion portion 2. The main body unit 3 is a control device including a housing unit that houses the insertion portion 2. The operation unit 4 receives a user's operation on the endoscope device 1. The display unit 5 has a display screen, and displays an image of a subject captured by the insertion portion 2, an operation menu and the like on the display screen.

The operation unit 4 is a user interface. For example, the user interface is at least one of a button, a switch, a key, a mouse, a joystick, a touch pad, a trackball, and a touch panel. The display unit 5 is a monitor (display) such as a liquid crystal display (LCD). The display unit 5 may be a touch panel. In that case, the operation unit 4 and the display unit 5 are formed integrally with each other.

Figure 2:
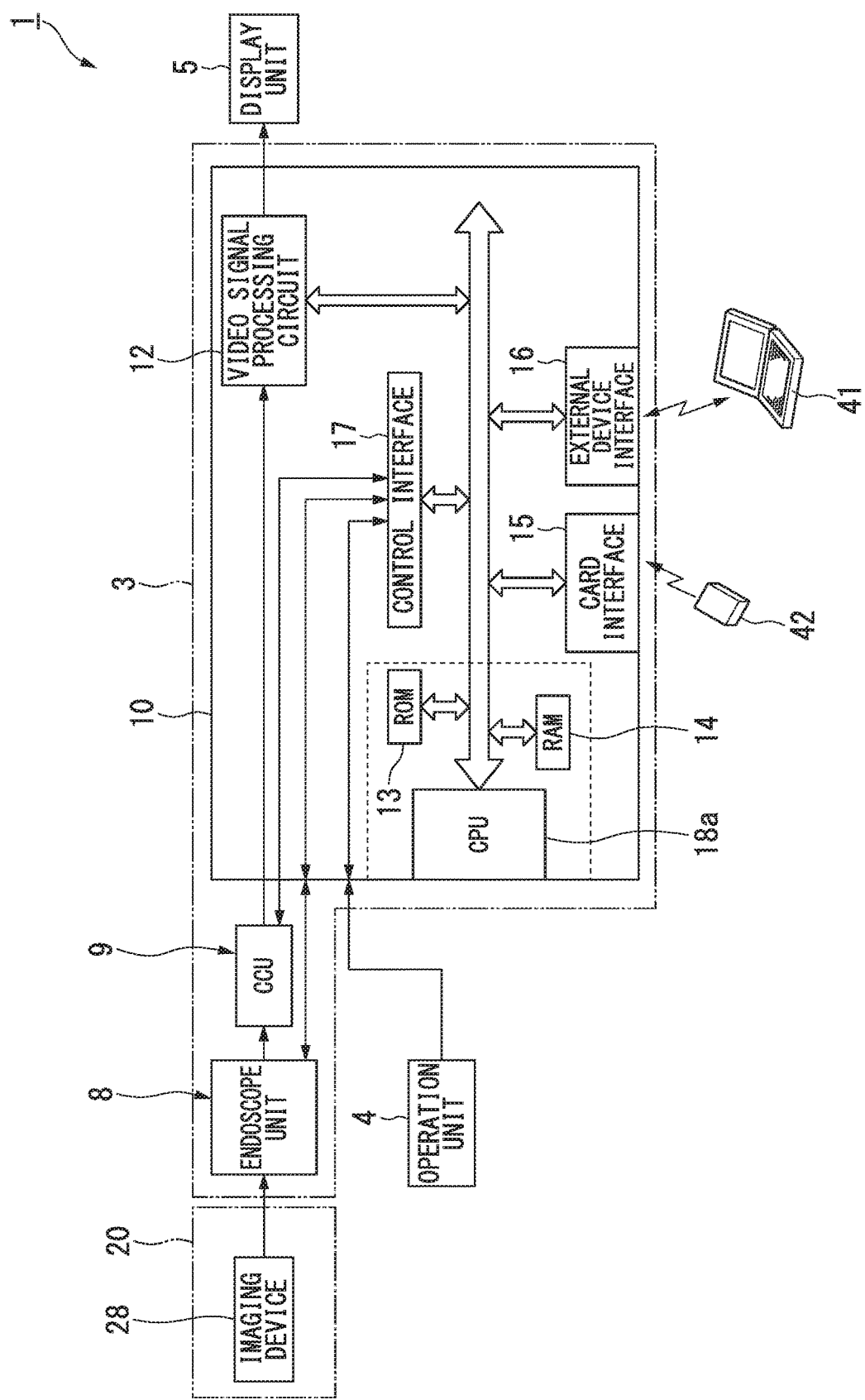
FIG. 2 is a block diagram showing an internal configuration of the endoscope device according to the first embodiment of the present invention.

As shown in FIG. 2, the main body unit 3 includes an endoscope unit 8, a camera control unit (CCU) 9, and a control device 10. The endoscope unit 8 includes a light source device and a bending device which are not shown in the drawing. The light source device supplies illumination light necessary for observation. The bending device bends a bending mechanism which is not shown in the drawing. An imaging device 28 is built into the tip 20 of the insertion portion 2. The imaging device 28 is an image sensor. The imaging device 28 photoelectrically converts a subject image formed through the optical adaptor, and generates an imaging signal. The CCU 9 drives the imaging device 28. The imaging signal output from the imaging device 28 is input to the CCU 9. The CCU 9 performs preprocessing including amplification, noise removal and the like on the imaging signal acquired by the imaging device 28. The CCU 9 converts the imaging signal on which the preprocessing has been performed into a video signal such as an NTSC signal.

The control device 10 includes a video signal processing circuit 12, a read only memory (ROM) 13, a random access memory (RAM) 14, a card interface 15, an external device interface 16, a control interface 17, and a central processing unit (CPU) 18a.

The video signal processing circuit 12 performs predetermined video processing on the video signal output from the CCU 9. For example, the video signal processing circuit 12 performs video processing related to improvement in visibility. For example, the video processing is color reproduction, gradation correction, noise suppression, contour enhancement, and the like. The video signal processing circuit 12 also performs a process for improving measurement performance during measurement execution. In addition, the video signal processing circuit 12 combines the video signal output from the CCU 9 and a graphic image signal generated by the CPU 18a. The graphic image signal includes an image of an operation screen, measurement information, and the like. The measurement information includes an image of a cursor, an image of a designation point, a measurement result, and the like. The video signal processing circuit 12 outputs the combined video signal to the display unit 5.

The ROM 13 is a non-volatile recording medium in which a program with which the CPU 18a controls the operation of the endoscope device 1 is recorded. The RAM 14 is a volatile recording medium that temporarily stores information used by the CPU 18a to control the endoscope device 1. The CPU 18a controls the operation of the endoscope device 1 on the basis of the program recorded in the ROM 13.

A memory card 42 which is a removable recording medium is connected to the card interface 15. The card interface 15 inputs control processing information, image information and the like stored in the memory card 42 to the control device 10. In addition, the card interface 15 records the control processing information, the image information and the like generated by the endoscope device 1 in the memory card 42.

An external device such as a USB device is connected to the external device interface 16. For example, a personal computer 41 is connected to the external device interface 16. The external device interface 16 transmits information to the personal computer 41 and receives information from the personal computer 41. Thereby, the monitor of the personal computer 41 can display information. In addition, a user can perform an operation related to control of the endoscope device 1 through the personal computer 41.

The control interface 17 performs communication for operation control with the operation unit 4, the endoscope unit 8, and the CCU 9. The control interface 17 notifies the CPU 18a of an instruction input by a user through the operation unit 4. The control interface 17 outputs control signals for controlling the light source device and the bending device to the endoscope unit 8. The control interface 17 outputs a control signal for controlling the imaging device 28 to the CCU 9.

A program executed by the CPU 18a may be recorded in a computer-readable recording medium. A computer other than the endoscope device 1 may read and execute the program recorded in this recording medium. For example, the personal computer 41 may read and execute the program. The personal computer 41 may control the endoscope device 1 by transmitting control information for controlling the endoscope device 1 to the endoscope device 1 in accordance with the program. Alternatively, the personal computer 41 may acquire a video signal from the endoscope device 1, and perform measurement using the acquired video signal.

The above-mentioned program may be transmitted from a computer having a storage device or the like in which this program is stored through a transmission medium or through transmitted waves in the transmission medium to the endoscope device 1. The "transmission medium" that transmits a program refers to a medium having a function of transmitting information like networks (communication networks) such as the Internet or communication channels (communication lines) such as a telephone line. In addition, the above-mentioned program may realize a portion of the above-mentioned functions. Further, the above-mentioned program may be a difference file (difference program) capable of realizing the above-mentioned functions in combination with a program which is already recorded in a computer.

As described above, the endoscope device 1 includes the imaging device 28 (imaging unit), the CCU 9 (image acquisition unit), and the CPU 18a. The imaging device 28 captures an optical image of a subject which is an object to be measured, and generates an imaging signal. Thereby, the imaging device 28 generates an image (first image) of the subject. The CCU 9 generates a video signal (image data) on the basis of the imaging signal. The video signal includes the image of the subject. Therefore, the CCU 9 acquires the image of the subject generated by capturing the image of the subject. The image acquired by the CCU 9 is input to the CPU 18a.

The endoscope device 1 according to the first embodiment has a line-based measurement function. In the first embodiment, two reference designation points and one measurement designation point are designated by a user. The reference designation point indicates a position designated as the reference point by a user. The measurement designation point indicates a position designated as a measurement point by a user. Two reference points at which a measurement result having high reliability is obtained are calculated on the basis of the two reference designation points. The reference point indicates a reference position for calculating a reference line in line-based measurement and a reference plane in plane-based measurement. A measurement point is set at the position of the measurement designation point. The measurement point indicates a position at which the dimensions of a subject are measured.

For example, the endoscope device 1 performs stereo measurement. In the stereo measurement, the measurement of a subject is performed on the principle of triangulation on the basis of two subject images corresponding to a plurality of viewpoints different from each other. A measurement scheme applied to the endoscope device 1 is not limited to the stereo measurement. For example, the endoscope device 1 may perform measurement based on a phase shift method using an image of a subject on which a plurality of stripe patterns having different spatial phases are projected. Alternatively, the endoscope device 1 may perform measurement using an image of a subject on which a random pattern is projected.

Figure 3:
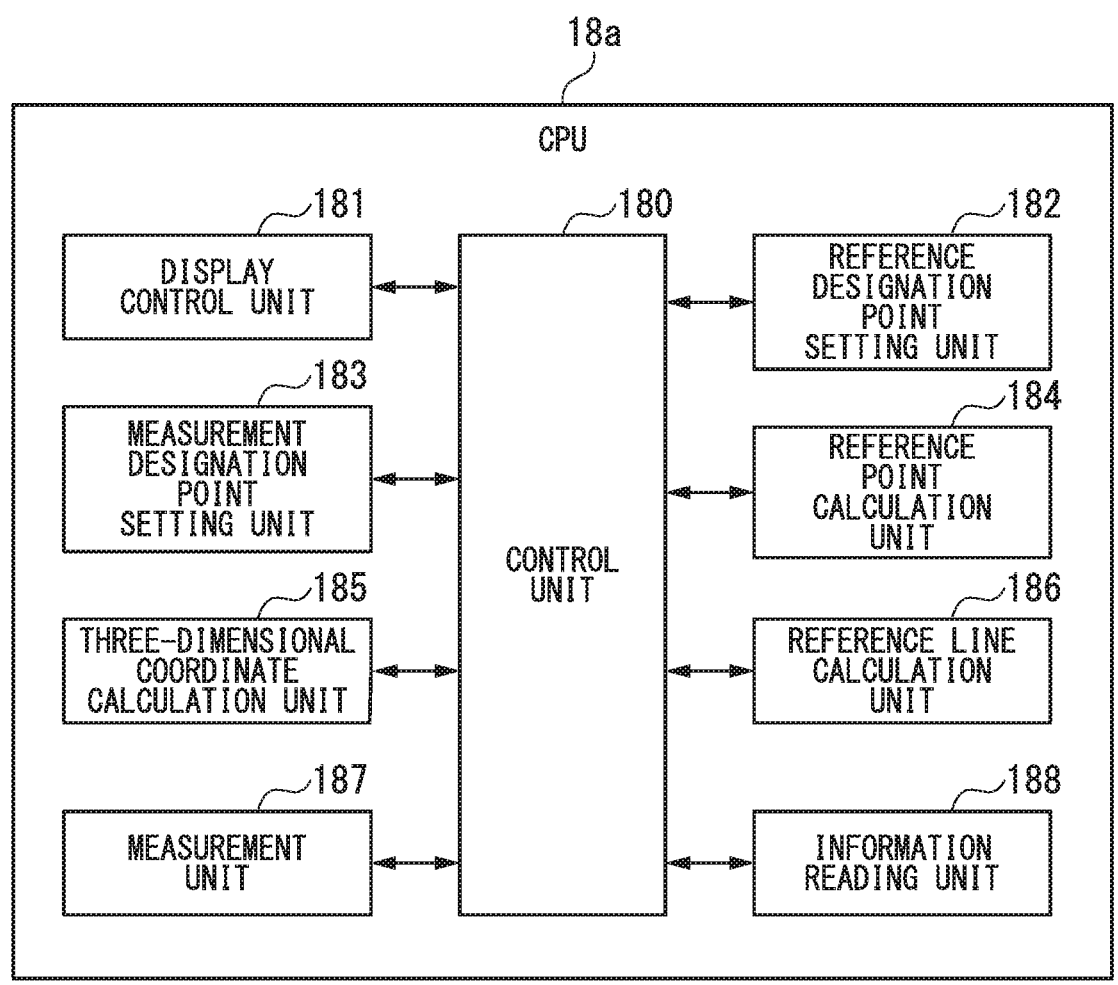
FIG. 3 is a block diagram showing a functional configuration of a CPU according to the first embodiment of the present invention.

FIG. 3 shows a functional configuration of the CPU 18a. The function of the CPU 18a is constituted by a control unit 180, a display control unit 181, a reference designation point setting unit 182, a measurement designation point setting unit 183, a reference point calculation unit 184, a three-dimensional coordinate calculation unit 185, a reference line calculation unit 186, a measurement unit 187, and an information reading unit 188. At least one of blocks shown in FIG. 3 may be constituted by a separate circuit from that of the CPU 18a.

Each unit shown in FIG. 3 may be constituted by at least one of a processor and a logic circuit. For example, the processor is at least one of a CPU, a digital signal processor (DSP), and a graphics processing unit (GPU). For example, the logic circuit is at least one of an application specific integrated circuit (ASIC) and a field-programmable gate array (FPGA). Each unit shown in FIG. 3 can include one or a plurality of processors. Each unit shown in FIG. 3 can include one or a plurality of logic circuits.

The control unit 180 controls a process which is performed by each unit. The display control unit 181 causes the display unit 5 to display an image acquired by the CCU 9. The display control unit 181 displays a cursor for a user to designate a reference designation point and a measurement designation point on an image. The display control unit 181 displays marks of a reference designation point, a measurement designation point, a reference point, and a measurement point on an image. The display control unit 181 displays a line such as a reference line on an image. The display control unit 181 displays a button for a user to perform a predetermined operation on an image. The display control unit 181 displays characters indicating a measurement mode and a measurement result on an image.

For example, the display control unit 181 generates a graphic image signal such as a cursor. The display control unit 181 outputs the generated graphic image signal to the video signal processing circuit 12. The video signal processing circuit 12 combines a video signal output from the CCU 9 and the graphic image signal output from the CPU 18a. Thereby, a cursor or the like is superimposed on an image. The video signal processing circuit 12 outputs the combined video signal to the display unit 5. The display unit 5 displays an image on which a cursor or the like is superimposed. The display control unit 181 detects an instruction for cursor movement input by a user operating the operation unit 4, and sequentially updates the position of the cursor on the basis of the instruction for cursor movement.

The reference designation point setting unit 182 sets a plurality of reference designation points in an image, acquired by the CCU 9 and displayed on the display unit 5, on the basis of a position (first position) designated by a user in the image displayed on the display unit 5. The positions of the plurality of reference designation points are different from each other. In the first embodiment, the reference designation point setting unit 182 sets two reference designation points.

The measurement designation point setting unit 183 (measurement point setting unit) sets a measurement designation point in the image, acquired by the CCU 9 and displayed on the display unit 5, on the basis of a position (second position) designated by a user in the image displayed on the display unit 5. In the first embodiment, the measurement designation point setting unit 183 sets one measurement designation point. In the first embodiment, the measurement designation point setting unit 183 sets a measurement point at the position of the measurement designation point. The second position is the same as or different from the first position.

The operation unit 4 receives the reference designation point and the measurement designation point input by a user operating the operation unit 4. The operation unit 4 outputs information indicating the positions of the reference designation point and the measurement designation point designated by a user. The information output from the operation unit 4 is input to the control interface 17. The information input to the control interface 17 is input to the CPU 18a. The reference designation point setting unit 182 sets a reference designation point on the basis of the information input to the CPU 18a. The measurement designation point setting unit 183 sets a measurement designation point on the basis of the information input to the CPU 18a. Information of the reference designation point and the measurement designation point which are set are held in the RAM 14. The positions of the reference designation point and the measurement designation point are associated with a specific image, and thus the reference designation point and the measurement designation point are set.

As described later, the reference line calculation unit 186 (reference calculation unit) calculates a reference line on the basis of a plurality of reference designation points set by the reference designation point setting unit 182. The reference line is used in a measurement mode indicated by measurement mode information. The reference point calculation unit 184 calculates a plurality of reference points leading to higher reliability of a measurement result instead of a plurality of reference designation points for calculating a reference line. The reference point calculation unit 184 calculates a plurality of reference points on the basis of an image in which a measurement point is set, a plurality of reference designation points, a measurement mode, a plurality of measurement designation points, and the measurement point. The positions of the plurality of reference points are different from each other.

In the first embodiment, the reference point calculation unit 184 calculates two reference points on the basis of the two reference designation points set by the reference designation point setting unit 182. The reference point calculation unit 184 calculates the positions (coordinates) of the reference points. Information of the calculated two reference points is held in the RAM 14. The positions of the reference points are associated with a specific image, and thus the reference points are set. The reference point calculation unit 184 may calculate a portion of the plurality of reference points using a point, located at the same position as that of the reference designation point included in the plurality of reference designation points, as the reference point.

A measurement mode indicated by the measurement mode information indicates any one of the line-based measurement and the plane-based measurement. The measurement mode information indicates a procedure of processes executed in the measurement mode. The measurement mode information includes an algorithm for calculating a reference point in the measurement mode. That is, the measurement mode information indicates a method of calculating a reference point according to the characteristics of the measurement mode. The reference point calculation unit 184 calculates at least one reference point on the basis of the measurement mode indicated by the measurement mode information. The reference point calculation unit 184 calculates at least one reference point located at a position where the reliability of a measurement result becomes higher than in a case where a reference point is set at a position designated by a user. The measurement mode information in the first embodiment indicates the line-based measurement.

The three-dimensional coordinate calculation unit 185 calculates the three-dimensional coordinates of each of a reference designation point, a measurement designation point, a reference point, and a measurement point, using an image acquired by the CCU 9. Specifically, the three-dimensional coordinate calculation unit 185 calculates three-dimensional coordinates corresponding to the position of each of a reference designation point, a measurement designation point, a reference point, and a measurement point on an image acquired by the CCU 9.

The reference line calculation unit 186 calculates a first reference line on the basis of a plurality of reference designation points set by the reference designation point setting unit 182. Specifically, the reference line calculation unit 186 calculates a first reference line, passing through the three-dimensional coordinates of each of two reference designation points, which is a straight line on a three-dimensional space. In addition, the reference line calculation unit 186 calculates a two-dimensional first reference line which is created when the first reference line on a three-dimensional space is projected onto the imaging surface of the imaging device 28. Specifically, the reference line calculation unit 186 calculates the two-dimensional coordinates of projection points obtained by projecting each of a plurality of configuration points constituting the three-dimensional first reference line onto the imaging surface of the imaging device 28. The two-dimensional coordinates of the projection points are calculated using parameters of a camera, stored in the ROM 13, which are obtained for each individual at the time of shipment. For example, the camera parameter is a parameter or the like related to focal length, pixel size, and distortion. The reference line calculation unit 186 calculates the two-dimensional first reference line passing through the projection points, using the two-dimensional coordinates of the projection points. A two-dimensional reference line is not necessarily a straight line due to an influence such as distortion of an optical system. The first reference line is a temporary reference line based on two reference designation points. The first reference line is not necessarily used in the line-based measurement.

The reference line calculation unit 186 calculates a second reference line on the basis of the plurality of reference points calculated by the reference point calculation unit 184. Specifically, the reference line calculation unit 186 calculates a second reference line, passing through the three-dimensional coordinates of each of two reference points, which is a straight line on a three-dimensional space. In addition, the reference line calculation unit 186 calculates a two-dimensional second reference line which is created when the second reference line on a three-dimensional space is projected onto the imaging surface of the imaging device 28. A method of calculating the two-dimensional second reference line is the same as a method of calculating the two-dimensional first reference line. The second reference line is a reference line which is used in the line-based measurement. After the first reference line is calculated on the basis of the plurality of reference designation points, the reference line calculation unit 186 calculates a new second reference line on the basis of the plurality of reference points.

The reference line calculation unit 186 may calculate a first auxiliary line that passes through the three-dimensional coordinates of a measurement designation point and is perpendicular to the three-dimensional first reference line. In addition, the reference line calculation unit 186 may calculate a two-dimensional first auxiliary line which is created when the first auxiliary line on a three-dimensional space is projected onto the imaging surface of the imaging device 28. A method of calculating the two-dimensional first auxiliary line is the same as the method of calculating the two-dimensional first reference line.

The reference line calculation unit 186 may calculate a second auxiliary line that passes through the three-dimensional coordinates of a measurement point and is perpendicular to the three-dimensional second reference line. In addition, the reference line calculation unit 186 may calculate a two-dimensional second auxiliary line which is created when the second auxiliary line on a three-dimensional space is projected onto the imaging surface of the imaging device 28. A method of calculating the two-dimensional second auxiliary line is the same as the method of calculating the two-dimensional second reference line.

The measurement unit 187 executes the measurement of a subject on the basis of a reference line, a measurement point, and a measurement mode. Specifically, the measurement unit 187 executes the measurement of a subject in a measurement mode indicated by the measurement mode information, using a reference line determined on the basis of the plurality of reference points calculated by the reference point calculation unit 184. That is, the measurement unit 187 measures the dimensions of the subject in the measurement mode. Thereby, the measurement unit 187 measures the three-dimensional shape of the subject. In the first embodiment, the measurement unit 187 calculates a three-dimensional distance between the three-dimensional reference line calculated by the reference line calculation unit 186 and the three-dimensional coordinates of the measurement point set by the measurement designation point setting unit 183.

The information reading unit 188 reads out measurement mode information from a recording medium in which the measurement mode information indicating a measurement mode is recorded. The measurement mode information is recorded in the ROM 13. The information reading unit 188 reads out the measurement mode information from the ROM 13.

Figure 4:
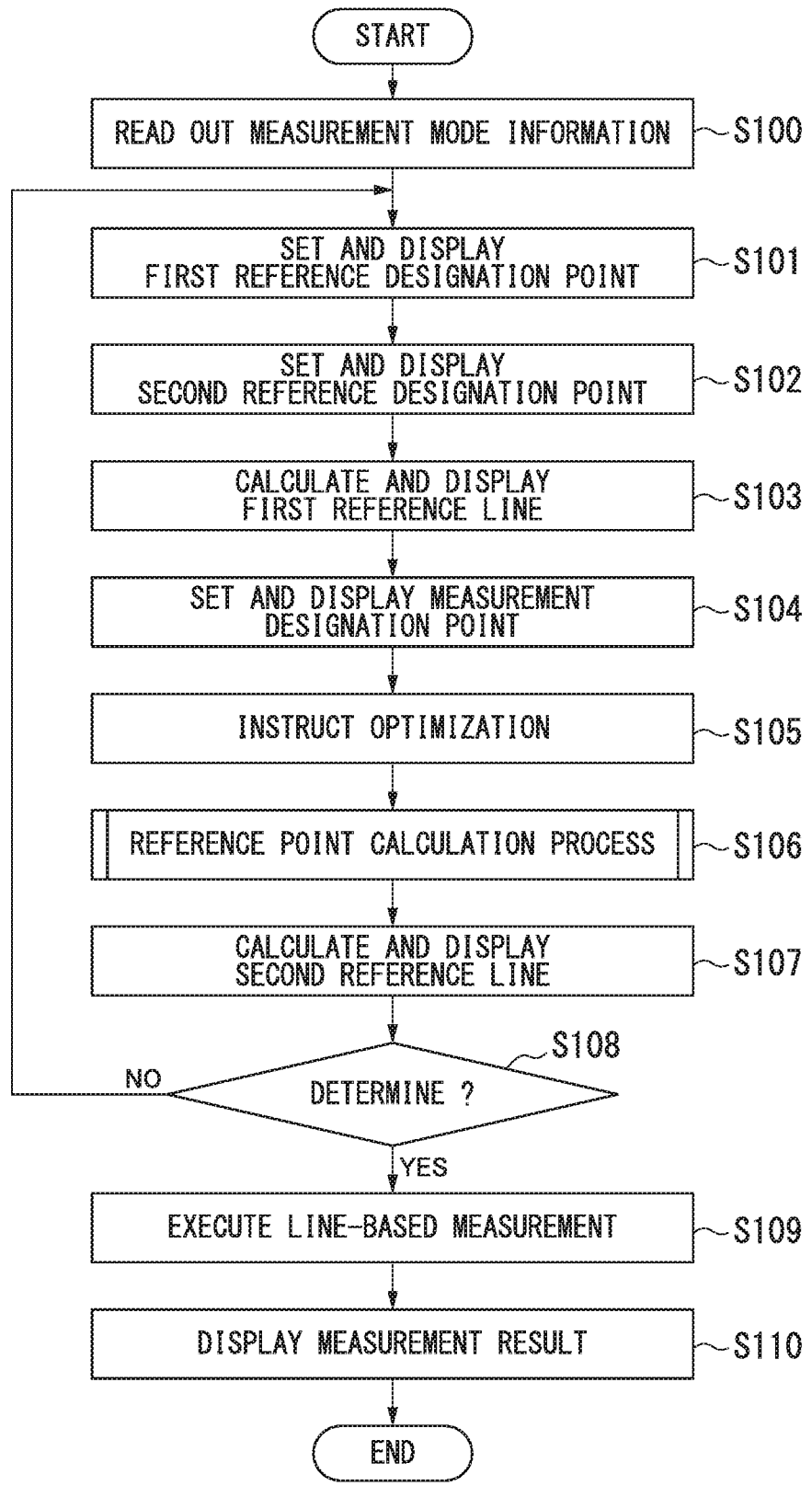
FIG. 4 is a flow diagram showing a procedure of three-dimensional measurement in the first embodiment of the present invention.

Three-dimensional measurement in the first embodiment will be described with reference to FIG. 4. FIG. 4 shows a procedure of the three-dimensional measurement.

The imaging device 28 captures an optical image of a subject, and generates an imaging signal. The CCU 9 acquires an image of a subject by generating a video signal on the basis of the imaging signal. The CPU 18a acquires the image of the subject from the CCU 9 through the video signal processing circuit 12. On the other hand, the video signal output from the CCU 9 is processed by the video signal processing circuit 12, and is output to the display unit 5. The display unit 5 displays the image of the subject on the basis of the video signal. A user can designate a reference designation point and a measurement designation point in the image of the subject by operating the operation unit 4. A cursor is displayed on the image of the subject, but the cursor is omitted in the following description.

The information reading unit 188 reads out the measurement mode information from the ROM 13 (step S100). The read-out measurement mode information indicates the line-based measurement. Each unit of the CPU 18a executes a process specified in the line-based measurement.

After step S100, the reference designation point setting unit 182 determines a position designated as a reference designation point by a user on the basis of the operation result of the operation unit 4, and sets a first reference designation point at the position. The display control unit 181 displays the first reference designation point on the image (step S101).

After step S101, the reference designation point setting unit 182 determines a position designated as a reference designation point by a user on the basis of the operation result of the operation unit 4, and sets a second reference designation point at the position. The display control unit 181 displays the second reference designation point on the image (step S102).

After step S102, the three-dimensional coordinate calculation unit 185 calculates the three-dimensional coordinates of each of the first reference designation point and the second reference designation point. The reference line calculation unit 186 calculates the first reference line passing through the three-dimensional coordinates of each of the first reference designation point and the second reference designation point. The reference line calculation unit 186 calculates the two-dimensional first reference line which is created when the first reference line on a three-dimensional space is projected onto the imaging surface of the imaging device 28. The display control unit 181 causes the display unit 5 to display a two-dimensional reference line (step S103).

After step S103, the measurement designation point setting unit 183 determines a position designated as a measurement designation point by a user on the basis of the operation result of the operation unit 4, and sets the measurement designation point at the position. The display control unit 181 displays the measurement designation point on the image (step S104). In the first embodiment, the measurement designation point is the same as a measurement point. Therefore, the measurement designation point set in step S104 is also handled as the measurement point.

In step S104, the reference line calculation unit 186 may calculate the first auxiliary line that passes through the three-dimensional coordinates of the measurement designation point and is perpendicular to the three-dimensional first reference line. In step S104, the reference line calculation unit 186 may calculate the two-dimensional first auxiliary line which is created when the first auxiliary line on a three-dimensional space is projected onto the imaging surface of the imaging device 28. In step S104, the display control unit 181 may cause the display unit 5 to display the two-dimensional first auxiliary line.

After step S104, a user inputs an instruction for the optimization of a reference point by operating the operation unit 4. The operation unit 4 receives the instruction, and outputs information indicating the instruction. The information output from the operation unit 4 is input to the control interface 17. The information input to the control interface 17 is input to the CPU 18a. The control unit 180 detects the instruction for the optimization of a reference point (step S105).

After step S105, a reference point calculation process is executed (step S106). In the reference point calculation process, the reference point calculation unit 184 calculates a first reference point and a second reference point at which the reliability of a measurement result becomes higher than in a case where measurement based on the first reference designation point and the second reference designation point is executed. The details of the reference point calculation process will be described later.

After step S106, the reference line calculation unit 186 calculates the second reference line passing through the three-dimensional coordinates of each of the first reference point and the second reference point. The reference line calculation unit 186 calculates the two-dimensional second reference line which is created when the second reference line on a three-dimensional space is projected onto the imaging surface of the imaging device 28. The display control unit 181 causes the display unit 5 to display the two-dimensional second reference line (step S107).

In step S107, the reference line calculation unit 186 may calculate the second auxiliary line that passes through the three-dimensional coordinates of the measurement point and is perpendicular to the three-dimensional second reference line. In step S107, the reference line calculation unit 186 may calculate the two-dimensional second auxiliary line which is created when the second auxiliary line on a three-dimensional space is projected onto the imaging surface of the imaging device 28. In step S107, the display control unit 181 may cause the display unit 5 to display the two-dimensional second auxiliary line.

After step S107, a user determines whether the first reference point and the second reference point are adopted as formal reference points. A user inputs the determination result by operating the operation unit 4. The operation unit 4 receives the determination result, and outputs information indicating the determination result. The determination result output from the operation unit 4 is input to the control interface 17. The determination result input to the control interface 17 is input to the CPU 18a. The control unit 180 determines whether a user has adopted the first reference point and the second reference point as formal reference points on the basis of the determination result (step S108).

In step S108, in a case where the control unit 180 determines that a user has not adopted the first reference point and the second reference point as formal reference points, the process in step S101 is executed. In this case, a user can set the first reference designation point and the second reference designation point again.

In step S108, in a case where the control unit 180 determines that a user has adopted the first reference point and the second reference point as formal reference points, the measurement unit 187 executes the line-based measurement. That is, the measurement unit 187 calculates a three-dimensional distance between the three-dimensional second reference line calculated in step S107 and the three-dimensional coordinates of the measurement point (step S109).

After step S109, the display control unit 181 causes the display unit 5 to display a measurement result. That is, the display control unit 181 causes the display unit 5 to display the three-dimensional distance calculated in step S109 (step S110). The process in step S110 is executed, and thus the three-dimensional measurement is terminated.

In the above example, the first reference point and the second reference point are calculated on the basis of the first reference designation point and the second reference designation point. Any one of the first reference designation point and the second reference designation point may be set to a reference point. Another reference point may be calculated through the same process as the above process on the basis of the first reference designation point and the second reference designation point.

Any one of the two reference designation points and the first reference line may be displayed. Any one of the two reference points and the second reference line may be displayed. Display of the reference designation point and the measurement designation point is not essential. Display of the reference point and the measurement point is not essential. Display of the first reference line and the second reference line is not essential. Display of the measurement result is not essential.

Figure 5A:
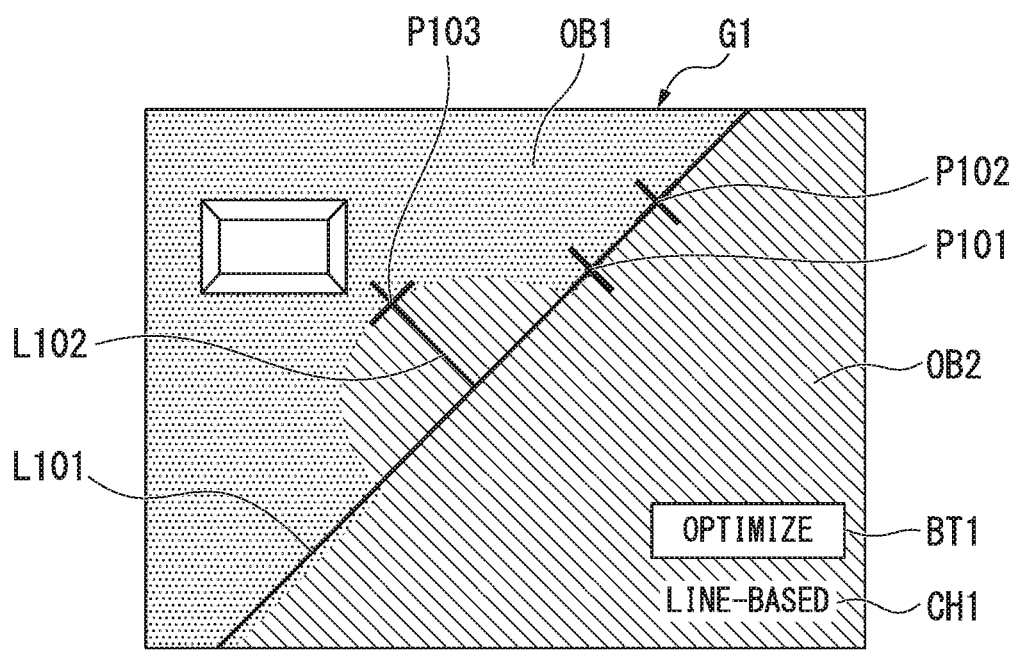
FIGS. 5A and 5B are diagrams showing an example of an image displayed on a display unit according to the first embodiment of the present invention.

FIG. 5A shows an example of an image displayed on the display unit 5. As shown in FIG. 5A, an image G1 is displayed. The image G1 includes images of a subject OB1 and a subject OB2. Characters CH1 indicating a measurement mode are displayed on the image G1. The characters CH1 indicate that the measurement mode is line-based measurement. The image G1 after a measurement designation point is designated in step S104 is shown in FIG. 5A.

In step S101, a first reference designation point P101 on the edge of the subject OB1 is set. In step S102, a second reference designation point P102 on the edge of the subject OB1 is set. The first reference designation point P101 and the second reference designation point P102 are displayed on the image G1. In step S103, the first reference line is calculated. A two-dimensional first reference line L101 is displayed on the image G1. In the example shown in FIG. 5A, the first reference line L101 is not coincident with the edge of the subject OB1. In step S104, a measurement designation point P103 on the edge of the subject OB1 is set.

The measurement designation point P103 and a two-dimensional first auxiliary line L102 are displayed on the image G1.

A button BT1 is displayed on the image G1. A user can press the button BT1 by operating the operation unit 4. For example, a user performs a predetermined operation when a cursor overlaps the button BT1, and thus the button BT1 is pressed. When the button BT1 is pressed, the instruction for the optimization of a reference point is input in step S105.

Figure 5B:
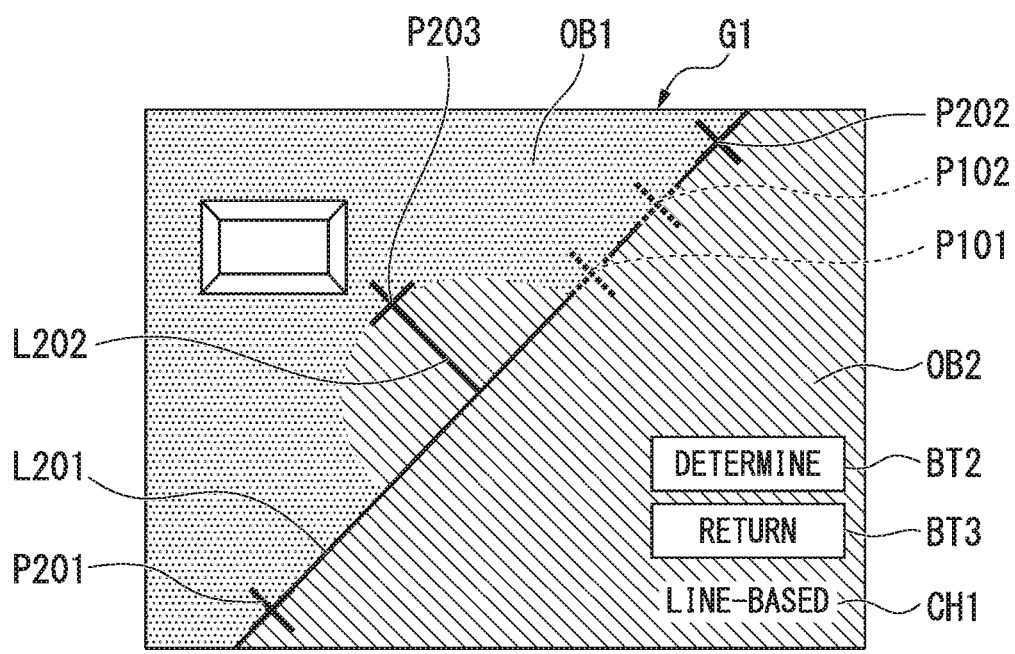

FIG. 5B shows an example of an image displayed on the display unit 5 when the button BT1 shown in FIG. 5A is pressed. In step S106, a first reference point P201 and a second reference point P202 are calculated. The first reference point P201 and the second reference point P202 are displayed on the image G1. The display control unit 181 may cause the display unit 5 to display the first reference designation point P101 and the second reference designation point P102 together with the first reference point P201 and second the reference point P202. The reference points and the reference designation points are displayed, and thus a user can confirm whether the position of a reference point intended by a user and the position of an estimated reference point are coincident with each other.

A measurement point P203 is displayed at the same position as that of the measurement designation point P103. In step S107, the second reference line is calculated. A two-dimensional second reference line L201 is displayed on the image G1. A two-dimensional second auxiliary line L202 is displayed on the image G1.

In the example shown in FIG. 5B, the second reference line L201 is well coincident with the edge of the subject OB1. Therefore, it can be expected that a measurement result having high reliability is obtained.

A button BT2 and a button BT3 are displayed on the image G1. A user can press the button BT2 and the button BT3 by operating the operation unit 4. In a case where it is determined that a user adopts the first reference point and the second reference point as formal reference points, the user presses the button BT2. In a case where it is determined that a user does not adopt the first reference point and the second reference point as formal reference points, the user presses the button BT3. When the button BT2 or the button BT3 is pressed, the determination result is input. When the button BT2 is pressed, the line-based measurement is executed in step S109. When the button BT3 is pressed, a user can set the first reference point again in step S101.

As shown in FIG. 5B, the display control unit 181 causes the display unit 5 to display a plurality of reference points calculated by the reference point calculation unit 184 and the second reference line determined on the basis of the plurality of reference points, on the image.

As shown in FIGS. 5A and 5B, the display control unit 181 causes the display unit 5 to display the plurality of reference points calculated by the reference point calculation unit 184 and the plurality of reference designation points set by the reference designation point setting unit 182, on the image. The reference points and the reference designation points may be displayed simultaneously.

As shown in FIGS. 5A and 5B, the display control unit 181 causes the display unit 5 to display the second reference line and the first reference line on the image. The second reference line is determined on the basis of the plurality of reference points calculated by the reference point calculation unit 184. The first reference line is determined on the basis of the plurality of reference designation points set by the reference designation point setting unit 182. The second reference line and the first reference line may be displayed simultaneously.

Figure 6:
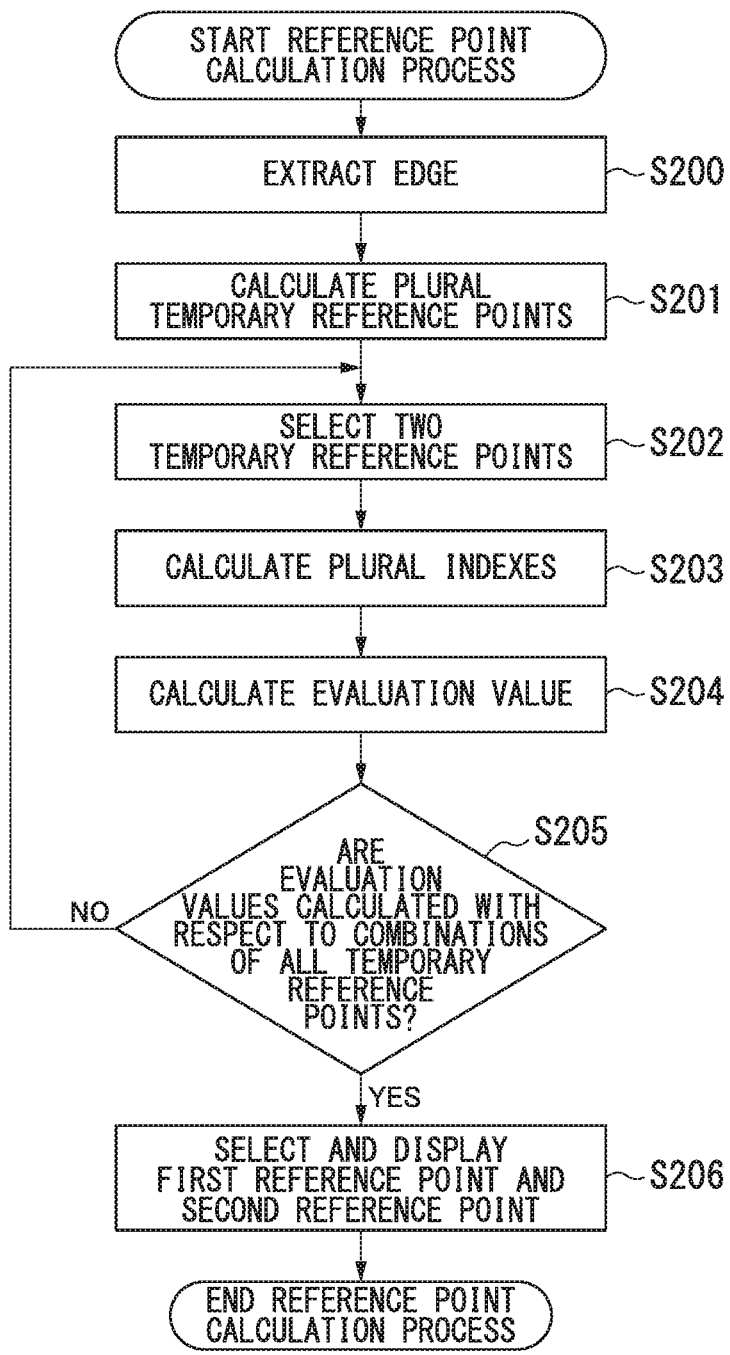
FIG. 6 is a flow diagram showing a procedure of a reference point calculation process in the first embodiment of the present invention.

FIG. 6 shows a procedure of the reference point calculation process in step S106. The details of the reference point calculation process will be described with reference to FIG. 6.

The reference point calculation unit 184 extracts an edge by executing a process using a differential filter for the image acquired by the CCU 9. An example of the differential filter which can be used includes a LoG filter, a Sobel filter, a Prewitt filter, and the like. The reference point calculation unit 184 generates an edge image constituted by the extracted edge (step 200).

Figure 7A:
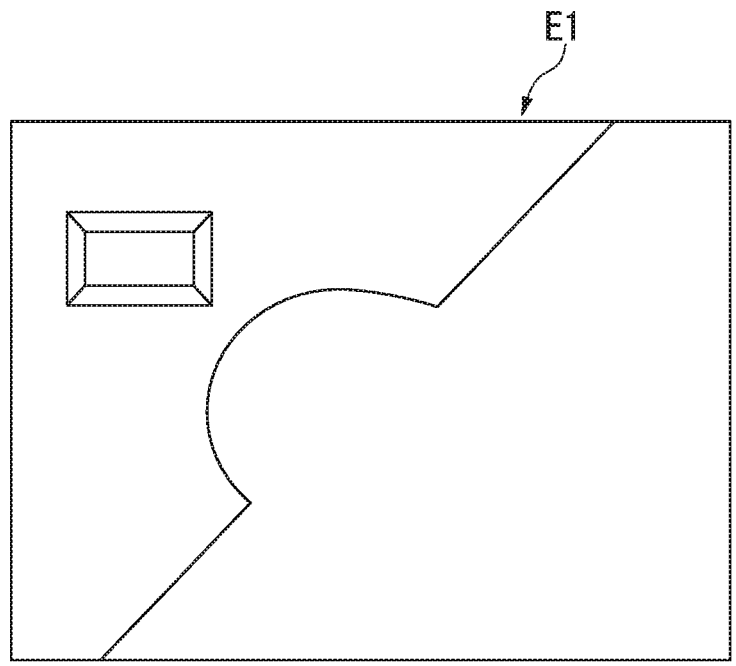
FIGS. 7A and 7B are diagrams showing an example of an edge image according to the first embodiment of the present invention.

FIG. 7A shows an example of an edge image. An edge image E1 shown in FIG. 7A is constituted by the edge extracted from the image G1 shown in FIG. 5A.

After step S200, the reference point calculation unit 184 calculates a plurality of temporary reference points on the basis of the two-dimensional first reference line calculated in step S103 (step S201). In step S201, three or more temporary reference points are calculated. Information of the calculated temporary reference points is held in the RAM 14.

Figure 7B:
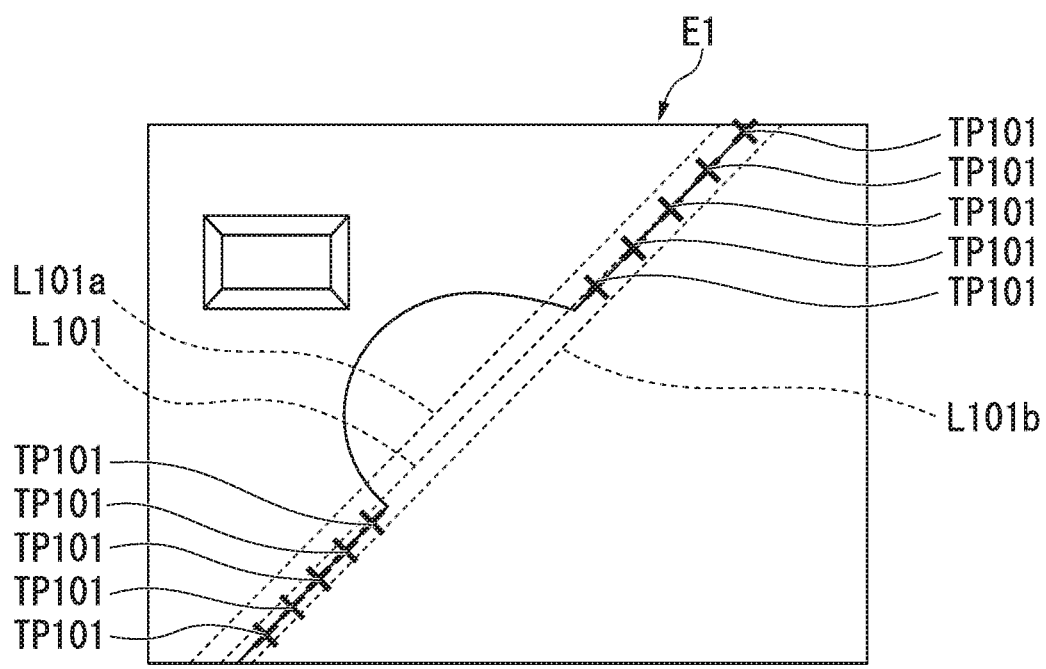

The details of the process in step S201 will be described. For the efficiency of arithmetic operation, it is assumed that an optimum reference point is present in the vicinity of the two-dimensional first reference line calculated in step S103. As shown in FIG. 7B, the reference point calculation unit 184 sets the first reference line L101 in the edge image E1. The reference point calculation unit 184 calculates temporary reference points TP101 in a predetermined range based on the first reference line L101. Specifically, the reference point calculation unit 184 extracts the temporary reference points TP101 from the edge of the image in a range within a distance of ten pixels from the first reference line L101. In the example shown in FIG. 7B, ten temporary reference points TP101 are extracted in a range between a line L101a and a line L101b located at a distance of ten pixels from the first reference line L101. These temporary reference points TP101 are candidates of the reference point. For example, intervals between the ten temporary reference points TP101 are approximately equal to each other. Points extracted as the temporary reference points are limited, and thus the amount of arithmetic operation is drastically reduced.

After step S201, the reference point calculation unit 184 selects two temporary reference points from a plurality of temporary reference points (step S202). The process in step S202 is executed multiple times. In the first process, any two temporary reference points are selected. A combination of two temporary reference points selected in the N-th process is different from a combination of two temporary reference points selected in the first to (N−1)-th processes. N is an integer equal to or greater than 2.

After step S202, the reference point calculation unit 184 calculates a plurality of indexes (step S203).

The details of the process in step S203 will be described. In the following example, the reference point calculation unit 184 calculates an index A, an index B, and an index C. The index A indicates the magnitude of the distance between two temporary reference points. The index B relates to a positional relationship between two temporary reference points and a measurement designation point. The index B indicates the magnitude of the distance between the intersection point of a perpendicular line from a measurement designation point to a reference line with the reference line and the centroid of two temporary reference points. The intersection point of a perpendicular line from a measurement designation point to a reference line with the reference line is a point closest to the measurement designation point on the reference line. The perpendicular line from a measurement designation point to a reference line is a straight line that passes through the measurement designation point and is perpendicular to the reference line. The centroid of two temporary reference points is a central point between two temporary reference points. The index C indicates the degree of coincidence of a two-dimensional reference line with the edge of an image. Each of the indexes is normalized so as to be set between 0 and 1. The measurement mode information includes information of indexes calculated in the reference point calculation process. That is, the indexes calculated in the reference point calculation process are specified by the measurement mode information.

The reference point calculation unit 184 calculates a reference line used in the calculation of each index, on the basis of the two temporary reference points selected in step S202. The reference line calculation unit 186 may calculate a reference line used in the calculation of each index.

The reference point calculation unit 184 calculates the index A on the basis of Expression (1) and Expression (2). In Expression (1), W is the transverse size of an image, and H is the longitudinal size of the image. L in Expression (1) is represented by Expression (2). In Expression (2), the coordinates of two temporary reference points are $(x_1, y_1)$ and $(x_2, y_2)$, respectively. As the distance between two temporary reference points increases, the index A increases.

$$A = \frac{L}{\sqrt{W^2 + H^2}} \quad (1)$$

$$L = \sqrt{(x_1 - x_2)^2 + (y_1 - y_2)^2} \quad (2)$$

The reference point calculation unit 184 calculates the index B on the basis of Expression (3), Expression (4), and Expression (5). D in Expression (3) and Expression (4) is represented by Expression (5). L in Expression (3) and Expression (4) is represented by Expression (2). In Expression (5), the coordinates of two temporary reference points are $(x_1, y_1)$ and $(x_2, y_2)$, respectively. In Expression (5), the coordinates of the intersection point of a perpendicular line from a measurement designation point to a two-dimensional reference line with the reference line is $(x_C, y_C)$. As the distance between the intersection point and the centroid of two temporary reference points decreases, the index B increases.

$$\text{When } \frac{D}{L} < 1 \quad B = 1 - \frac{D}{L} \quad (3)$$

$$\text{When } \frac{D}{L} \geq 1 \quad B = 0 \quad (4)$$

$$D = \sqrt{\left(x_c - \frac{x_1 + x_2}{2}\right)^2 + \left(y_c - \frac{y_1 + y_2}{2}\right)^2} \quad (5)$$

The reference point calculation unit 184 calculates the index C on the basis of Expression (6). In Expression (6), $N_A$ is the number of pixels of a reference line on an image. The reference point calculation unit 184 calculates $N_A$ by counting the number of pixels on the reference line, in edge image E1 shown in FIG. 7A. In Expression (6), $N_B$ is the number of pixels on which the edge on the image and the reference line are coincident with each other. The reference point calculation unit 184 calculates $N_B$ by counting the number of pixels on which the edge and the reference line overlap each other in the edge image E1 shown in FIG. 7A. As the degree of coincidence of the two-dimensional reference line with the edge of the image becomes higher, the index C increases.

$$C = \frac{N_B}{N_A} \quad (6)$$

After step S203, the reference point calculation unit 184 calculates an evaluation value by calculating the sum of a plurality of indexes (step S204). For example, in step S204, the reference point calculation unit 184 calculates the sum of the index A, the index B, and the index C. The reference point calculation unit 184 may calculate the product of three indexes. The reference point calculation unit 184 may multiply each index by a coefficient for weighting, and take the sum thereof.

After step S204, the reference point calculation unit 184 determines whether evaluation values are calculated with respect to the combinations of all the temporary reference points (step S205).

In step S205, in a case where the reference point calculation unit 184 determines that there is a combination of two temporary reference points for which an evaluation value is not calculated, the process in step S202 is executed. In that case, the combination of two temporary reference points is changed, and a plurality of indexes and the evaluation value are calculated for each combination of temporary reference points.

In step S205, in a case where the reference point calculation unit 184 determines that evaluation values are calculated with respect to the combinations of all the temporary reference points, the reference point calculation unit 184 selects a combination of two temporary reference points having the maximum evaluation value. Thereby, the reference point calculation unit 184 selects the first reference point and the second reference point. The selected two temporary reference points are the first reference point and the second reference point, respectively. The display control unit 181 displays the first reference point and the second reference point on the image (step S206). The process in step S206 is executed, and thus the reference point calculation process is terminated.

In the reference point calculation process shown in FIG. 6, the reference point calculation unit 184 calculates at least one reference point included in the plurality of reference points such that a position of the at least one reference point satisfies a criterion according to the characteristics of a measurement mode indicated by the measurement mode information.

In step S201, the reference point calculation unit 184 sets a plurality of temporary reference points in the image displayed on the display unit 5. The positions of the plurality of temporary reference points are different from each other. In the first embodiment, at least three temporary reference points are set. In step S202, the reference point calculation unit 184 selects a combination including at least two temporary reference points. In steps S203 and S204, for each combination of temporary reference points, the reference point calculation unit 184 calculates an evaluation value indicating a degree to which at least two temporary reference points included in the combination are suitable for a criterion. In a case where a first degree indicated by the evaluation value of a first combination is higher than a second degree indicated by the evaluation value of a second combination, in step S206, the reference point calculation unit 184 sets at least one of at least two temporary reference points included in the first combination to the reference point.

In step S203, for each combination of temporary reference points, the reference point calculation unit 184 calculates a plurality of indexes different from each other for each of a plurality of criteria, on the basis of the positions of at least two temporary reference points included in the combination. In step S204, the reference point calculation unit 184 calculates an evaluation value, for each combination of temporary reference points, on the basis of the plurality of indexes.

In the reference point calculation process, the reference point calculation unit 184 calculates a plurality of reference points such that distances between the plurality of reference points become larger. The reference point calculation unit 184 calculates a plurality of reference points such that the distances between the plurality of reference points become larger than distances between a plurality of reference designation points. For example, the minimum value of the distances between the plurality of reference points is larger than the minimum value of the distances between the plurality of reference designation points, and the maximum value of the distances between the plurality of reference points is larger than the maximum value of the distances between the plurality of reference designation points. The average of the distances between the plurality of reference points may be larger than the average of the distances between the plurality of reference designation points. The reference point calculation unit 184 calculates a plurality of reference points that satisfy the above conditions, on the basis of the evaluation value in which the index A is reflected.

In the reference point calculation process, the reference point calculation unit 184 calculates a plurality of reference points such that the intersection point of a perpendicular line from a measurement point or a measurement designation point to a reference line with the reference line comes close to the centroid of the plurality of reference points. The reference point calculation unit 184 calculates a plurality of reference points such that a first distance becomes smaller than a second distance. The first distance is a distance between the intersection point of a perpendicular line from a measurement point or a measurement designation point to the second reference line with the second reference line and the centroid of the plurality of reference points. The second distance is a distance between the intersection point of a perpendicular line from a measurement point or a measurement designation point to the first reference line with the first reference line and the centroid of the plurality of reference designation points. The reference point calculation unit 184 calculates a plurality of reference points that satisfy the above conditions, on the basis of the evaluation value in which the index B is reflected.

The reference point calculation unit 184 calculates a plurality of reference points such that a degree to which the reference line approximates the end of a subject becomes higher. The reference point calculation unit 184 calculates a plurality of reference points such that the first degree becomes higher than the second degree. The first degree is a degree to which the second reference line determined on the basis of the plurality of reference points approximates the end of the subject. The second degree is a degree to which the first reference line determined on the basis of the plurality of reference designation points approximates the end of the subject. The reference point calculation unit 184 calculates a plurality of reference points that satisfy the above conditions, on the basis of the evaluation value in which the index C is reflected.

Even in a case where a user who does not have a full understanding of the principle of measurement, the measurement mode and the like performs measurement, the reference point calculation process is executed, and thus an optimum reference point for the line-based measurement mode is set.

After the reference point is calculated in the above method, the reference point calculation unit 184 may more finely calculate the coordinates of an optimum reference point in the vicinity of the coordinates of the reference point. A range in which temporary reference points are extracted and the number of temporary reference points are determined in consideration of a balance between processing time required depending on a system and calculation accuracy for an optimum reference point position. A method of obtaining the position of an optimum reference point may be a method of repeatedly performing optimization using, for example, a Levenberg-Marquardt method. The type of algorithm for calculating an optimum reference point does not matter.

Other indexes excluding the index A, the index B, and the index C may be used. For example, an index related to a distance between a reference designation point designated by a user and a temporary reference point may be used. As the distance decreases, the index increases. An index related to the correlation value of matching at a temporary reference point may be used. On the basis of the coordinates of a temporary reference point set in one of two images in the stereo measurement, the coordinates of a corresponding point in the other of the two images are calculated by a matching process. The correlation value is calculated in the process. As the correlation value increases, the index increases.

An index related to a distance between a temporary reference point and an edge on an image may be used. As the distance decreases, the index increases. An index related to the strength of texture at a temporary reference point may be used. As the texture becomes stronger, the index increases. An index related to the degree of coincidence of a reference line calculated from two temporary reference points with the three-dimensional coordinates of an edge in a three-dimensional image may be used. As the degree of coincidence of the reference line with the three-dimensional coordinates of the edge becomes higher, the index increases. Indexes other than these indexes may be used. One or two of the index A, the index B, and the index C and other indexes may be used. Only one or two of the index A, the index B, and the index C may be used.

Even in a case where a user is not able to determine an optimum reference point just through the appearance of an image, the reference point calculation unit 184 can easily calculate the optimum reference point by combining the above indexes.

Figure 8A:
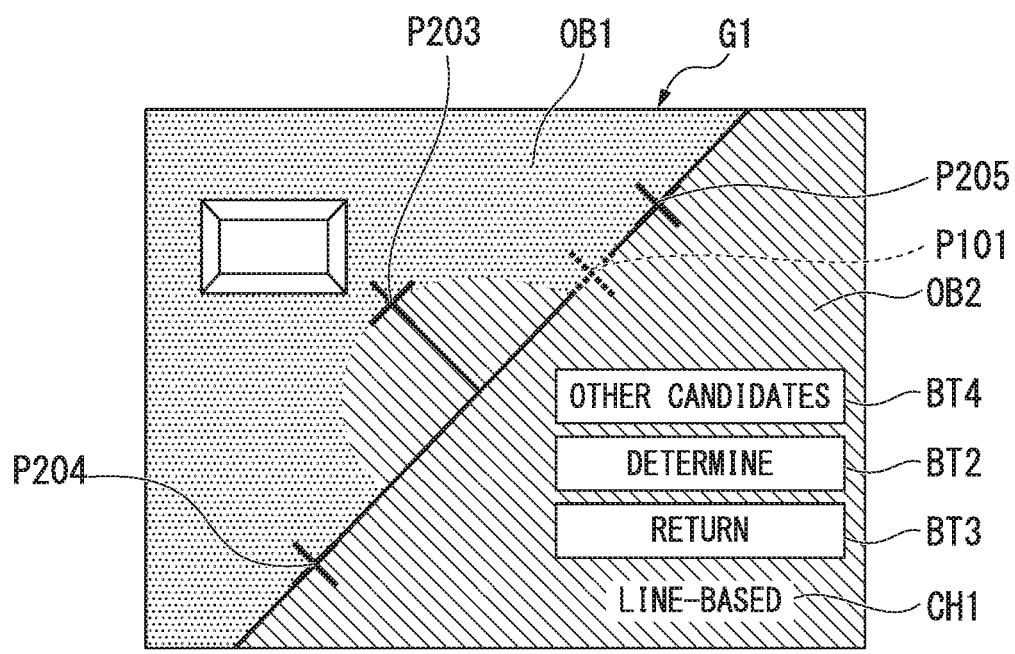
FIGS. 8A and 8B are diagrams showing an example of an image displayed on the display unit according to the first embodiment of the present invention.

A user's intention may be considered in order to determine an optimum reference point. For example, in step S108, as shown in FIG. 8A, a button BT4 may be displayed on the image G1. A user can press the button BT4 through the same operation as the operation of the button BT1 shown in FIG. 5A. When the button BT4 is pressed, the first reference point and the second reference point are changed. That is, a combination of two temporary reference points constituting the first reference point and the second reference point is changed.

Initially, two temporary reference points having the maximum evaluation value are selected as the first reference point and the second reference point, and these temporary reference points are displayed. When the button BT4 is pressed, a combination of two temporary reference points selected as the first reference point and the second reference point is changed. In the example shown in FIG. 8A, when the button BT4 is pressed, a first reference point P204 and a second reference point P205 are displayed. The position of the second reference point P205 is the same as the position of the second reference designation point P102 shown in FIG. 5A. That is, one of two reference designation points designated by a user is selected as the reference point, and the other of the two reference designation points is optimized. That is, the reference point calculation unit 184 calculates a point, located at the same position as one position of the two reference designation points, as the reference point. The reference point calculation unit 184 sets only the other of the two reference points as a target for optimization, and calculates a point located at a position different from the position of the reference designation point as the reference point.

Figure 8B:
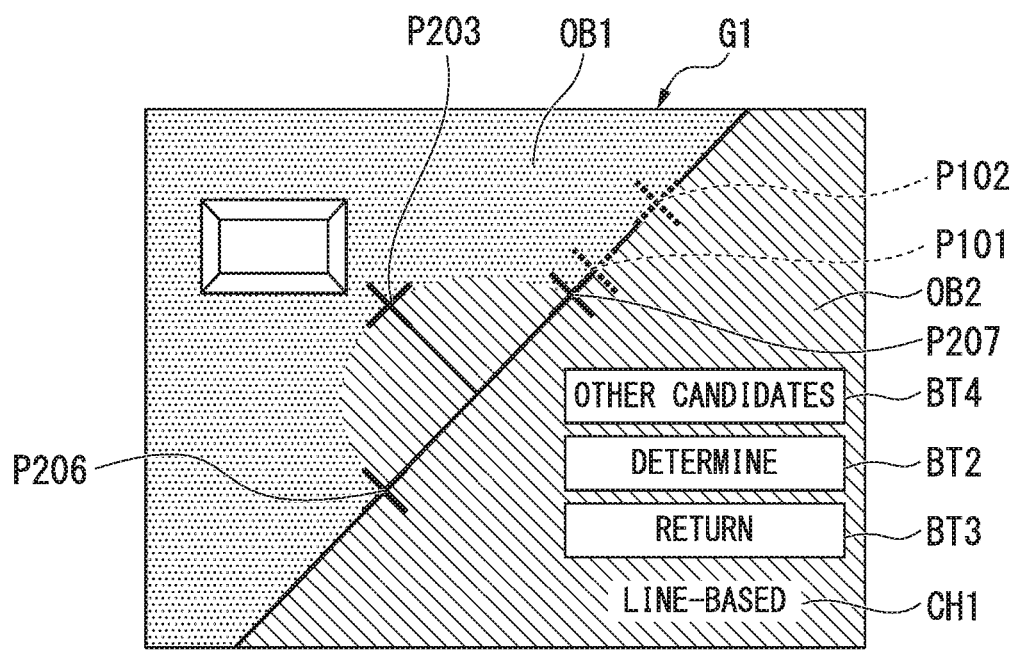

In the example shown in FIG. 8B, when the button BT4 is pressed, the first reference point P206 and a second reference point P207 are displayed. In this example, weighting of the index A is set to be small, and an evaluation value is calculated again for each combination of temporary reference points. A combination of two temporary reference points having the maximum calculated evaluation value is selected.

When other candidates of two reference points are calculated, the reference point calculation unit 184 can calculate candidates of two reference points having characteristics different from the characteristics of the two reference points calculated previously, through the introduction of a new index or the change of weighting of each index.

The display control unit 181 may cause the display unit 5 to display information for assisting a user's selection of reference points. For example, the display control unit 181 may cause the display unit 5 to display the value of each index used in the calculation of reference points. Alternatively, the display control unit 181 may cause the display unit 5 to display the degree of weighting of each index used in the calculation of reference points. Alternatively, the display control unit 181 may cause the display unit 5 to display a message indicating that the calculated reference points are well coincident with an edge on an image.

Before a user determines whether the first reference point and the second reference point are adopted as formal reference points, the result of the line-based measurement based on the first reference point and the second reference point may be displayed. As shown in FIGS. 8A and 8B, even in a case where the endoscope device 1 is configured so that a user can designate other candidates of two reference points, the result of the line-based measurement may be displayed before the user's determination. Thereby, the user can confirm other candidates of reference points and the measurement result at any time. Therefore, the user can also determine the validity of reference points in consideration of the measurement result.

After step S104 shown in FIG. 4, the process in step S106 may be executed. That is, the process in step S105 may be omitted.

After step S107 shown in FIG. 4, the process in step S109 may be executed. That is, the process in step S108 may be omitted. In this case, the endoscope device 1 can obtain an optimum measurement result when a user just designates the reference designation points. The process in step S108 may be omitted, and the first reference point and the second reference point calculated on the basis of two reference designation points do not need to be displayed. In this case, a user does not need to confirm reference points.

After the reference point and the measurement point are displayed, a user may be able to freely correct the positions of the reference point and the measurement point. A user may input an instruction for designating the positions of the reference point or the measurement point by operating the operation unit 4. The operation unit 4 receives the instruction, and outputs information indicating the instruction. The information output from the operation unit 4 is input to the control interface 17. The information input to the control interface 17 is input to the CPU 18*a*. The reference point calculation unit 184 changes the position of the reference point designated by a user to a position designated by the user. The measurement designation point setting unit 183 changes the position of the measurement point to a position designated by the user. Thereby, the user can refer to the positions of the reference point and the measurement point presented by the endoscope device 1, and finely adjust these positions. Therefore, a measurement result at a position intentionally designated by the user is obtained.

In the above example, two reference points are calculated, but three or more reference points may be calculated, and the reference line may be calculated on the basis of these reference points. Thereby, the probability of the reference line rises. In the above example, the reference line is a straight line, but the reference line may be a curved line.

As described above, the reference point calculation unit 184 calculates at least one reference point on the basis of the measurement mode indicated by the measurement mode information. A reference point at a position having a tendency to be high in the reliability of the measurement result is calculated. A user does not need to accurately designate the position (first position) of the reference designation point. Therefore, the endoscope device 1 can simplify a user's designation of the reference point, and improve the reliability of the measurement result.

A user does not need to accurately designate points in units of sub-pixels as in the related art. Therefore, the endoscope device 1 can drastically reduce the burden of a user's operation due to an input particularly using a touch panel or the like. Even in a case where a user who has no knowledge pertaining to a three-dimensional measurement function operates the endoscope device 1, the endoscope device 1 can obtain a measurement result having high reliability.

As described above, a reference point automatically calculated by the endoscope device 1 is displayed. Thereby, a user can confirm whether the reference point is suitable for measurement.

Modification Example of First Embodiment

Figure 9:
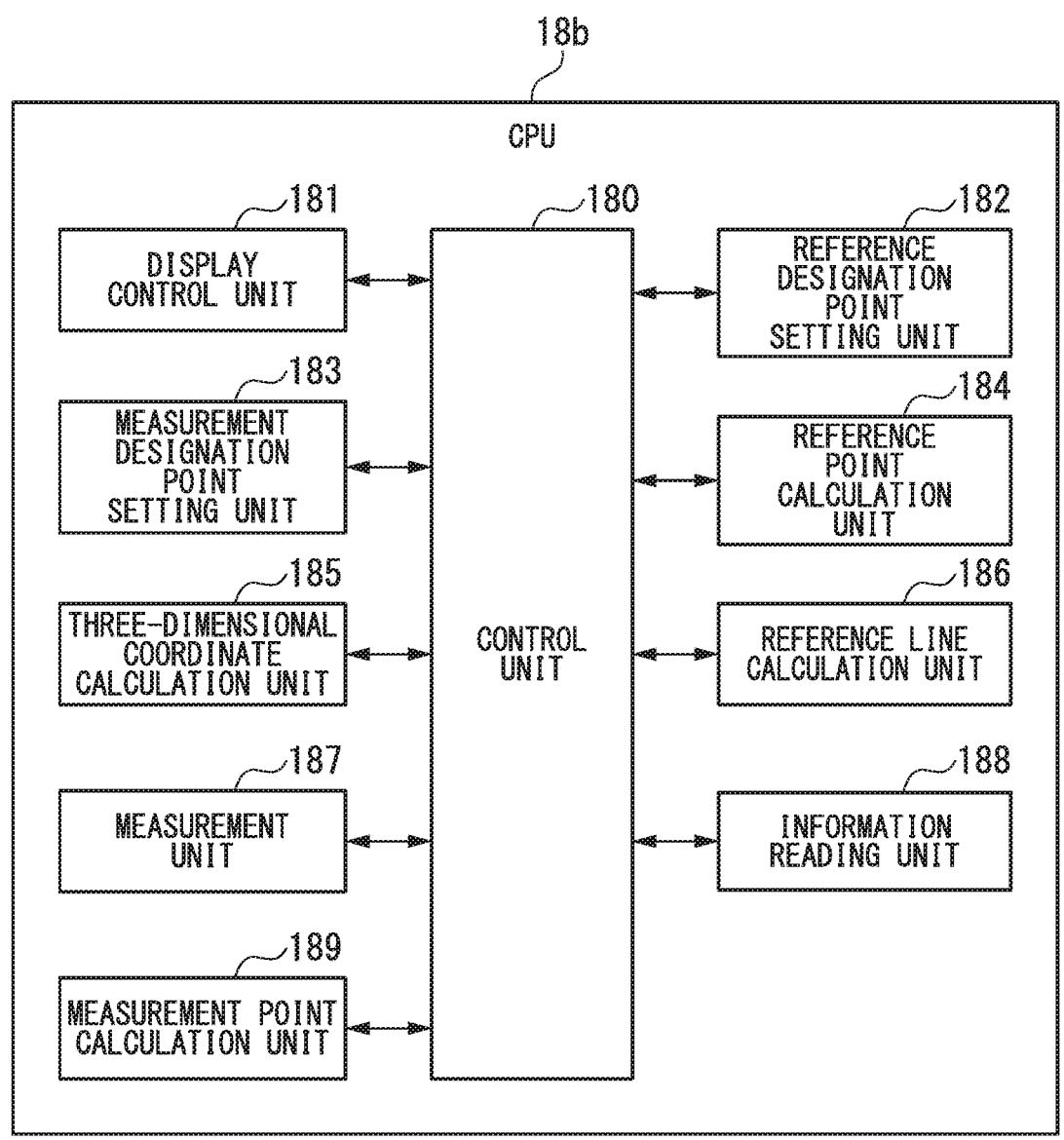
FIG. 9 is a block diagram showing a functional configuration of a CPU according to a modification example of the first embodiment of the present invention.

In a modification example of the first embodiment of the present invention, the CPU 18*a* in the first embodiment is changed to a CPU 18*b* shown in FIG. 9. FIG. 9 shows a functional configuration of the CPU 18*b*. Regarding a configuration shown in FIG. 9, points different from those of the configuration shown in FIG. 3 will be described.

The CPU 18*b* includes a measurement point calculation unit 189 in addition to the configuration shown in FIG. 3. The measurement point calculation unit 189 calculates a measurement point on the basis of the plurality of reference designation points set by the reference designation point setting unit 182. In other words, the measurement point calculation unit 189 calculates a measurement point on the basis of the plurality of reference points calculated by the reference point calculation unit 184. In other words, the measurement point calculation unit 189 calculates a measurement point on the basis of the reference line calculated by the reference line calculation unit 186. The measurement point calculation unit 189 calculates a measurement point located at a position where the reliability of the measurement result becomes higher than in a case where a measurement point is set at a position designated by a user. Information of the calculated measurement point is held in the RAM 14. The position of the measurement point is associated with a specific image, and thus the measurement point is set.

The measurement point calculation unit 189 may be constituted by at least one of a processor and a logic circuit. The measurement point calculation unit 189 can include one or a plurality of processors. The measurement point calculation unit 189 can include one or a plurality of logic circuits.

Regarding points other than those stated above, the configuration shown in FIG. 9 is the same as the configuration shown in FIG. 3.

Figure 10A:
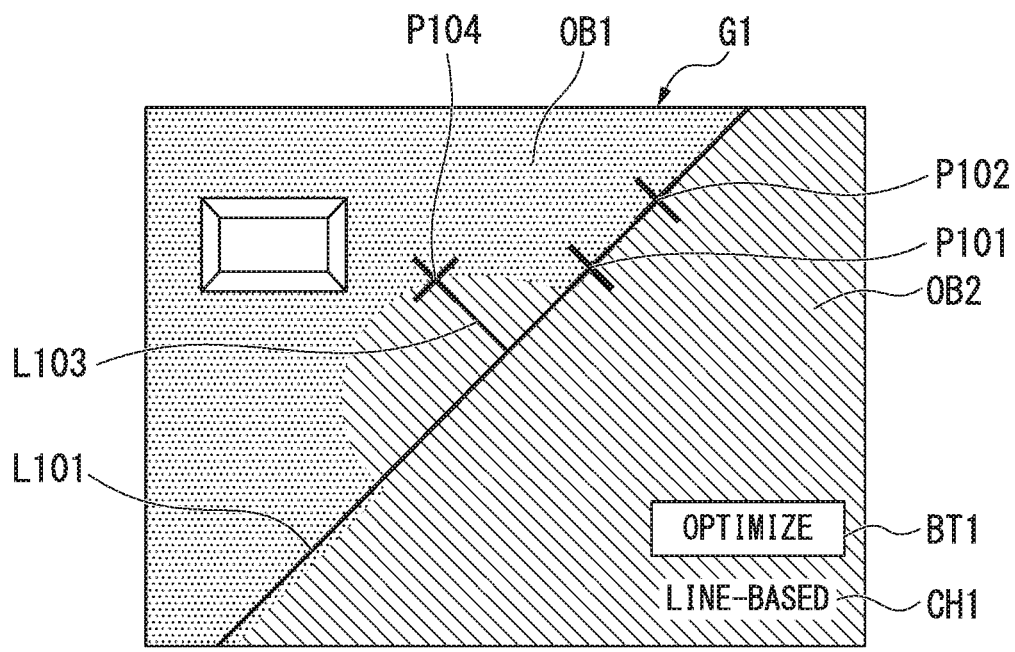
FIGS. 10A and 10B are diagrams showing an example of an image displayed on a display unit according to the modification example of the first embodiment of the present invention.

FIG. 10A shows an example of an image displayed on the display unit 5 after two reference designation points and one measurement designation point are designated. The first reference designation point P101, the second reference designation point P102, and a measurement designation point P104 are displayed on the image G1. The two-dimensional first reference line L101 and a two-dimensional first auxiliary line L103 are displayed on the image G1. In FIG. 10A, the measurement designation point P104 is a point on the edge of the image. However, the position of the measurement designation point P104 is not a deepest position in a loss (concave portion) of the subject OB1. The button BT1 is displayed on the image G1. When the button BT1 is pressed, an instruction for the optimization of a reference point is input.

Figure 10B:
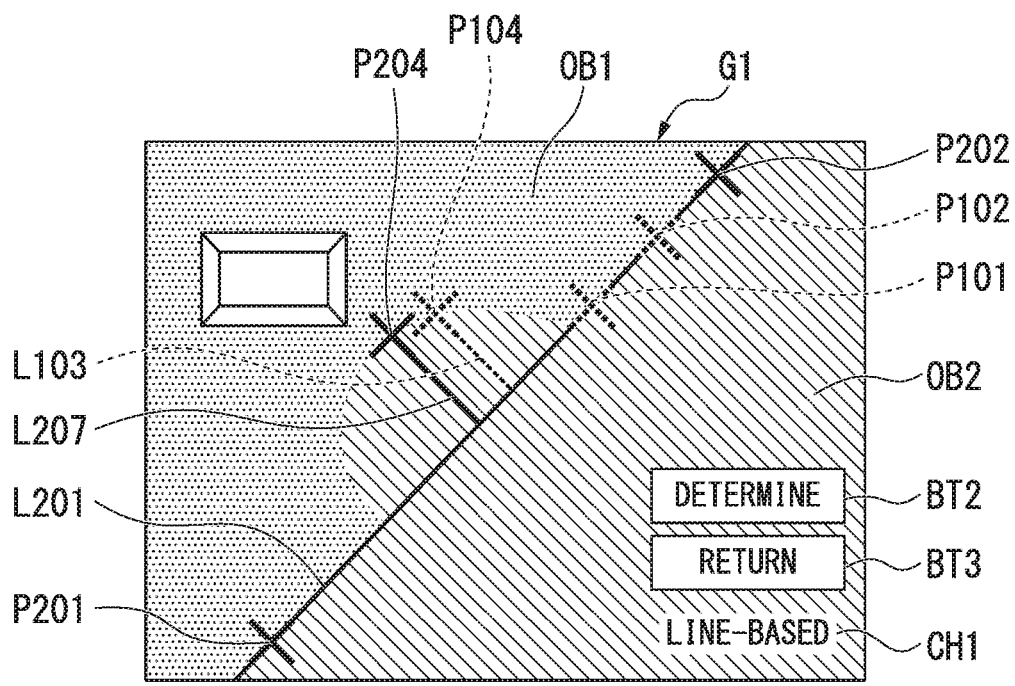

FIG. 10B shows an example of an image displayed on the display unit 5 when the button BT1 shown in FIG. 10A is pressed. The first reference point P201 and the second the reference point P202 are calculated, and the first reference point P201 and the second the reference point P202 are displayed on the image G1. The two-dimensional second reference line L201 is displayed on the image G1. After two reference points are calculated, the measurement point calculation unit 189 calculates a measurement point P204 on the basis of the second reference line L201. In the example shown in FIG. 10B, the measurement point calculation unit 189 calculates a point farthest from the second reference line L201 at the edge on the image G1, and sets the point to the measurement point P204. Since the measurement point P204 is a deepest position in a loss on the subject OB1, the reliability of the result of the line-based measurement increases. A two-dimensional second auxiliary line L207 is displayed on the image G1.

As described above, the measurement point calculation unit 189 calculates a measurement point. A measurement point at a position having a tendency to be high in the reliability of the measurement result is calculated. A user does not need to accurately designate the position (second position) of the measurement designation point. Therefore, the endoscope device 1 can simplify a user's designation of the measurement point, and improve the reliability of the measurement result.

Second Embodiment

An endoscope device 1 according to a second embodiment of the present invention has a plane-based measurement function. In the second embodiment, three reference designation points and one measurement designation point are designated by a user. Three reference points at which a measurement result having high reliability is obtained are calculated on the basis of three reference designation points. The measurement point is set at the position of the measurement designation point.

Figure 11:
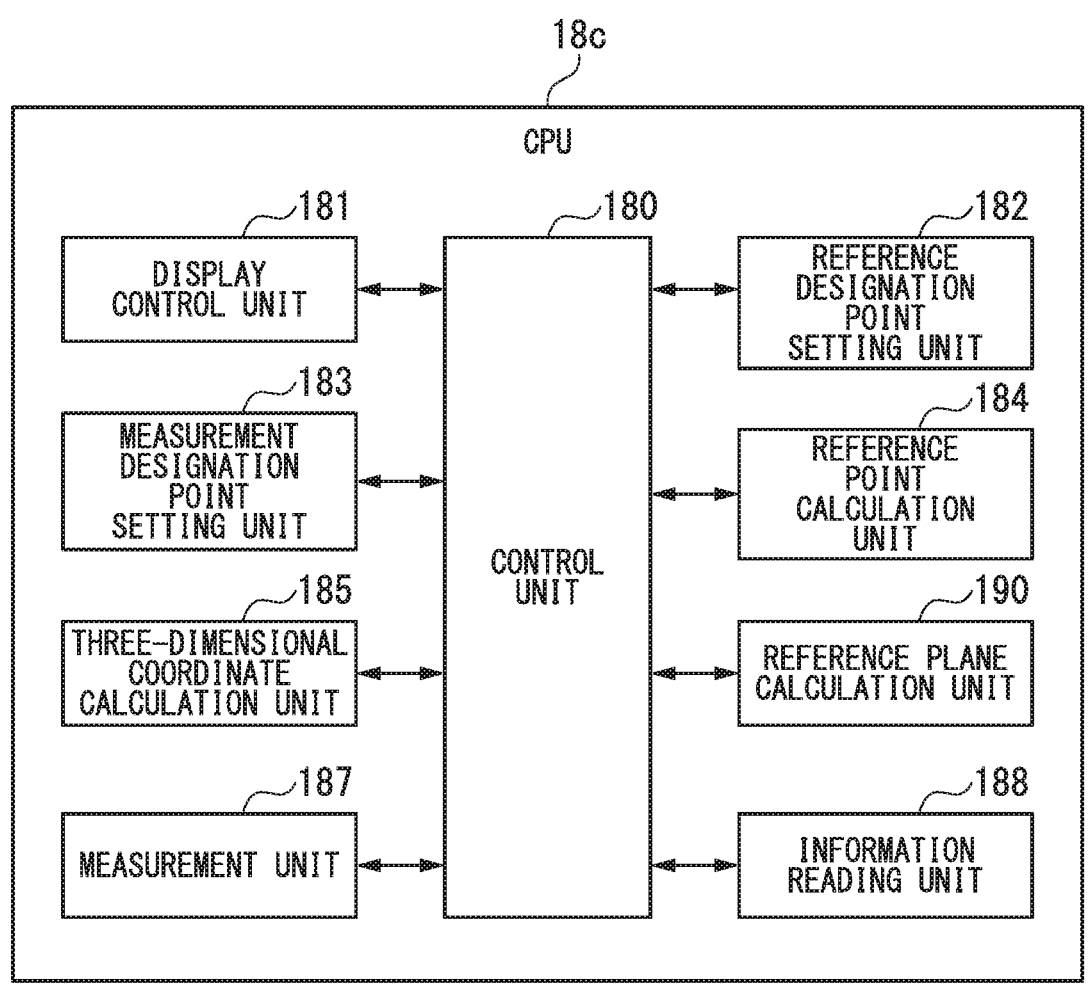
FIG. 11 is a block diagram showing a functional configuration of a CPU according to a second embodiment of the present invention.

In the second embodiment, the CPU 18*a* in the first embodiment is changed to a CPU 18*c* shown in FIG. 11. FIG. 11 shows a functional configuration of the CPU 18*c*. Regarding a configuration shown in FIG. 11, points different from those of the configuration shown in FIG. 3 will be described.

The CPU 18*c* includes a reference plane calculation unit 190 instead of the reference line calculation unit 186 shown in FIG. 3. As described later, the reference plane calculation unit 190 (reference calculation unit) calculates a reference plane on the basis of the plurality of reference designation points set by the reference designation point setting unit 182. The reference plane is used in the measurement mode indicated by the measurement mode information. The reference point calculation unit 184 calculates a plurality of reference points leading to higher reliability of a measurement result instead of a plurality of reference designation points for calculating the reference plane. In the second embodiment, the reference designation point setting unit 182 sets three reference designation points. The reference point calculation unit 184 calculates a plurality of reference points leading to higher reliability of a measurement result instead of a plurality of reference designation points for calculating the reference plane. In the second embodiment, the reference point calculation unit 184 calculates three reference points on the basis of the three reference designation points set by the reference designation point setting unit 182. The measurement mode information in the second embodiment indicates the plane-based measurement.

The reference plane calculation unit 190 calculates a first reference plane on the basis of the three reference designation points set by the reference designation point setting unit 182. Specifically, the reference plane calculation unit 190 calculates a first reference plane, passing through the three-dimensional coordinates of each of the three reference designation points, which is a plane on a three-dimensional space. The first reference plane is a temporary reference plane based on the three reference designation points. The first reference plane is not necessarily used in the plane-based measurement.

The reference plane calculation unit 190 calculates a second reference plane on the basis of the three reference points calculated by the reference point calculation unit 184. Specifically, the reference plane calculation unit 190 calculates a second reference plane, passing through the three-dimensional coordinates of each of the three reference points, which is a plane on a three-dimensional space. The second reference plane is a reference plane used in the plane-based measurement. After the first reference plane is calculated on the basis of the plurality of reference designation points, the reference plane calculation unit 190 calculates a new second reference plane on the basis of the plurality of reference points.

The reference plane calculation unit 190 may be constituted by at least one of a processor and a logic circuit. The reference plane calculation unit 190 can include one or a plurality of processors. The reference plane calculation unit 190 can include one or a plurality of logic circuits.

The measurement unit 187 executes the measurement of a subject on the basis of the reference planes, the measurement point, and the measurement mode. Specifically, the measurement unit 187 executes the measurement of a subject in the measurement mode indicated by the measurement mode information, using the reference plane determined on the basis of the plurality of reference points calculated by the reference point calculation unit 184. In the second embodiment, the measurement unit 187 calculates a three-dimensional distance between the three-dimensional reference plane calculated by the reference plane calculation unit 190 and the three-dimensional coordinates of the measurement point set by the measurement designation point setting unit 183.

Regarding points other than those stated above, the configuration shown in FIG. 11 is the same as the configuration shown in FIG. 3.

Figure 12:
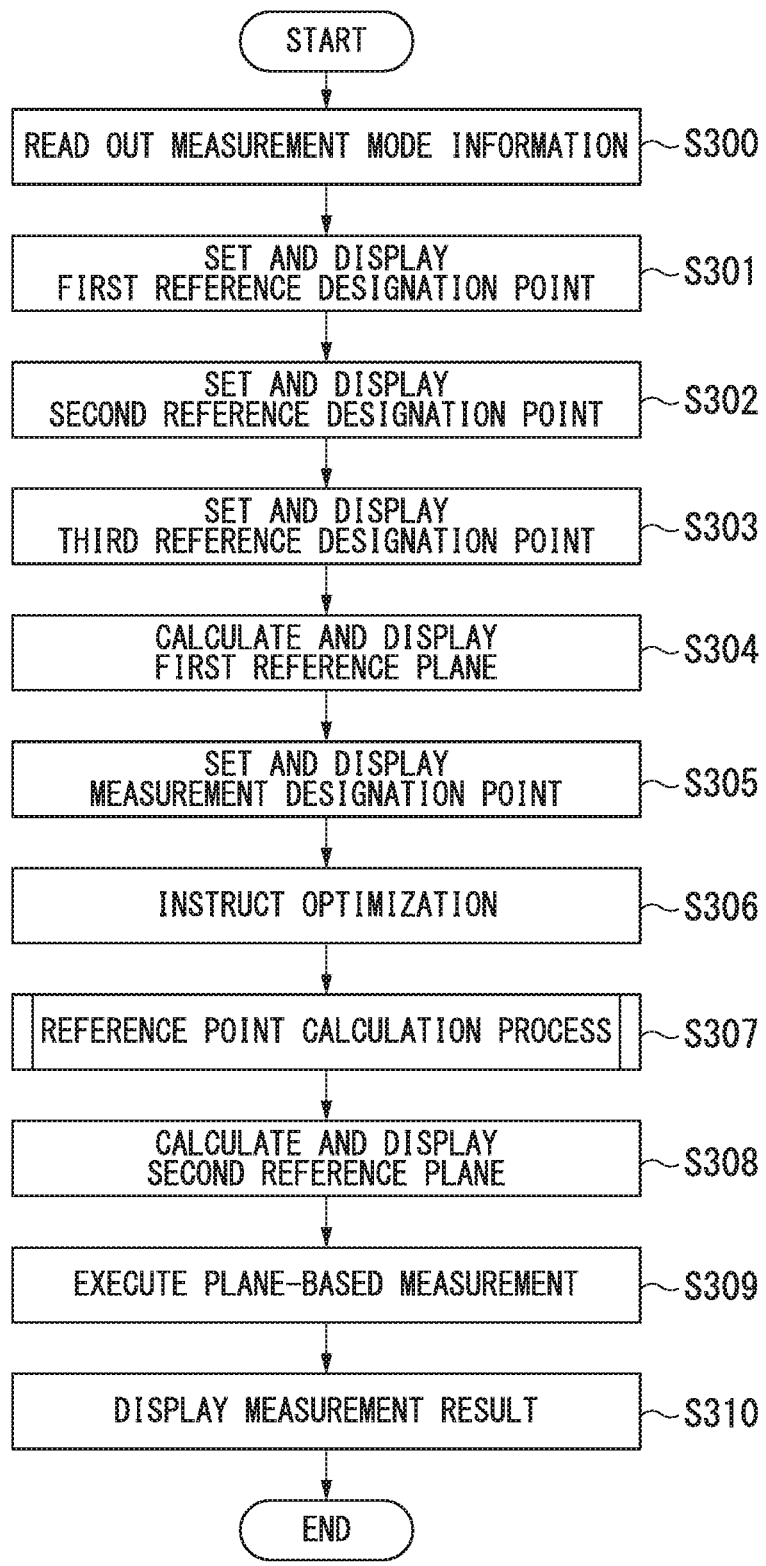
FIG. 12 is a flow diagram showing a procedure of three-dimensional measurement in the second embodiment of the present invention.

Three-dimensional measurement in the second embodiment will be described with reference to FIG. 12. FIG. 12 shows a procedure of the three-dimensional measurement.

As is the case with the first embodiment, the display unit 5 displays an image of a subject. A user can designate a reference designation point and a measurement designation point in the image of the subject by operating the operation unit 4.

The information reading unit 188 reads out the measurement mode information from the ROM 13 (step S300). The read-out measurement mode information indicates the plane-based measurement. Each unit of the CPU 18*c* executes a process specified in the plane-based measurement.

After step S300, the reference designation point setting unit 182 determines a position designated as the reference designation point by a user, on the basis of the operation result of the operation unit 4, and sets a first reference designation point at the position. The display control unit 181 displays the first reference designation point on the image (step S301).

After step S301, the reference designation point setting unit 182 determines a position designated as the reference designation point by a user, on the basis of the operation result of the operation unit 4, and sets a second reference designation point at the position. The display control unit 181 displays the second reference designation point on the image (step S302).

After step S302, the reference designation point setting unit 182 determines a position designated as the reference designation point by a user, on the basis of the operation result of the operation unit 4, and sets a third reference designation point at the position. The display control unit 181 displays the third reference designation point on the image (step S303).

After step S303, the display control unit 181 may cause the display unit 5 to display a first auxiliary line passing through three reference designation points.

After step S303, the three-dimensional coordinate calculation unit 185 calculates the three-dimensional coordinates of all pixels in the image. The reference plane calculation unit 190 calculates the first reference plane passing through the three-dimensional coordinates of each of the first reference designation point, the second reference designation point, and the third reference designation point. The reference plane calculation unit 190 determines whether a distance between each of a plurality of configuration points constituting the first reference plane and the three-dimensional coordinates of each pixel is smaller than a predetermined value, for each configuration point and for each pixel. The reference plane calculation unit 190 selects a pixel in which the distance becomes smaller than the predetermined value. Thereby, the reference plane calculation unit 190 selects a point close to the first reference plane among points on a subject. That is, the reference plane calculation unit 190 selects a point which is substantially coincident with a point on the first reference plane among points on the subject. The display control unit 181 causes the display unit 5 to display the pixel selected by the reference plane calculation unit 190 (step S304).

Meanwhile, a process of calculating the three-dimensional coordinates of all pixels in an image which is executed by the three-dimensional coordinate calculation unit 185 may be performed before step S300, and may be performed simultaneously with processes in steps S300 to S303 during a period in which the processes are executed.

For example, in step S304, the pixel selected by the reference plane calculation unit 190 is displayed in a predetermined color. Thereby, a region which is coincident with the surface of a subject in the first reference plane is displayed. A user can know the position of the first reference plane in a two-dimensional image.

After step S304, the measurement designation point setting unit 183 determines a position designated as a measurement designation point by a user on the basis of the operation result of the operation unit 4, and sets the measurement designation point at the position. The display control unit 181 displays the measurement designation point on the image (step S305). In the second embodiment, the measurement designation point is the same as a measurement point. Therefore, the measurement designation point set in step S305 is also handled as the measurement point.

After step S305, a user inputs an instruction for the optimization of a reference point by operating the operation unit 4. The operation unit 4 receives the instruction, and outputs information indicating the instruction. The information output from the operation unit 4 is input to the control interface 17. The information input to the control interface 17 is input to the CPU 18*c*. The control unit 180 detects the instruction for the optimization of a reference point (step S306).

After step S306, the reference point calculation process is executed (step S307). In the reference point calculation process, the reference point calculation unit 184 calculates a first reference point, a second reference point, and a third reference point at which the reliability of a measurement result becomes higher than in a case where measurement based on the first reference designation point, the second reference designation point, and the third reference designation point is executed. The details of the reference point calculation process will be described later.

After step S307, the display control unit 181 may cause the display unit 5 to display a second auxiliary line passing through three reference points.

After step S307, the reference plane calculation unit 190 calculates the second reference plane passing through the three-dimensional coordinates of each of the first reference point, the second reference point, and the third reference point. The reference plane calculation unit 190 determines whether a distance between each of a plurality of configuration points constituting the second reference plane and the three-dimensional coordinates of each pixel is smaller than a predetermined value, for each configuration point and for each pixel. The reference plane calculation unit 190 selects a pixel in which the distance becomes smaller than the predetermined value. Thereby, the reference plane calculation unit 190 selects a point close to the second reference plane among points on a subject. That is, the reference plane calculation unit 190 selects a point which is substantially coincident with a point on the second reference plane among points on the subject. The display control unit 181 causes the display unit 5 to display the pixel selected by the reference plane calculation unit 190 (step S308).

For example, in step S308, the pixel selected by the reference plane calculation unit 190 is displayed in a predetermined color. Thereby, a region which is coincident with the surface of the subject in the second reference plane is displayed. A user can know the position of the second reference plane in a two-dimensional image.

After step S308, the measurement unit 187 executes the plane-based measurement. That is, the measurement unit 187 calculates a three-dimensional distance between the second reference plane calculated in step S308 and the three-dimensional coordinates of a measurement point (step S309).

After step S309, the display control unit 181 causes the display unit 5 to display a measurement result. That is, the display control unit 181 causes the display unit 5 to display the three-dimensional distance calculated in step S309 (step S310). The process in step S310 is executed, and thus the three-dimensional measurement is terminated.

In the above example, the first reference point, the second reference point, and the third reference point are calculated on the basis of the first reference designation point, the second reference designation point, and the third reference designation point. Any one or two of the first reference designation point, the second reference designation point, and the third reference designation point may be set to the reference point. Other two or one reference point may be calculated through the same process as the above process on the basis of the first reference designation point, the second reference designation point, and the third reference designation point.

Any one of three reference designation points and the first reference plane may be displayed. Any one of three reference points and the second reference plane may be displayed. The display of the reference designation point and the measurement designation point is not essential. The display of the reference point and the measurement point is not essential. The display of the first reference plane and the second reference plane is not essential. The display of the measurement result is not essential.

The reference designation point setting unit 182 may set four or more reference designation points. The reference point calculation unit 184 may calculate four or more reference points.

Figure 13A:
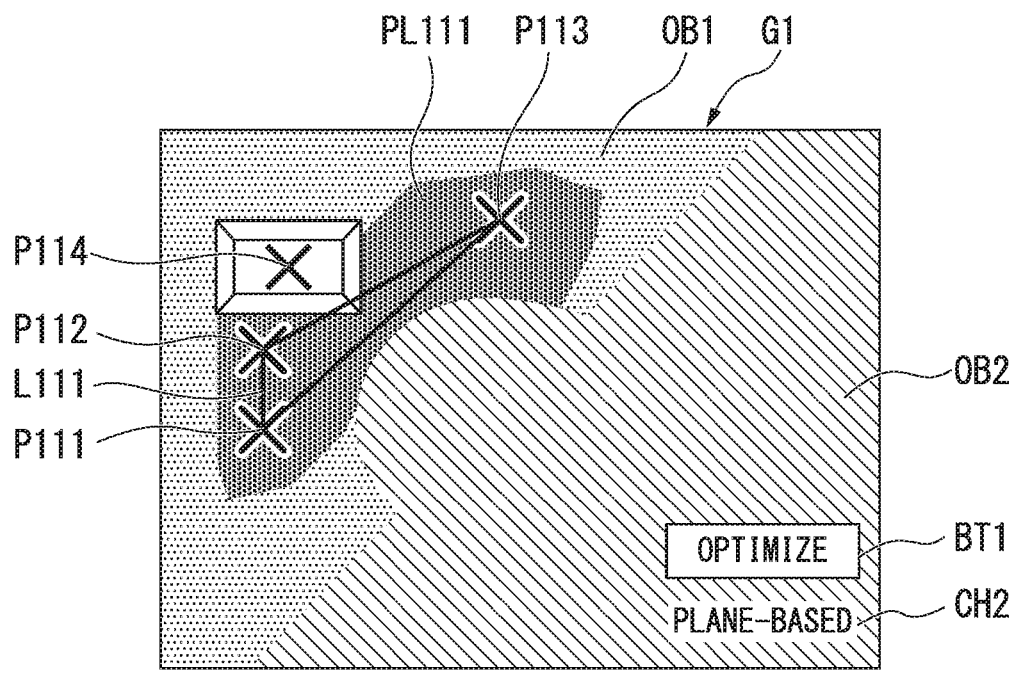
FIGS. 13A and 13B are diagrams showing an example of an image displayed on a display unit according to the second embodiment of the present invention.

FIG. 13A shows an example of an image displayed on the display unit 5. As shown in FIG. 13A, an image G1 is displayed. The image G1 includes images of a subject OB1 and a subject OB2. Character CH2 indicating a measurement mode are displayed on the image G1. The characters CH2 indicate that the measurement mode is plane-based measurement. The image G1 after a measurement designation point is designated in step S305 is shown in FIG. 13A.

In step S301, a first reference designation point P111 is set on the subject OB1. In step S302, a second reference designation point P112 is set on the subject OBE In step S303, a third reference designation point P113 is set on the subject OBE The first reference designation point P111, the second reference designation point P112, and the third reference designation point P113 are displayed on the image G1. A first auxiliary line L111 connecting the three reference designation points in order is displayed on the image G1. In step S304, the first reference plane is calculated. A region PL111 which is coincident with the surface of the subject OB1 in the first reference plane is displayed on the image G1. In step S305, a measurement designation point P114 is set on the subject OB1. The measurement designation point P114 is displayed on the image G1.

A button BT1 is displayed on the image G1. When the button BT1 is pressed, an instruction for the optimization of a reference point is input in step S306.

Figure 13B:
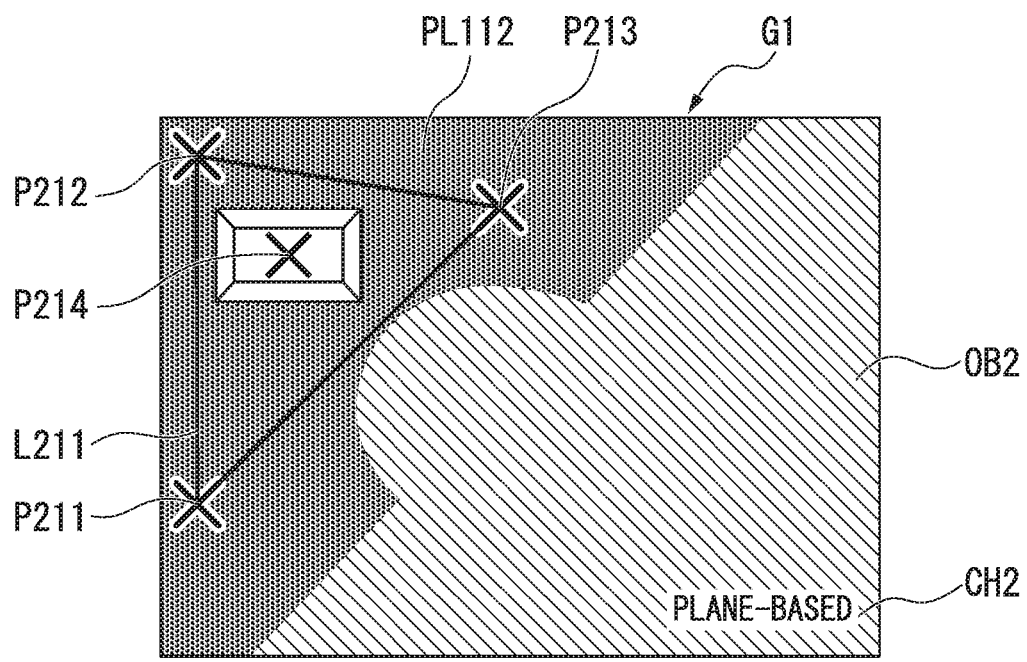

FIG. 13B shows an example of an image displayed on the display unit 5 when the button BT1 shown in FIG. 13A is pressed. In step S307, a first reference point P211, a second reference point P212, and a third reference point P213 are calculated. The first reference point P211, the second reference point P212, and the third reference point P213 are displayed on the image G1. A second auxiliary line L211 connecting the three reference points in order is displayed on the image G1. The display control unit 181 may cause the display unit 5 to display the first reference designation point P111, the second reference designation point P112, and the third reference designation point P113, together with the first reference point P211, the second reference point P212, and the third reference point P213. The reference points and the reference designation points are displayed, and thus a user can confirm whether the position of a reference point intended by the user and the position of an estimated reference point are coincident with each other.

A measurement point P214 is displayed at the same position as that of the measurement designation point P114. In step S308, the second reference plane is calculated. A region PL112 which is coincident with the surface of the subject OB1 in the second reference plane is displayed on the image G1.

In the example shown in FIG. 13B, the area of a triangle constituted by the three reference points is larger than the area of a triangle constituted by the three reference designation points shown in FIG. 13A. Therefore, the region PL112 shown in FIG. 13B is larger than the region PL111 shown in FIG. 13A. That is, the second reference plane is better coincident with the surface of the subject OB1 than the first reference plane. The measurement designation point P114 shown in FIG. 13A is set outside the triangle constituted by the three reference designation points, but the measurement point P214 shown in FIG. 13B is set inside the triangle constituted by the three reference points. As described above, it can be expected that a measurement result having high reliability is obtained.

As shown in FIG. 13B, the display control unit 181 causes the display unit 5 to display the plurality of reference points calculated by the reference point calculation unit 184 on the image. As shown in FIG. 13B, the display control unit 181 causes the display unit 5 to display the second reference plane determined on the basis of the plurality of reference points calculated by the reference point calculation unit 184 on the image.

As shown in FIG. 13A and FIG. 13B, the display control unit 181 causes the display unit 5 to display the plurality of reference points calculated by the reference point calculation unit 184 and the plurality of reference designation points set by the reference designation point setting unit 182, on the image. The reference points and the reference designation points may be displayed simultaneously.

As shown in FIG. 13A and FIG. 13B, the display control unit 181 causes the display unit 5 to display the second reference plane and the first reference plane on the image. The second reference plane is determined on the basis of the plurality of reference points calculated by the reference point calculation unit 184. The first reference plane is determined on the basis of the plurality of reference designation points set by the reference designation point setting unit 182. The second reference plane and the first reference plane may be displayed simultaneously.

Figure 14:
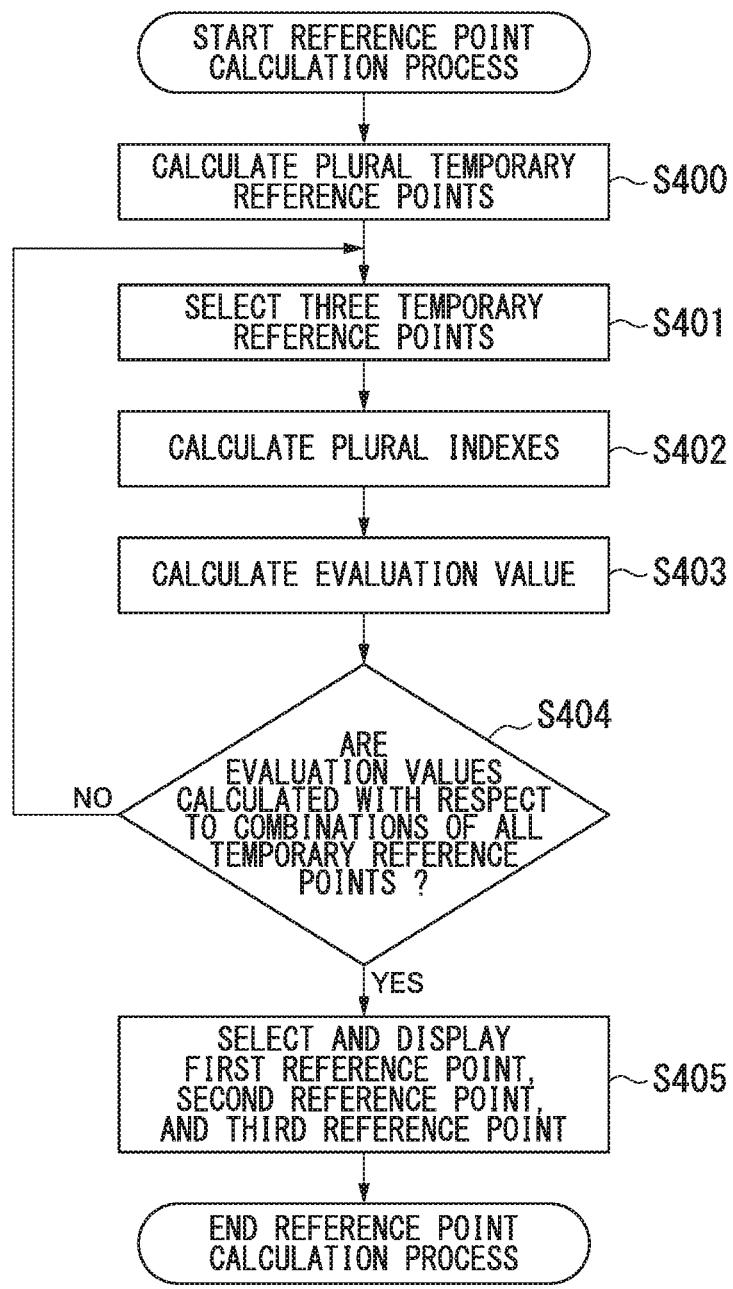
FIG. 14 is a flow diagram showing a procedure of a reference point calculation process in the second embodiment of the present invention.

FIG. 14 shows a procedure of the reference point calculation process in step S307. The details of the reference point calculation process will be described with reference to FIG. 14.

The reference point calculation unit 184 calculates a plurality of temporary reference points on the basis of a region which is coincident with the surface of a subject in the first reference plane calculated in step S304 (step S400). In step S400, four or more temporary reference points are calculated. Information of the calculated temporary reference points is held in the RAM 14.

The details of the process in step S400 will be described. For the efficiency of arithmetic operation, it is assumed that an optimum reference point is present in the vicinity of the region which is coincident with the surface of a subject and the region is included in the first reference plane calculated in step S304. For example, the reference point calculation unit 184 extracts a predetermined number of temporary reference points from the region. Alternatively, the reference point calculation unit 184 extracts a predetermined number of temporary reference points in a range within predetermined pixels from the boundary of the region. Points extracted as the temporary reference points are limited, and thus the amount of arithmetic operation is drastically reduced.

After step S400, the reference point calculation unit 184 selects three temporary reference points from a plurality of temporary reference points (step S401). The process in step S401 is executed multiple times. In a first process, any three temporary reference points are selected. A combination of three temporary reference points selected in an N-th process is different from a combination of three temporary reference points selected in the first to (N−1)-th processes. N is an integer equal to or greater than 2.

After step S401, the reference point calculation unit 184 calculates a plurality of indexes (step S402).

The details of the process in step S402 will be described. In the following example, the reference point calculation unit 184 calculates an index A, an index B, and an index C. The index A indicates the size of the area of a triangle constituted by the three temporary reference points. The index B relates to a positional relationship between the three temporary reference points and the measurement designation point. The index B indicates the magnitude of the distance between the intersection point of a perpendicular line from the measurement designation point to a reference plane with the reference plane and the centroid of the three temporary reference points. The intersection point of a perpendicular line from the measurement designation point to a reference plane with the reference plane is a point closest to the measurement designation point on the reference plane. The perpendicular line from the measurement designation point to the reference plane is a straight line that passes through the measurement designation point and is perpendicular to the reference plane. The index C indicates the number of pixels corresponding to three-dimensional coordinates which are present in the vicinity of the reference plane among three-dimensional coordinates on a subject. Each of the indexes is normalized so as to be set between 0 and 1. The measurement mode information includes information of indexes calculated in the reference point calculation process. That is, the indexes calculated in the reference point calculation process are specified by the measurement mode information.

The reference point calculation unit 184 calculates a reference plane used in the calculation of each index, on the basis of the three temporary reference points selected in step S401. The reference plane calculation unit 190 may calculate a reference plane used in the calculation of each index.

The reference point calculation unit 184 calculates the index A on the basis of Expression (7). In Expression (7), S is the area of a triangle constituted by three temporary reference points. In Expression (7), W is the transverse size of an image, and H is the longitudinal size of the image. In Expression (7), the coordinates of the three temporary reference points are $(x_1, y_1)$, $(x_2, y_2)$, and $(x_3, y_3)$, respectively. As the area of the triangle constituted by the three temporary reference points increases, the index A increases.

$$A = \frac{S}{WH} \quad (7)$$

The reference point calculation unit 184 calculates the index B on the basis of Expression (8), Expression (9), and Expression (10). D in Expression (8) and Expression (9) is represented by Expression (10). In Expression (10), the coordinates of the three temporary reference points are $(x_1, y_1)$, $(x_2, y_2)$, and $(x_3, y_3)$, respectively. In Expression (10), the coordinates of the intersection point of a perpendicular line from the measurement designation point to a three-dimensional reference plane with the reference plane is $(x_C, y_C)$.

$$\text{When } \frac{D}{L_a} < 1 \quad B = 1 - \frac{D}{L_a} \quad (8)$$

$$\text{When } \frac{D}{L_a} \geq 1 \quad B = 0 \quad (9)$$

$$D = \sqrt{\left(x_c - \frac{x_1 + x_2 + x_3}{3}\right)^2 + \left(y_c - \frac{y_1 + y_2 + y_3}{3}\right)^2} \quad (10)$$

$L_a$ in Expression (8) and Expression (9) is represented by Expression (11). In Expression (11), $L_a$ is the average of $L_1$, $L_2$, and $L_3$. In Expression (11), $L_1$ is a distance between a first temporary reference point and a second temporary reference point. In Expression (11), $L_2$ is a distance between the second temporary reference point and a third temporary reference point. In Expression (11), $L_3$ is a distance between the third temporary reference point and the first temporary reference point. As the distance between the intersection point of a perpendicular line from the measurement designation point to the three-dimensional reference plane with the reference plane and the centroid of the three temporary reference points decreases, the index B increases.

$$L_a = \frac{L_1 + L_2 + L_3}{3} \quad (11)$$

The reference point calculation unit 184 calculates the index C on the basis of Expression (12). In Expression (12), $N_A$ is the number of regions when the reference plane is divided into regions having a fixed interval. In Expression (12), $N_B$ is the number of regular hexahedrons including three-dimensional points on a subject among minute regular hexahedrons each disposed at the center of the divided region. As the degree of coincidence of the reference plane with the surface of a subject becomes higher, the index C increases.

$$C = \frac{N_B}{N_A} \quad (12)$$

Figure 15A:
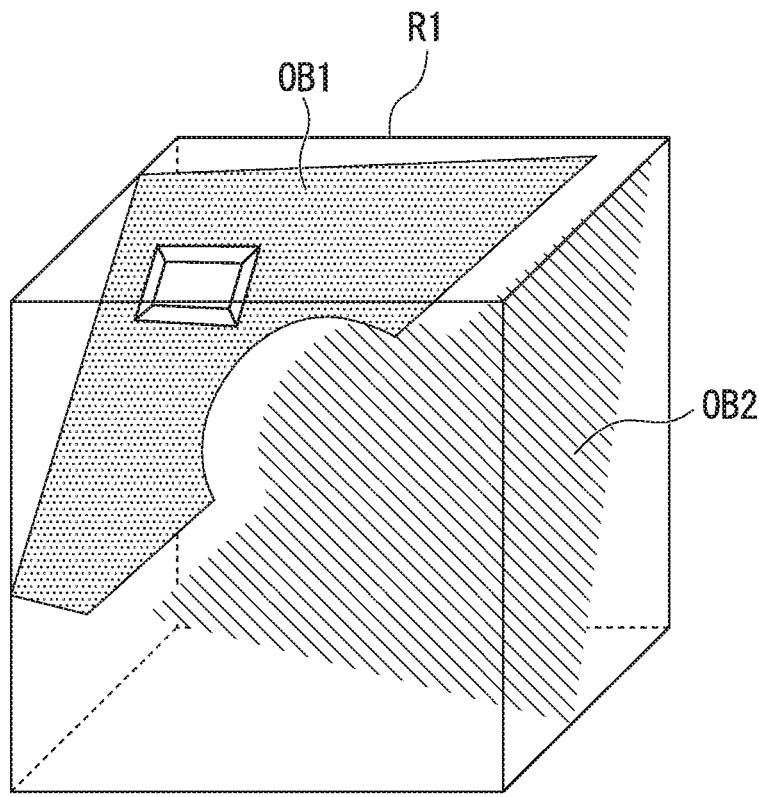
FIGS. 15A and 15B are diagrams showing a method of calculating indexes in the second embodiment of the present invention.

A detailed calculation method of the index C will be described. The three-dimensional coordinates of all pixels in the image calculated by the three-dimensional coordinate calculation unit 185 in step S304 is used. The three-dimensional coordinate calculation unit 185 may calculate the three-dimensional coordinates of all pixels again in step S402. A rectangular parallelepiped R1 shown in FIG. 15A includes the three-dimensional coordinates of all pixels. The rectangular parallelepiped R1 includes three-dimensional coordinates corresponding to points on the surface of the subject OB1 and three-dimensional coordinates corresponding to points on the surface of the subject OB2. The maximum value of the X-coordinates of points constituting the rectangular parallelepiped R1 is the same as the maximum value of X-coordinates constituting the three-dimensional coordinates of all pixels. The minimum value of the X-coordinates of the points constituting the rectangular parallelepiped R1 is the same as the minimum value X-coordinates constituting the three-dimensional coordinates of all pixels. A relationship between Y-coordinates of the points constituting the rectangular parallelepiped R1 and Y-coordinates constituting the three-dimensional coordinates of all pixels is the same as the relationship as to the X-coordinate. A relationship between the Z-coordinates of the points constituting the rectangular parallelepiped R1 and Z-coordinates constituting the three-dimensional coordinates of all pixels is the same as the relationship as to the X-coordinate.

Figure 15B:
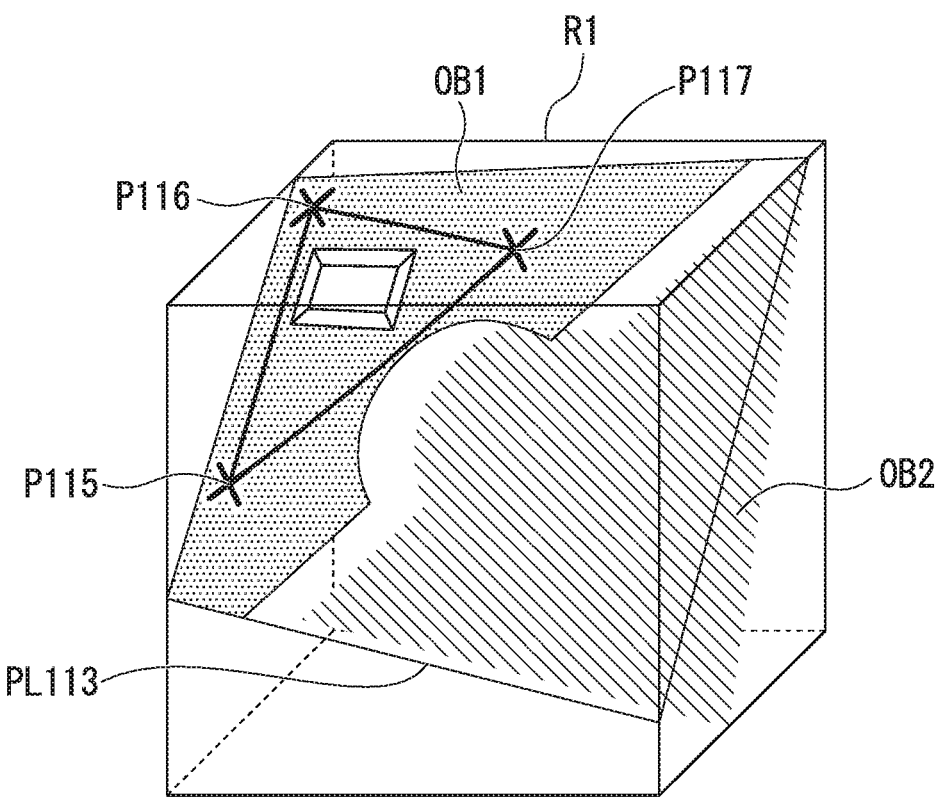

As shown in FIG. 15B, a temporary reference point P115, a temporary reference point P116, and a temporary reference point P117 are selected in step S401. In step S402, the reference point calculation unit 184 calculates a reference plane PL113 passing through the temporary reference point P115, the temporary reference point P116, and the temporary reference point P117.

Figure 16:
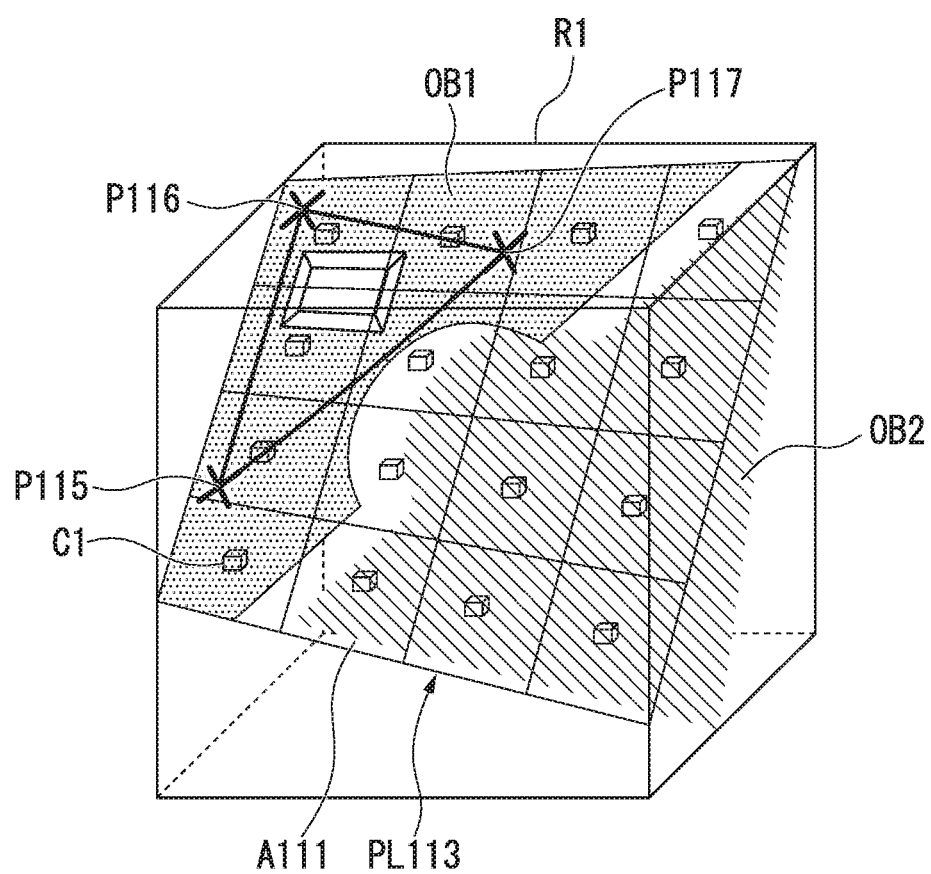
FIG. 16 is a diagram showing a method of calculating indexes in the second embodiment of the present invention.

As shown in FIG. 16, the reference point calculation unit 184 divides the reference plane PL113 into a plurality of regions A111. The number of regions A111 is $N_A$ in Expression (12). The number of regions A111 is shown to be small for the purpose of simplifying the illustration, but more regions A111 than the regions A111 shown in FIG. 16 are set in reality. The reference point calculation unit 184 disposes minute regular hexahedrons Cl within the respective regions A111. The reference point calculation unit 184 counts the number of regular hexahedrons Cl including three-dimensional points on the subject OB1 or the subject OB2 among all of the regular hexahedrons Cl. The counted number of regular hexahedrons Cl is $N_B$ in Expression (12).

Figure 17A:
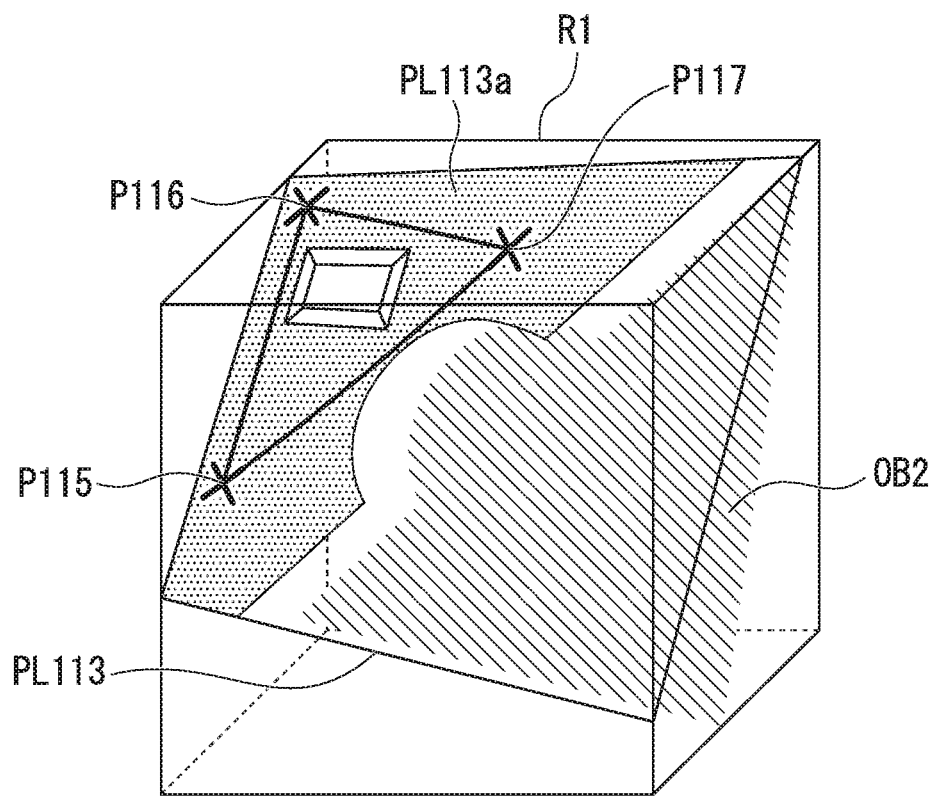
FIGS. 17A and 17B are diagrams showing calculation results for reference planes in the second embodiment of the present invention.
Figure 17B:
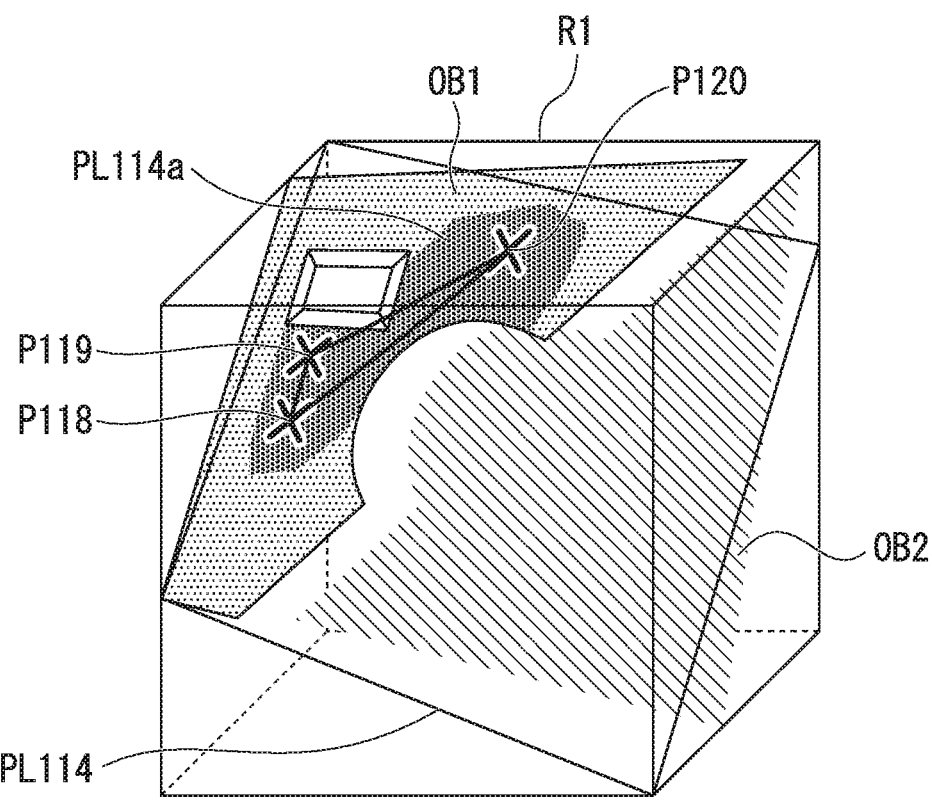

FIGS. 17A and 17B show calculation results for two different reference planes. As shown in FIG. 17A, the reference plane PL113 passing through the temporary reference point P115, the temporary reference point P116, and the temporary reference point P117 is calculated. A region PL113a indicates a region of the reference plane PL113 in which three-dimensional points on the subject OB1 and the subject OB2 are included in a minute regular hexahedron. As shown in FIG. 17B, a reference plane PL114 passing through a temporary reference point P118, a temporary reference point P119, and a temporary reference point P120 is calculated. A region PL114a indicates a region of the reference plane PL114 in which three-dimensional points on the subject OB1 and the subject OB2 are included in a minute regular hexahedron.

The region PL113a shown in FIG. 17A is wider than the region PL114a shown in FIG. 17B. That is, the reference plane PL113 shown in FIG. 17A is better coincident with the surface of the subject OB1 than the reference plane PL114.

After step S402, the reference point calculation unit 184 calculates an evaluation value by calculating the sum of a plurality of indexes (step S403). For example, in step S403, the reference point calculation unit 184 calculates the sum of the index A, the index B, and the index C. The reference point calculation unit 184 may calculate the product of three indexes. The reference point calculation unit 184 may multiply coefficients for weighting with respect to each index, and take the sum thereof.

After step S403, the reference point calculation unit 184 determines whether evaluation values are calculated with respect to the combinations of all the temporary reference points (step S404).

In step S404, in a case where the reference point calculation unit 184 determines that there is a combination of three temporary reference points for which an evaluation value is not calculated, the process in step S401 is executed. In that case, the combination of three temporary reference points is changed, and a plurality of indexes and the evaluation value are calculated for each combination of temporary reference points.

In step S404, in a case where the reference point calculation unit 184 determines that evaluation values are calculated with respect to the combinations of all the temporary reference points, the reference point calculation unit 184 selects a combination of three temporary reference points having the maximum evaluation value. Thereby, the reference point calculation unit 184 selects the first reference point, the second reference point, and the third reference point. The selected three temporary reference points are the first reference point, the second reference point, and the third reference point, respectively. The display control unit 181 displays the first reference point, the second reference point, and the third reference point on the image (step S405). The process in step S405 is executed, and thus the reference point calculation process is terminated.

In the reference point calculation process shown in FIG. 14, the reference point calculation unit 184 calculates at least one reference point included in the plurality of reference points such that a position of the at least one reference point satisfies a criterion according to the characteristics of a measurement mode indicated by the measurement mode information.

In step S400, the reference point calculation unit 184 sets a plurality of temporary reference points in the image displayed on the display unit 5. The positions of the plurality of temporary reference points are different from each other. In the second embodiment, at least four temporary reference points are set. In step S401, the reference point calculation unit 184 selects a combination including at least three temporary reference points. In steps S402 and S403, for each combination of temporary reference points, the reference point calculation unit 184 calculates an evaluation value indicating a degree to which at least three temporary reference points included in the combination is suitable for a criterion. In a case where the degree of suitability indicated by the evaluation value of a first combination is higher than the degree of suitability indicated by the evaluation value of a second combination, in step S405, the reference point calculation unit 184 sets at least one of at least three temporary reference points included in the first combination to the reference point.

In step S402, for each combination of temporary reference points, the reference point calculation unit 184 calculates a plurality of indexes different from each other for each of a plurality of criteria, on the basis of the positions of at least three temporary reference points included in the combination. In step S403, the reference point calculation unit 184 calculates an evaluation value, for each combination of temporary reference points, on the basis of the plurality of indexes.

In the reference point calculation process, the reference point calculation unit 184 calculates a plurality of reference points such that distances between the plurality of reference points become larger. The reference point calculation unit 184 calculates a plurality of reference points such that the distances between the plurality of reference points become larger than distances between a plurality of reference designation points. For example, the minimum value of the distances between the plurality of reference points is larger than the minimum value of the distances between the plurality of reference designation points, and the maximum value of the distances between the plurality of reference points is larger than the maximum value of the distances between the plurality of reference designation points. The average of the distances between the plurality of reference points may be larger than the average of the distances between the plurality of reference designation points. The reference point calculation unit 184 calculates a plurality of reference points that satisfy the above conditions, on the basis of the evaluation value in which the index A is reflected.

The reference point calculation unit 184 calculates at least three reference points such that the area of a polygon with vertices at the at least three reference points becomes larger. The reference point calculation unit 184 calculates at least three reference points such that a first area becomes larger than a second area. The first area is an area of a polygon with vertices at the at least three reference points. The second area is an area of a polygon with vertices at the at least three reference designation points. The reference point calculation unit 184 calculates at least three reference points that satisfy such conditions, on the basis of the evaluation value in which the index A is reflected.

In the reference point calculation process, the reference point calculation unit 184 calculates a plurality of reference points such that the intersection point of a perpendicular line from the measurement point or the measurement designation point to a reference plane with the reference plane comes close to the centroid of the plurality of reference points. The reference point calculation unit 184 calculates a plurality of reference points such that a first distance becomes smaller than a second distance. The first distance is a distance between the intersection point of a perpendicular line from the measurement point or the measurement designation point to the second reference plane with the reference plane and the centroid of a plurality of reference points. The second distance is a distance between the intersection point of a perpendicular line from the measurement point or the measurement designation point to the first reference plane with the reference plane and the centroid of a plurality of reference designation points. The reference point calculation unit 184 calculates a plurality of reference points that satisfy the above conditions, on the basis of the evaluation value in which the index B is reflected.

The reference point calculation unit 184 calculates a plurality of reference points such that a degree to which a reference plane approximates the surface of a subject becomes higher. The reference point calculation unit 184 calculates a plurality of reference points such that a first degree becomes higher than a second degree. The first degree is a degree to which the second reference plane determined on the basis of a plurality of reference points approximates the surface of a subject. The second degree is a degree to which the first reference plane determined on the basis of a plurality of reference designation points approximates the surface of the subject. The reference point calculation unit 184 calculates a plurality of reference points that satisfy the above conditions, on the basis of the evaluation value in which the index C is reflected.

Even in a case where a user who does not have a full understanding of the principle of measurement, the measurement mode and the like performs measurement, the reference point calculation process is executed, and thus an optimum reference point for the plane-based measurement mode is set.

A method of obtaining the optimum reference point position may be a method of repeatedly performing optimization using, for example, a Levenberg-Marquardt method. The type of algorithm for calculating an optimum reference point does not matter.

Figure 18A:
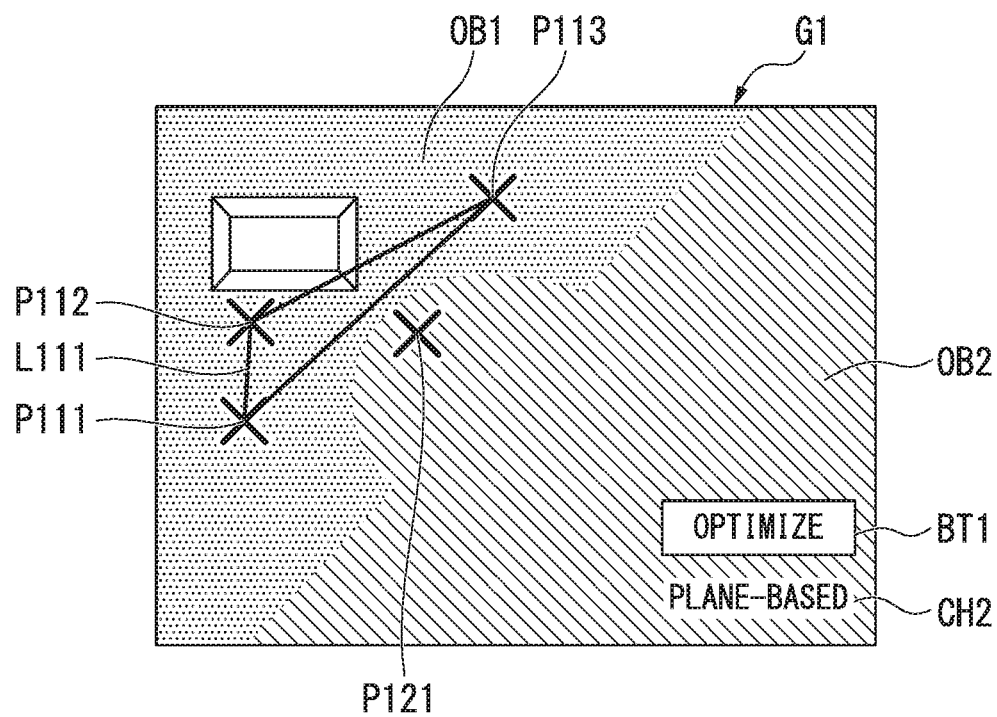
FIGS. 18A and 18B are diagrams showing an example of an image displayed on the display unit according to the second embodiment of the present invention.

FIG. 18A shows an example of an image displayed on the display unit 5 when the measurement designation point is set at a position different from the position of the measurement designation point P114 shown in FIG. 13A. A first reference designation point P111, a second reference designation point P112, and a third reference designation point P113 are the same as the first reference designation point P111, the second reference designation point P112, and the third reference designation point P113 shown in FIG. 13A, respectively. A measurement designation point P121 is set on the subject OB2. A button BT1 is displayed on the image G1.

Figure 18B:
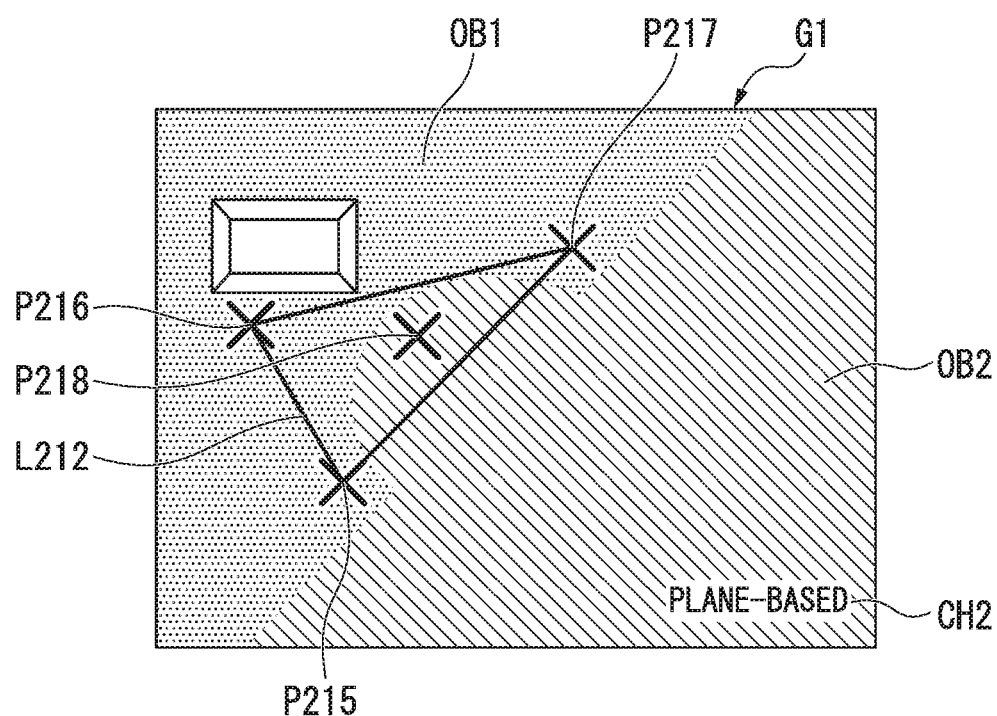

FIG. 18B shows an example of an image displayed on the display unit 5 when the button BT1 shown in FIG. 18A is pressed. A first reference point P215, a second reference point P216, and a third reference point P217 are calculated. The first reference point P215, the second reference point P216, and the third reference point P217 are displayed on the image G1. A second auxiliary line L212 connecting the three reference points in order is displayed on the image G1. A measurement point P218 is displayed at the same position as that of the measurement designation point P121. The second reference plane is calculated. A region which is coincident with the surface of the subject OB1 in the second reference plane is displayed on the image G1. In FIG. 18B, the display of the region is omitted. Since the position of the measurement designation point P121 shown in FIG. 18A and the position of the measurement designation point P114 shown in FIG. 13A are different from each other, the positions of three reference points shown in FIG. 18B are different from the positions of three reference points shown in FIG. 13B.

After the second reference plane is calculated in step S308 shown in FIG. 12, similarly to FIGS. 17A and 17B, the display control unit 181 may cause the display unit 5 to display a region of the second reference plane in which three-dimensional points on a subject are included in a minute regular hexahedron. Thereby, a user can confirm whether the second reference plane is well coincident with the surface of a subject.

After step S308, a user may determine whether the first reference point, the second reference point, and the third reference point are adopted as formal reference points. For example, in a case where the button BT2 shown in FIG. 5B is displayed and the button BT2 is pressed, the process in step S309 may be executed. Alternatively, in a case where the button BT3 shown in FIG. 5B is displayed and the button BT3 is pressed, the process in step S301 may be executed.

Other indexes excluding the index A, the index B, and the index C may be used. For example, an index related to a distance between a reference designation point designated by a user and a temporary reference point may be used. As the distance decreases, the index increases. An index related to the correlation value of matching at a temporary reference point may be used. As the correlation value increases, the index increases.

An index related to the strength of texture at a temporary reference point may be used. As the texture becomes stronger, the index increases. An index related to a variation in coordinates in the vicinity of the reference point among the three-dimensional coordinates of pixels may be used. As the variation decreases, the index increases. An index related to whether three reference points are located on the same object may be used. In a case where the three reference points are located on the same object, the index is large. Indexes other than these indexes may be used. One or two of the index A, the index B, and the index C and other indexes may be used. Only one or two of the index A, the index B, and the index C may be used.

Even in a case where a user is not able to determine an optimum reference point just through the appearance of an image, the reference point calculation unit 184 can easily calculate the optimum reference point by combining the above indexes.

When other candidates of three reference points are calculated, the reference point calculation unit 184 can calculate candidates of three reference points having characteristics different from the characteristics of the three reference points calculated previously, through the introduction of a new index or the change of weighting of each index.

The display control unit 181 may cause the display unit 5 to display information for assisting a user's selection of reference points. For example, the display control unit 181 may cause the display unit 5 to display the value of each index used in the calculation of reference points. Alternatively, the display control unit 181 may cause the display unit 5 to display the degree of weighting of each index used in the calculation of reference points. Alternatively, the display control unit 181 may cause the display unit 5 to display a message indicating that a reference plane passing through the calculated reference point is well coincident with the surface of a subject.

After step S305 shown in FIG. 12, the process in step S307 may be executed. That is, the process in step S306 may be omitted.

In the three-dimensional measurement shown in FIG. 12, the endoscope device 1 can obtain an optimum measurement result when a user just designates the reference designation points. The first reference point, the second reference point, and the third reference point calculated on the basis of the three reference designation points do not need to be displayed. In this case, a user does not need to confirm the reference point.

After the reference point and the measurement point are displayed, a user may be able to freely correct the positions of the reference point and the measurement point. Thereby, a user can refer to the positions of the reference point and the measurement point presented by the endoscope device 1, and finely adjust these positions. Therefore, a measurement result at a position intentionally designated by a user is obtained.

Figure 19:
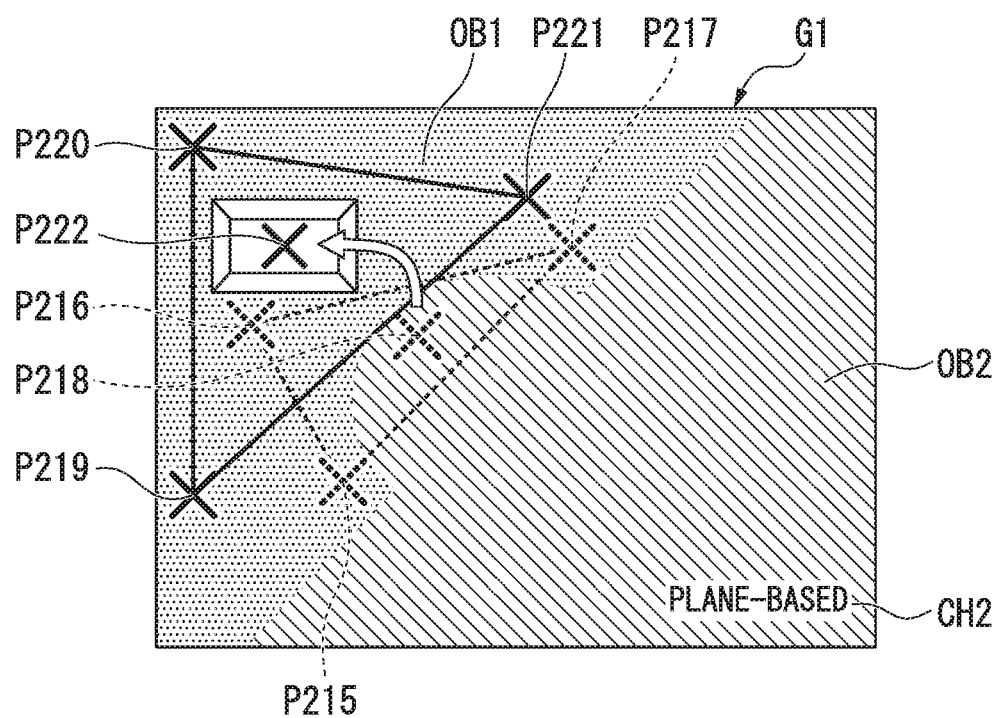
FIG. 19 is a diagram showing an example of an image displayed on the display unit according to the second embodiment of the present invention.

FIG. 19 shows an example in which three reference points are calculated and then the position of the measurement point is changed by a user's instruction. After the first reference point P215, the second reference point P216, the third reference point P217, and the measurement point P218 shown in FIG. 18B are displayed, a user moves the measurement point P218 by operating the operation unit 4. Thereby, a new measurement point P222 is set. The reference point calculation unit 184 calculates a first reference point P219, a second reference point P220, and a third reference point P221 on the basis of the measurement point P222.

For example, when the measurement point P218 is changed to the measurement point P222, the reference point calculation unit 184 calculates a plurality of temporary reference points located around the measurement point P222. Thereafter, the reference point calculation unit 184 calculates the first reference point P219, the second reference point P220, and the third reference point P221 by executing the processes in steps S401 to S405 shown in FIG. 14.

In the above example, three reference points are calculated, but four or more reference points may be calculated, and the reference plane may be calculated on the basis of these reference points. Thereby, the probability of the reference plane rises. In the above example, the reference plane is a plane, but the reference plane may be a curved surface.

As described above, the reference point calculation unit 184 calculates a plurality of reference points on the basis of the measurement mode indicated by the measurement mode information. A reference point at a position having a tendency to be high in the reliability of the measurement result is calculated. A user does not need to accurately designate the position (first position) of the reference designation point. Therefore, the endoscope device 1 can simplify a user's designation of the reference point, and improve the reliability of the measurement result.

A user does not need to accurately designate points in units of sub-pixels as in the related art. Therefore, the endoscope device 1 can drastically reduce the burden of a user's operation due to an input particularly using a touch panel or the like. Even in a case where a user who has no knowledge pertaining to a three-dimensional measurement function operates the endoscope device 1, the endoscope device 1 can obtain a measurement result having high reliability.

As described above, a reference point automatically calculated by the endoscope device 1 is displayed. Thereby, a user can confirm whether the reference point is suitable for measurement.

Third Embodiment

An endoscope device 1 according to a third embodiment of the present invention has a line-based measurement function. The third embodiment will be described using the CPU 18a shown in FIG. 3.

In the third embodiment, the reference designation point setting unit 182 sets two reference designation points on the basis of one position (first position) designated on an image by a user.

Figure 20:
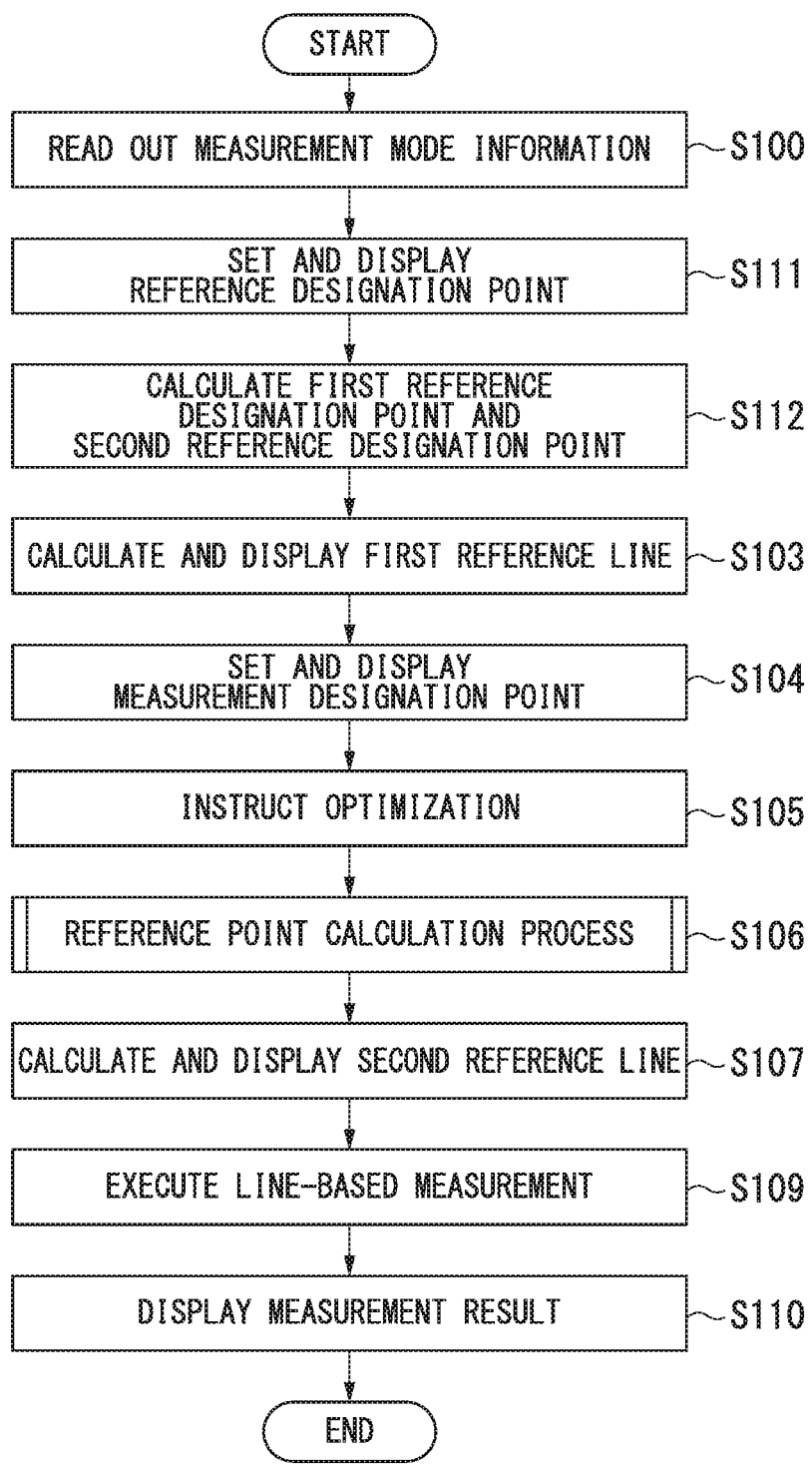
FIG. 20 is a flow diagram showing a procedure of three-dimensional measurement in a third embodiment of the present invention.

Three-dimensional measurement in the third embodiment will be described with reference to FIG. 20. FIG. 20 shows a procedure of the three-dimensional measurement. Regarding a process shown in FIG. 20, points different from those of the process shown in FIG. 4 will be described.

After step S100, the reference designation point setting unit 182 determines a position designated as the reference designation point by a user, on the basis of the operation result of the operation unit 4, and sets a reference designation point at the position. The display control unit 181 displays the reference designation point on the image (step S111).

After step S111, the reference designation point setting unit 182 calculates a first reference designation point and a second reference designation point on the basis of the reference designation point (step S112). After step S112, the process in step S103 is executed. After step S107, the process in step S109 is executed.

Regarding points other than those stated above, the process shown in FIG. 20 is the same as the process shown in FIG. 4.

Figure 21A:
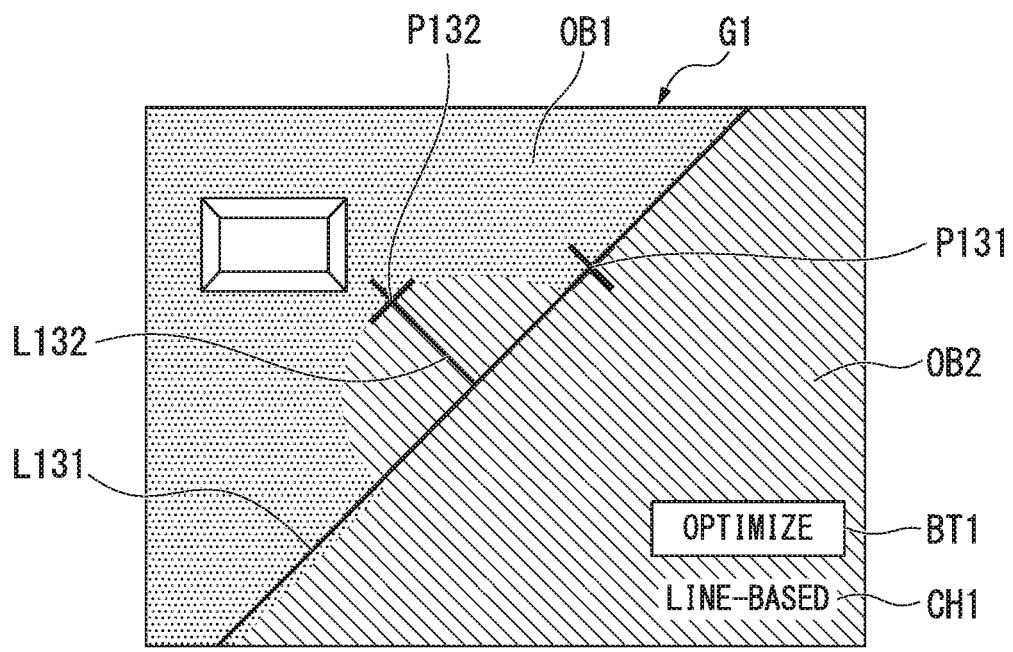
FIGS. 21A and 21B are diagrams showing an example of an image displayed on a display unit according to the third embodiment of the present invention.

FIG. 21A shows an example of an image displayed on the display unit 5. As shown in FIG. 21A, an image G1 including images of a subject OB1 and a subject OB2 is displayed. Characters CH1 indicating line-based measurement are displayed on the image G1. The image G1 after the measurement designation point is designated in step S104 is shown in FIG. 21A.

In step S111, a reference designation point P131 on the edge of the subject OB1 is set. In step S112, the reference designation point setting unit 182 searches for an edge in the vicinity of the reference designation point P131. For example, the reference designation point setting unit 182 detects an edge in an image in a predetermined range centering on the reference designation point P131. The reference designation point setting unit 182 sets the first reference designation point and the second reference designation point at any positions on the detected edge. The first reference designation point and the second reference designation point are not displayed on the display unit 5.

In step S103, the first reference line is calculated. A two-dimensional first reference line L131 is displayed on the image G1. In the example shown in FIG. 21A, the first reference line L131 is not coincident with the edge of the subject OB1. In step S104, a measurement designation point P132 on the edge of the subject OB1 is set. The measurement designation point P132 and a two-dimensional first auxiliary line L132 are displayed on the image G1.

A button BT1 is displayed on the image G1. When the button BT1 is pressed, an instruction for the optimization of a reference point is input in step S105.

Figure 21B:
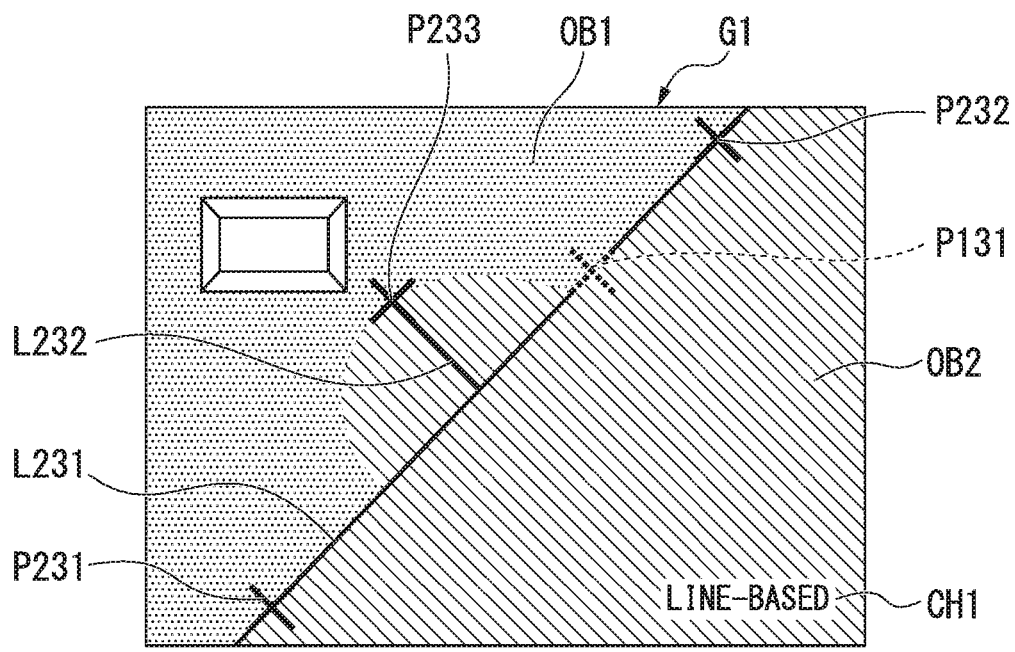

FIG. 21B shows an example of an image displayed on the display unit 5 when the button BT1 shown in FIG. 21A is pressed. In step S106, a first reference point P231 and a second reference point P232 are calculated. The first reference point P231 and the second reference point P232 are displayed on the image G1.

A measurement point P233 is displayed at the same position as that of the measurement designation point P132. In step S107, a second reference line is calculated. A two-dimensional second reference line L231 is displayed on the image G1. A two-dimensional second auxiliary line L232 is displayed on the image G1.

In the example shown in FIG. 21B, the second reference line L231 is well coincident with the edge of the subject OB1. Therefore, it can be expected that a measurement result having high reliability is obtained.

In a case where the reference designation point setting unit 182 is not able to detect an edge in the vicinity of the reference designation point designated by a user, the display control unit 181 may cause the display unit 5 to display a message indicating that an edge has not been detected.

The reference designation point designated by a user in step S111 may be set as the first reference designation point. In that case, the reference designation point setting unit 182 calculates the second reference designation point on the basis of the first reference designation point. In step S112, the display control unit 181 may cause the display unit 5 to display the first reference designation point and the second reference designation point.

After step S107, a user may determine whether the first reference point and the second reference point are adopted as formal reference points. For example, in a case where the button BT2 shown in FIG. 5B is displayed and the button BT2 is pressed, the process in step S109 may be executed. Alternatively, in a case where the button BT3 shown in FIG. 5B is displayed and the button BT3 is pressed, the process in step S111 may be executed.

After step S104, the process in step S106 may be executed. That is, the process in step S105 may be omitted.

The display control unit 181 may cause the display unit 5 to display the first reference designation point and the second reference designation point.

As described above, a user designates one reference designation point and one measurement designation point. Therefore, as compared with the first embodiment in which two reference designation points and one measurement designation point are required to be designated, it is possible to reduce the burden of a user's operation.

Fourth Embodiment

An endoscope device 1 according to a fourth embodiment of the present invention has a plane-based measurement function. The fourth embodiment will be described using the CPU 18c shown in FIG. 11.

In the fourth embodiment, the reference designation point setting unit 182 sets three reference designation points on the basis of one position (first position) designated on an image by a user.

Figure 22:
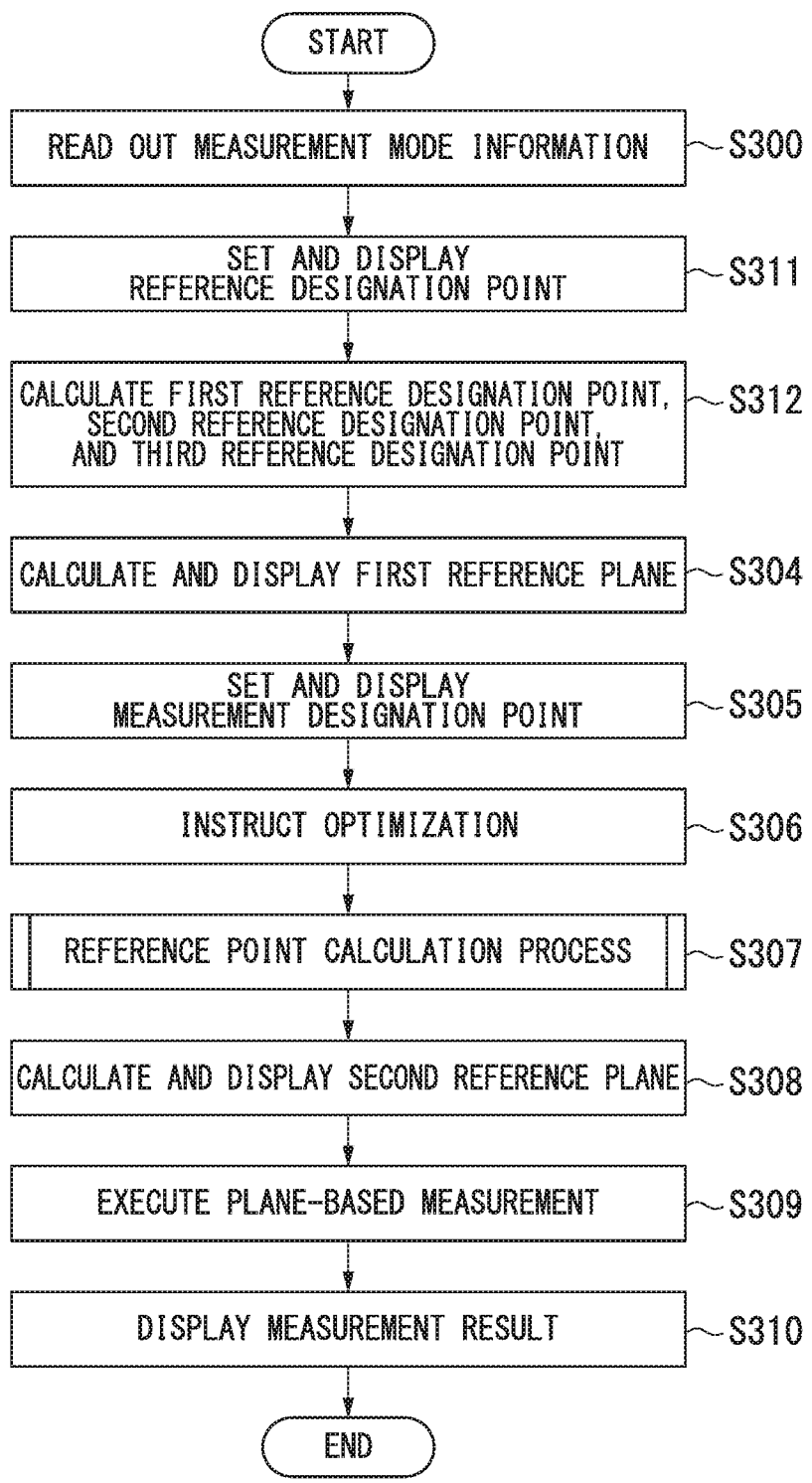
FIG. 22 is a flow diagram showing a procedure of three-dimensional measurement in a fourth embodiment of the present invention.

Three-dimensional measurement in the fourth embodiment will be described with reference to FIG. 22. FIG. 22 shows a procedure of the three-dimensional measurement. Regarding a process shown in FIG. 22, points different from those of the process shown in FIG. 12 will be described.

After step S300, the reference designation point setting unit 182 determines a position designated as the reference designation point by a user, on the basis of the operation result of the operation unit 4, and sets a reference designation point at the position. The display control unit 181 displays the reference designation point on the image (step S311).

After step S311, the reference designation point setting unit 182 calculates the first reference designation point, the second reference designation point, and the third reference designation point on the basis of the reference designation point (step S312). After step S312, the process in step S304 is executed.

Regarding points other than those stated above, the process shown in FIG. 22 is the same as the process shown in FIG. 12.

Figure 23A:
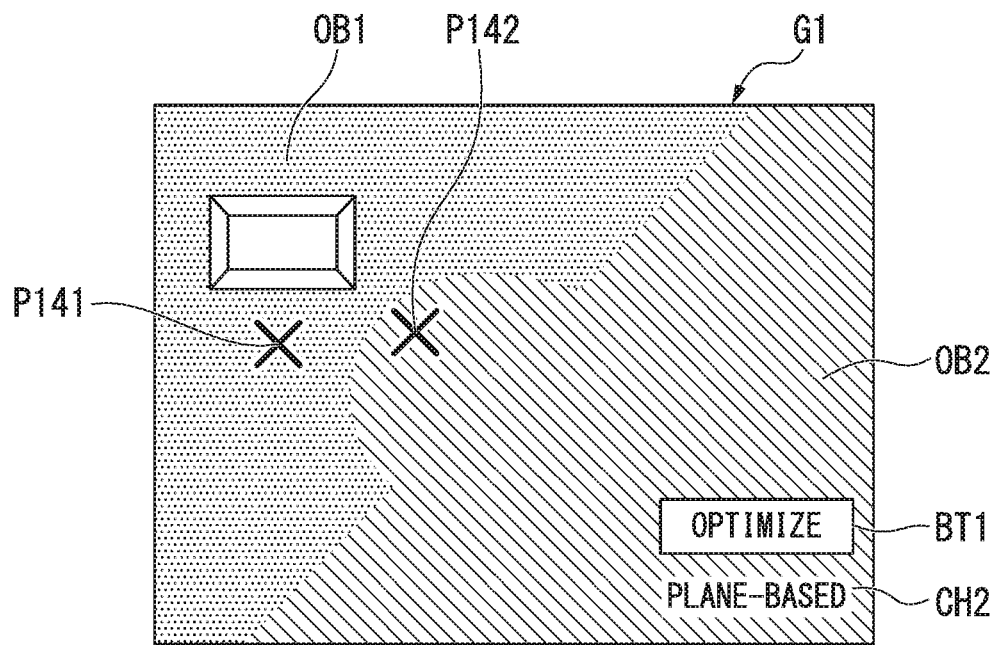
FIGS. 23A and 23B are diagrams showing an example of an image displayed on a display unit according to the fourth embodiment of the present invention.

FIG. 23A shows an example of an image displayed on the display unit 5. As shown in FIG. 23A, an image G1 including images of a subject OB1 and a subject OB2 is displayed. Character CH2 indicating plane-based measurement are displayed on the image G1. The image G1 after the measurement designation point is designated in step S305 is shown in FIG. 23A.

In step S311, a reference designation point P141 is set on the subject OB1. In step S312, the three-dimensional coordinate calculation unit 185 calculates the three-dimensional coordinates of a plurality of pixels in the vicinity of the reference designation point. The reference designation point setting unit 182 calculates a temporary reference plane passing through the three-dimensional coordinates of the plurality of pixels. The reference designation point setting unit 182 sets the first reference designation point, the second reference designation point, and the third reference designation point at any positions on the temporary reference plane. The first reference designation point, the second reference designation point, and the third reference designation point are not displayed on the display unit 5.

In step S304, a first reference plane is calculated. A region which is coincident with the surface of the subject OB1 in the first reference plane is displayed on the image G1. The display of the region is omitted in FIG. 23A. In step S305, a measurement designation point P142 is set on the subject OB2. The measurement designation point P142 is displayed on the image G1.

A button BT1 is displayed on the image G1. When the button BT1 is pressed, an instruction for the optimization of a reference point is input in step S306.

Figure 23B:
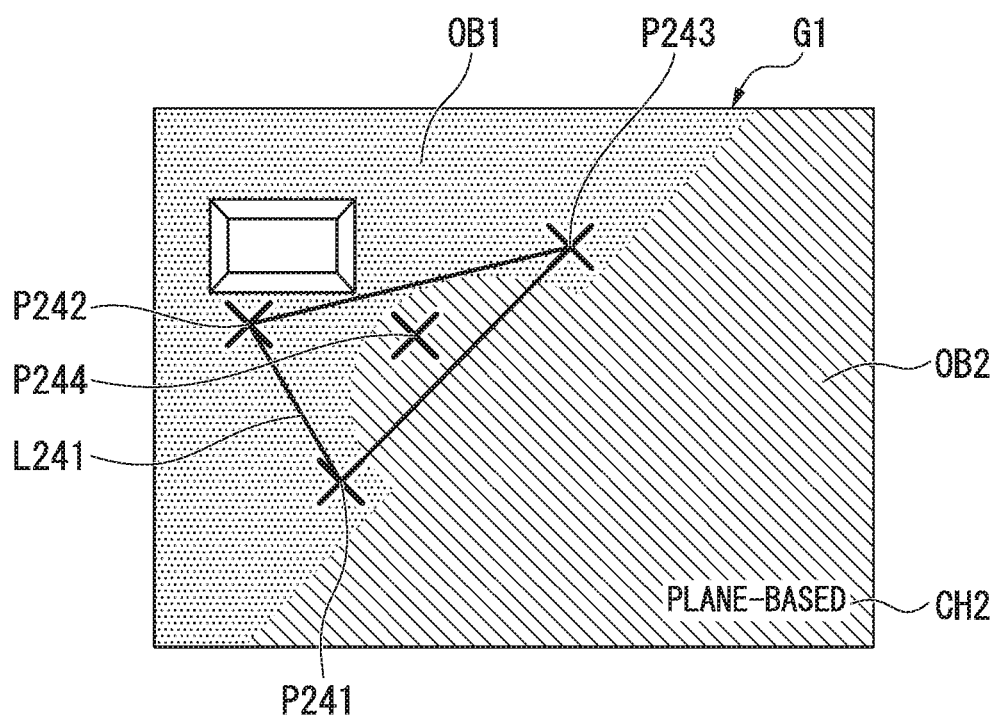

FIG. 23B shows an example of an image displayed on the display unit 5 when the button BT1 shown in FIG. 23A is pressed. In step S307, a first reference point P241, a second reference point 242, and a third reference point P243 are calculated. The first reference point P241, the second reference point 242, and the third reference point P243 are displayed on the image G1.

A measurement point P244 is displayed at the same position as that of the measurement designation point P142. In step S308, a second reference plane is calculated. A region which is coincident with the surface of the subject OB1 in the second reference plane is displayed on the image G1. The display of the region is omitted in FIG. 23B. A second auxiliary line L241 connecting three reference points in order is displayed on the image G1.

It may be difficult to calculate the temporary reference plane due to a large variation in the three-dimensional coordinates of a plurality of pixels in the vicinity of the reference designation point. In that case, the display control unit 181 may cause the display unit 5 to display a message indicating that the temporary reference plane is not able to be calculated.

The first reference designation point designated by a user in step S311 may be set as the reference designation point. In that case, the reference designation point setting unit 182 calculates the second reference designation point and the third reference designation point on the basis of the first reference designation point. In step S312, the display control unit 181 may cause the display unit 5 to display the first reference designation point, the second reference designation point, and the third reference designation point.

After step S308, a user may determine whether the first reference point, the second reference point, and the third reference point are adopted as formal reference points. For example, in a case where the button BT2 shown in FIG. 5B is displayed and the button BT2 is pressed, the process in step S309 may be executed. Alternatively, in a case where the button BT3 shown in FIG. 5B is displayed and the button BT3 is pressed, the process in step S311 may be executed.

After step S305, the process in step S307 may be executed. That is, the process in step S306 may be omitted.

The display control unit 181 may cause the display unit 5 to display the first reference designation point, the second reference designation point, and the third reference designation point.

As described above, a user designates one reference designation point and one measurement designation point. Therefore, as compared with the second embodiment in which three reference designation points and one measurement designation point are required to be designated, it is possible to reduce the burden of a user's operation.

Fifth Embodiment

An endoscope device 1 according to a fifth embodiment of the present invention has a line-based measurement function. The fifth embodiment will be described using the CPU 18a shown in FIG. 3.

In the fifth embodiment, the reference designation point setting unit 182 calculates two reference designation points on the basis of the measurement designation point set by the measurement designation point setting unit 183.

Figure 24:
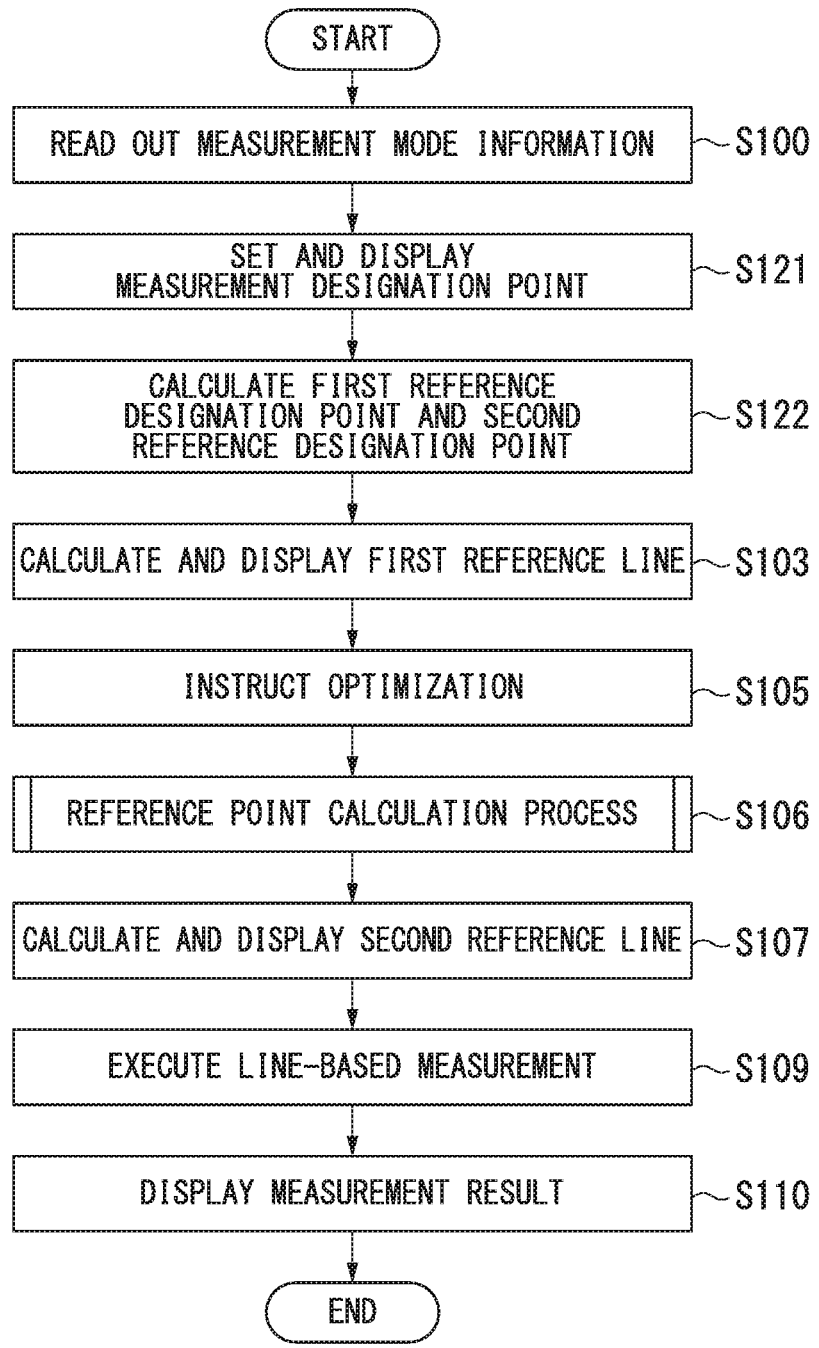
FIG. 24 is a flow diagram showing a procedure of three-dimensional measurement in a fifth embodiment of the present invention.

Three-dimensional measurement in the fifth embodiment will be described with reference to FIG. 24. FIG. 24 shows a procedure of the three-dimensional measurement. Regarding a process shown in FIG. 24, points different from those of the process shown in FIG. 4 will be described.

After step S100, the measurement designation point setting unit 183 determines a position designated as a measurement designation point by a user on the basis of the operation result of the operation unit 4, and sets the measurement designation point at the position. The display control unit 181 displays the measurement designation point on an image (step S121). In the fifth embodiment, the measurement designation point is the same as a measurement point. Therefore, the measurement designation point set in step S121 is also handled as the measurement point.

After step S121, the reference designation point setting unit 182 calculates the first reference designation point and the second reference designation point on the basis of the measurement designation point (step S122). After step S122, the process in step S103 is executed. After step S107, the process in step S109 is executed.

Regarding points other than those stated above, the process shown in FIG. 24 is the same as the process shown in FIG. 4.

Figure 25A:
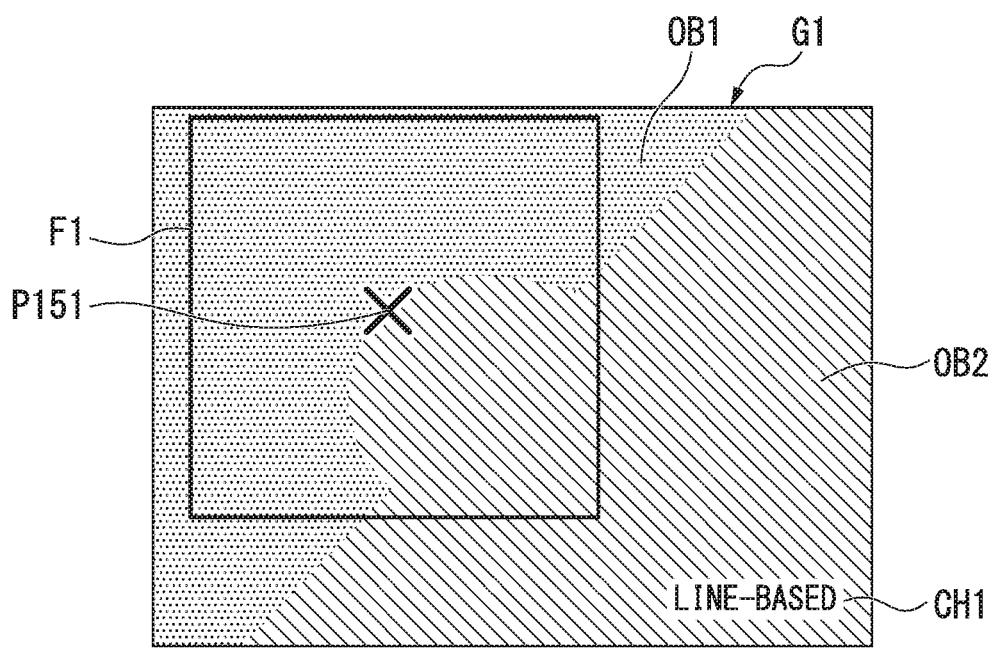
FIGS. 25A and 25B are diagrams showing an example of an image displayed on a display unit according to the fifth embodiment of the present invention.

FIG. 25A shows an example of an image displayed on the display unit 5. As shown in FIG. 25A, an image G1 including images of a subject OB1 and a subject OB2 is displayed. Characters CH1 indicating line-based measurement are displayed on the image G1. The image G1 after the measurement designation point is designated in step S121 is shown in FIG. 25A.

In step S121, a measurement designation point P151 on the edge of the subject OB1 is set. In step S122, the reference designation point setting unit 182 sets a frame F1 based on the measurement designation point P151. For example, a frame F1 centering on the measurement designation point P151 is set. For example, the frame F1 is square. The shape of the frame F1 is not limited thereto. The reference designation point setting unit 182 detects an edge within the frame F1.

Figure 25B:
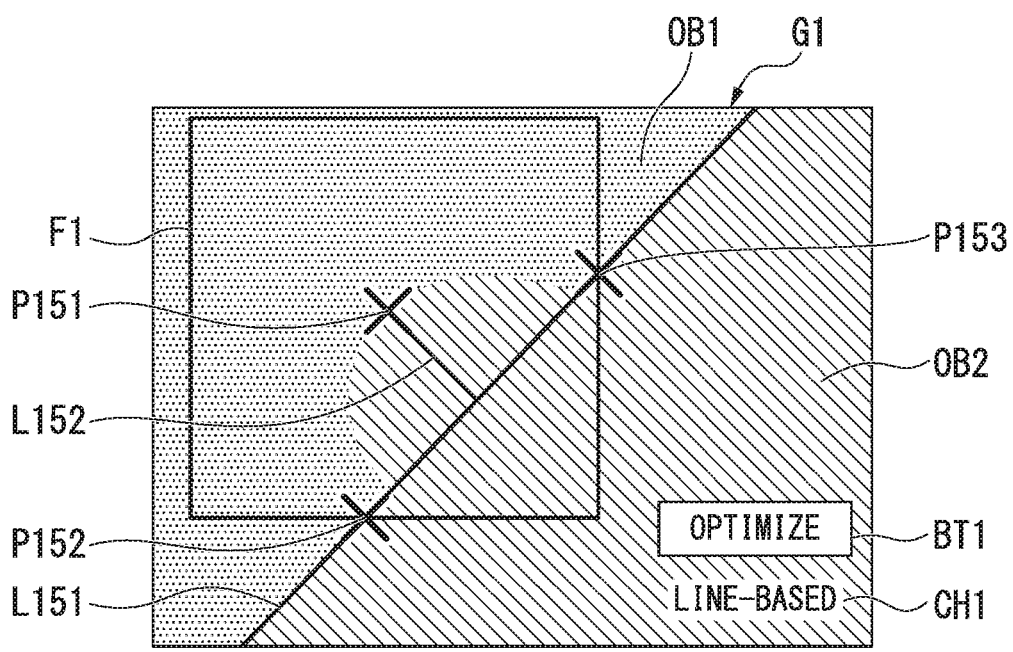

As shown in FIG. 25B, the reference designation point setting unit 182 sets a first reference designation point P152 and a second reference designation point P153 at the positions of two points of intersection between the detected edge and the frame F1. The first reference designation point P152 and the second reference designation point P153 are displayed on the image G1.

In step S103, a first reference line is calculated. A two-dimensional first reference line L151 and a two-dimensional first auxiliary line L152 are displayed on the image G1.

A button BT1 is displayed on the image G1. When the button BT1 is pressed, an instruction for the optimization of a reference point is input in step S105.

In a case where the reference designation point setting unit 182 is not able to detect an edge intersecting the frame F1, the display control unit 181 may cause the display unit 5 to display a message indicating that an edge has not been detected.

In step S122, the reference designation point setting unit 182 may detect a plurality of edges on a subject. The reference designation point setting unit 182 may set any two points on an edge close to the measurement designation point, among the detected edges, to the first reference designation point and the second reference designation point. The reference designation point setting unit 182 may set any two points on an edge connected to the measurement designation point, among the detected edges, to the first reference designation point and the second reference designation point.

After step S107, a user may determine whether the first reference point and the second reference point are adopted as formal reference points. For example, in a case where the button BT2 shown in FIG. 5B is displayed and the button BT2 is pressed, the process in step S109 may be executed. Alternatively, in a case where the button BT3 shown in FIG. 5B is displayed and the button BT3 is pressed, the process in step S121 may be executed.

After step S103, the process in step S106 may be executed. That is, the process in step S105 may be omitted.

As described above, a user designates one measurement designation point. Therefore, as compared with the first embodiment in which two reference designation points and one measurement designation point are required to be designated, it is possible to reduce the burden of a user's operation. In addition, as compared with the third embodiment in which one reference designation point and one measurement designation point are required to be designated, it is possible to reduce the burden of a user's operation.

Sixth Embodiment

An endoscope device 1 according to a sixth embodiment of the present invention has a plane-based measurement function. The sixth embodiment will be described using the CPU 18c shown in FIG. 11.

In the sixth embodiment, the reference designation point setting unit 182 calculates three reference designation points on the basis of the measurement designation point set by the measurement designation point setting unit 183.

Three-dimensional measurement in the sixth embodiment will be described with reference to FIG. 26. FIG. 26 shows a procedure of the three-dimensional measurement. Regarding a process shown in FIG. 26, points different from those of the process shown in FIG. 12 will be described.

After step S300, the measurement designation point setting unit 183 determines a position designated as a measurement designation point by a user on the basis of the operation result of the operation unit 4, and sets the measurement designation point at the position. The display control unit 181 displays the measurement designation point on an image (step S321). In the sixth embodiment, the measurement designation point is the same as a measurement point. Therefore, the measurement designation point set in step S321 is also handled as the measurement point.

After step S321, the reference designation point setting unit 182 calculates a first reference designation point, a second reference designation point, and a third reference designation point on the basis of the measurement designation point (step S322). After step S322, the process in step S304 is executed.

Regarding points other than those stated above, the process shown in FIG. 26 is the same as the process shown in FIG. 12.

Figure 27A:
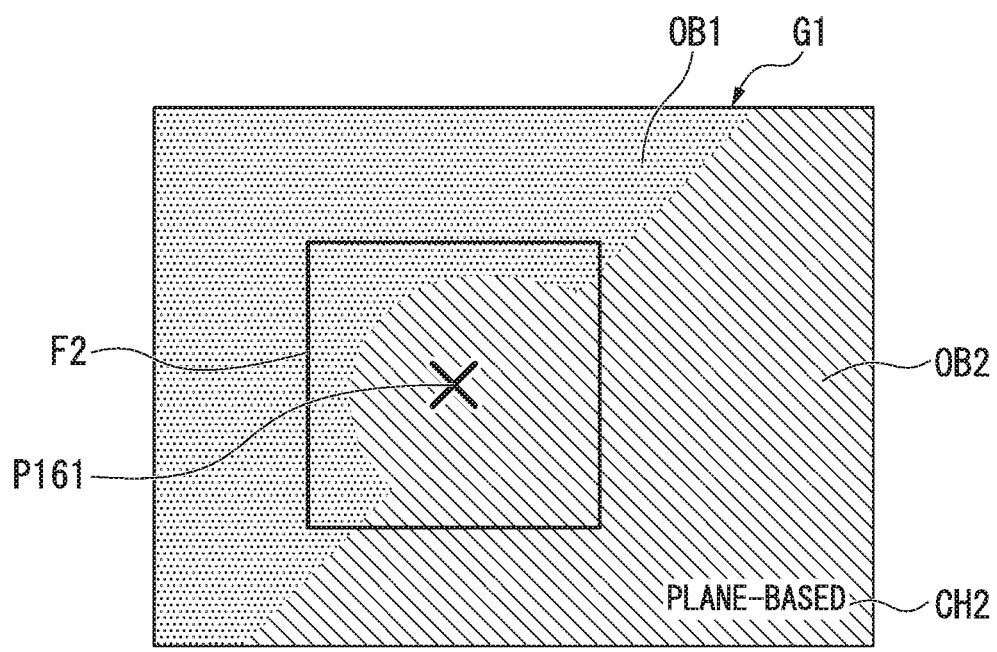
FIGS. 27A and 27B are diagrams showing an example of an image displayed on a display unit according to the sixth embodiment of the present invention.

FIG. 27A shows an example of an image displayed on the display unit 5. As shown in FIG. 27A, an image G1 including images of a subject OB1 and a subject OB2 is displayed. Character CH2 indicating plane-based measurement are displayed on the image G1. The image G1 after the measurement designation point is designated in step S321 is shown in FIG. 27A.

In step S321, a measurement designation point P161 is set on the subject OB2. In step S322, the reference designation point setting unit 182 sets a frame F2 based on the measurement designation point P161. For example, a frame F2 centering on the measurement designation point P161 is set. For example, the frame F2 is square. The shape of the frame F2 is not limited thereto. The reference designation point setting unit 182 divides a region within the frame F2 into a plurality of partial regions. For example, the reference designation point setting unit 182 detects an edge within the frame F2, and divides a region within the frame F2 into a plurality of partial regions so that the edge serves as a boundary between each partial region.

Figure 27B:
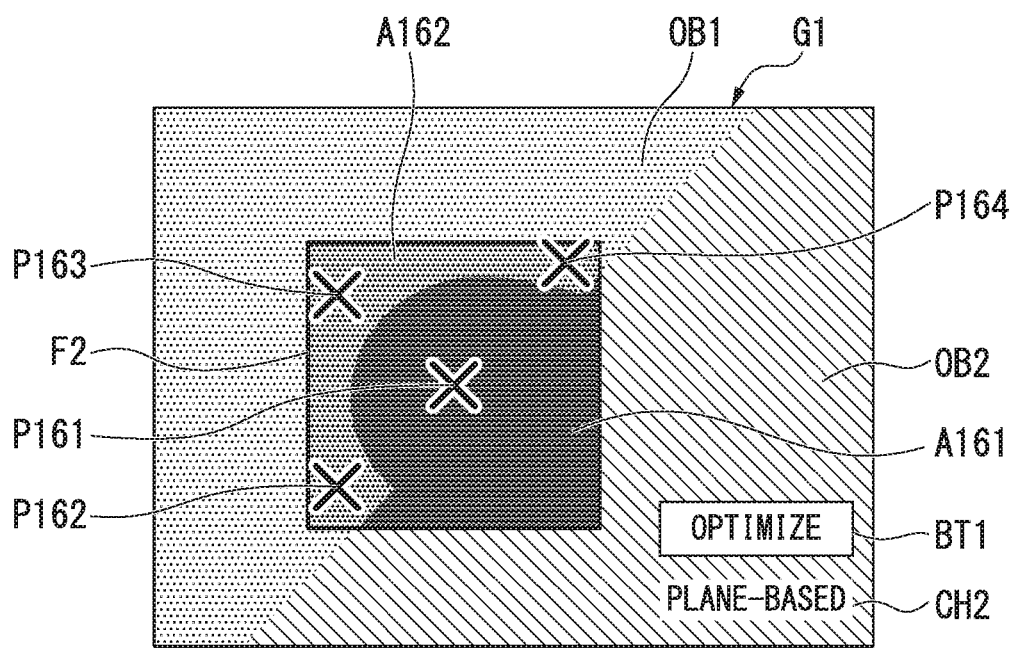

As shown in FIG. 27B, the region within the frame F2 is divided into a partial region A161 and a partial region A162. The reference designation point setting unit 182 sets any three points, located within the partial region A162 different from the partial region A161 at which the measurement designation point P161 is set, to a first reference designation point P162, a second reference designation point P163, and a third reference designation point P164. The first reference designation point P162, the second reference designation point P163, and the third reference designation point P164 are displayed on the image G1. A first auxiliary line connecting the three reference designation points in order is displayed on the image G1. As shown in FIG. 27B, the display of the first auxiliary line is omitted.

In step S304, a first reference plane is calculated. A region which is coincident with the surface of the subject OB1 in the first reference plane is displayed on the image G1. In FIG. 27B, the display of the region is omitted.

A button BT1 is displayed on the image G1. When the button BT1 is pressed, an instruction for the optimization of a reference point is input in step S306.

In a case where the region within the frame F2 is divided into three or more partial regions, the reference designation point setting unit 182 may set three reference designation points in a largest partial region among partial regions different from the partial region A161 at which the measurement designation point P161 is set. However, in a case where the size of the largest region among three or more partial regions is smaller than a predetermined size, it is determined that a reference plane to be used as the first reference plane is not detected. In that case, the display control unit 181 may cause the display unit 5 to display a message indicating that the reference plane has not been detected. The reference designation point setting unit 182 may divide the region within the frame F2 into a plurality of partial regions in consideration of a shape within the frame F2.

After step S308, a user may determine whether the first reference point, the second reference point, and the third reference point are adopted as formal reference points. For example, in a case where the button BT2 shown in FIG. 5B is displayed and the button BT2 is pressed, the process in step S309 may be executed. Alternatively, in a case where the button BT3 shown in FIG. 5B is displayed and the button BT3 is pressed, the process in step S321 may be executed.

After step S304, the process in step S307 may be executed. That is, the process in step S306 may be omitted.

As described above, a user designates one measurement designation point. Therefore, as compared with the second embodiment in which three reference designation points and one measurement designation point are required to be designated, it is possible to reduce the burden of a user's operation. In addition, as compared with the fourth embodiment in which one reference designation point and one measurement designation point are required to be designated, it is possible to reduce the burden of a user's operation.

Seventh Embodiment

An endoscope device 1 according to a seventh embodiment of the present invention has a line-based measurement function and a plane-based measurement function. The endoscope device 1 determines a measurement mode in accordance with information of a point designated by a user.

Figure 28:
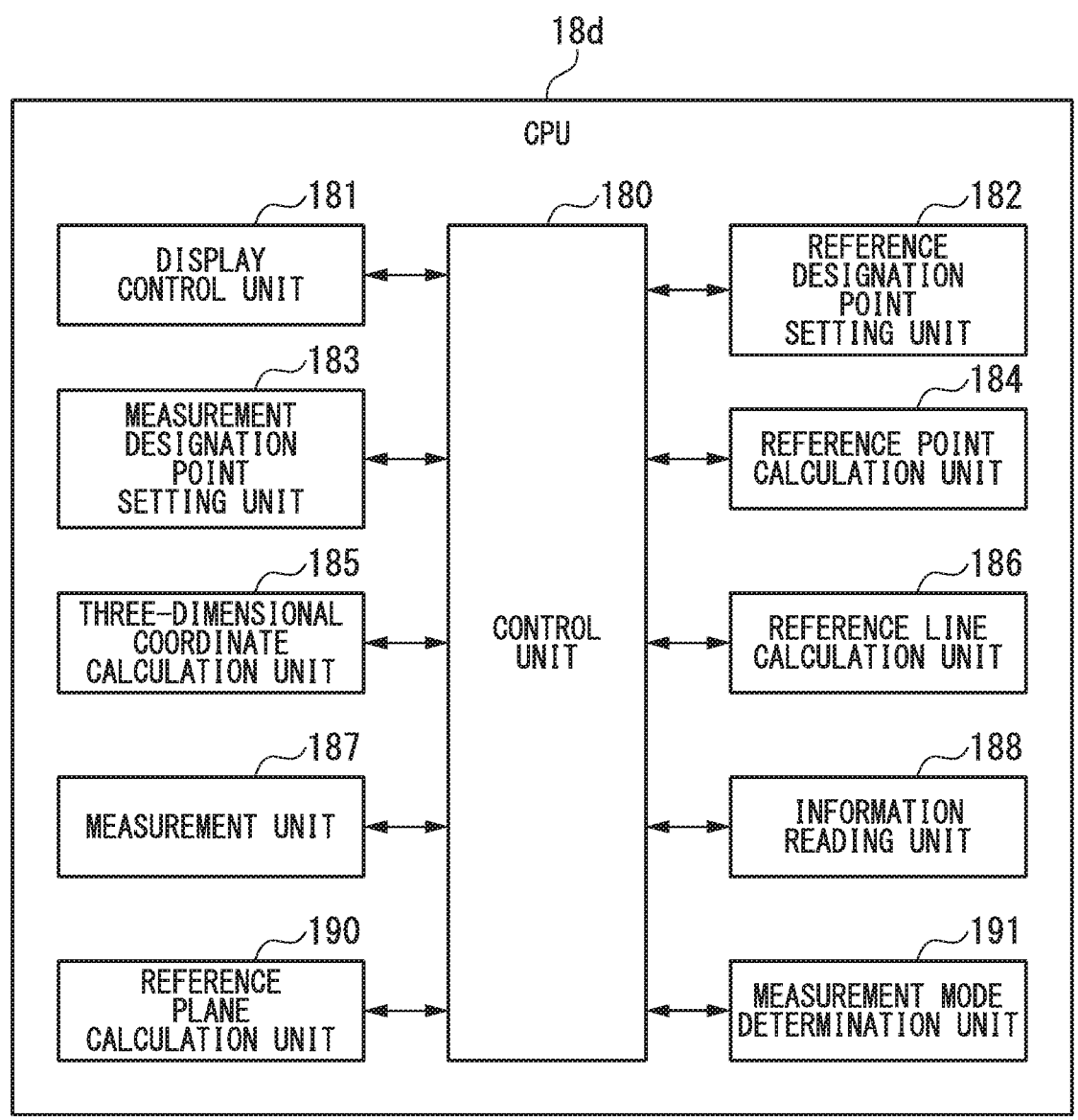
FIG. 28 is a block diagram showing a functional configuration of a CPU according to a seventh embodiment of the present invention.

In the seventh embodiment, the CPU 18a in the first embodiment is changed to a CPU 18d shown in FIG. 28. FIG. 28 shows a functional configuration of the CPU 18d. Regarding the configuration shown in FIG. 28, points different from those of the configuration shown in FIG. 3 will be described.

The CPU 18d includes a reference plane calculation unit 190 and a measurement mode determination unit 191, in addition to the configuration shown in FIG. 3. The reference plane calculation unit 190 is the same as the reference plane calculation unit 190 in the CPU 18c shown in FIG. 11. The measurement mode determination unit 191 determines a measurement mode on the basis of information of at least one of the reference designation point and the measurement designation point designated by a user. Specifically, the measurement mode determination unit 191 determines a measurement mode on the basis of the position (second position) of the measurement designation point designated by a user.

First measurement mode information and second measurement mode information are recorded in the ROM 13. The first measurement mode information indicates the line-based measurement, and the second measurement mode information indicates the plane-based measurement. The information reading unit 188 reads out measurement mode information indicating the measurement mode determined by the measurement mode determination unit 191 from the ROM 13.

The measurement mode determination unit 191 may be constituted by at least one of a processor and a logic circuit. The measurement mode determination unit 191 can include one or a plurality of processors. The measurement mode determination unit 191 can include one or a plurality of logic circuits.

Regarding points other than those stated above, the configuration shown in FIG. 28 is the same as the configuration shown in FIG. 3.

Figure 29:
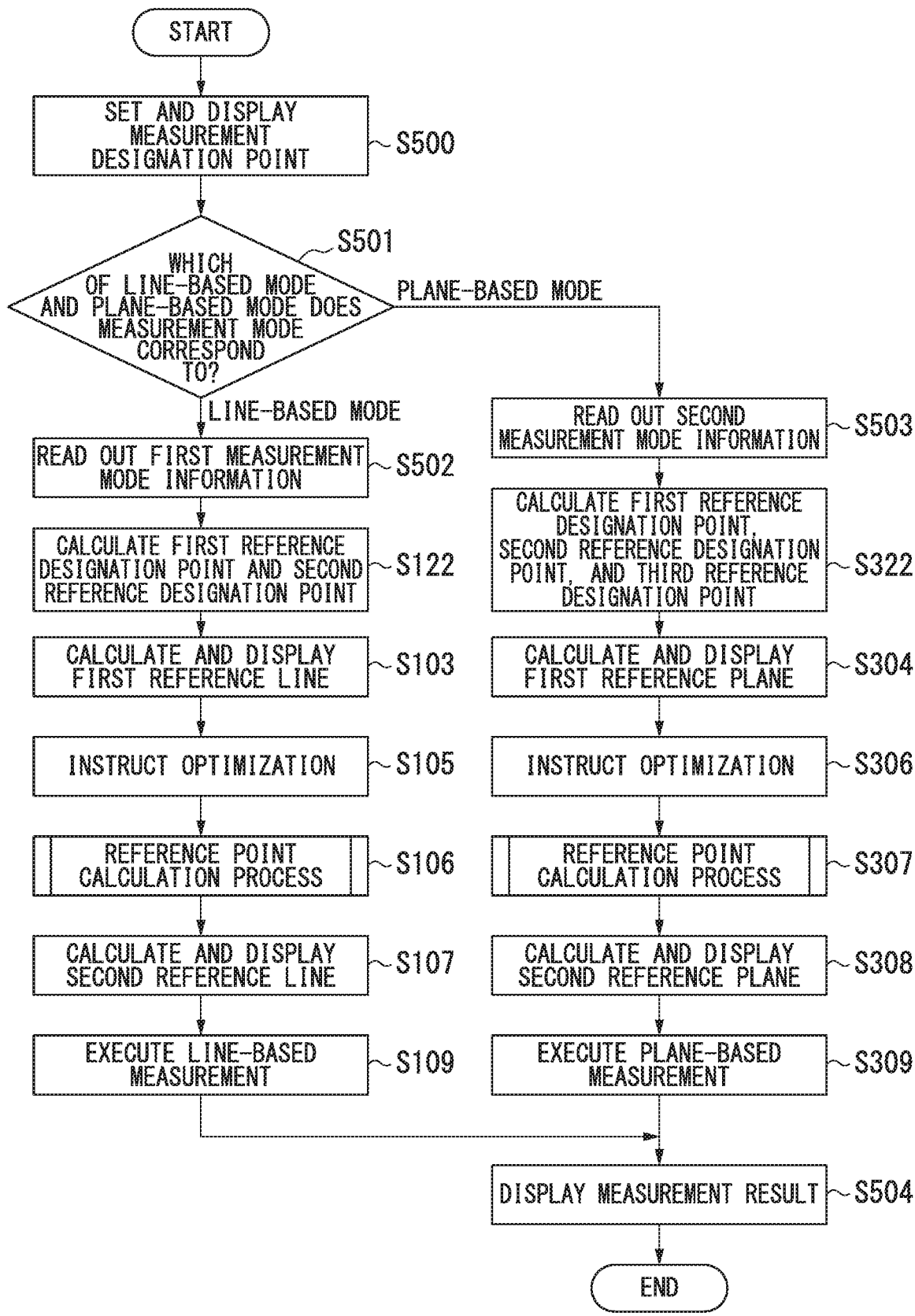
FIG. 29 is a flow diagram showing a procedure of three-dimensional measurement in the seventh embodiment of the present invention.

Three-dimensional measurement in the seventh embodiment will be described with reference to FIG. 29. FIG. 29 shows a procedure of the three-dimensional measurement.

The measurement designation point setting unit 183 determines a position designated as a measurement designation point by a user on the basis of the operation result of the operation unit 4, and sets the measurement designation point at the position. The display control unit 181 displays the measurement designation point on an image (step S500). In the seventh embodiment, the measurement designation point is the same as a measurement point. Therefore, the measurement designation point set in step S500 is also handled as the measurement point.

After step S500, the measurement mode determination unit 191 determines a measurement mode on the basis of the position of the measurement designation point (step S501). The details of the process in step S501 will be described. For example, the measurement mode determination unit 191 extracts the edge of an image. The measurement mode determination unit 191 determines whether a distance between the measurement designation point and the extracted edge is smaller than a predetermined value. In a case where the distance between the measurement designation point and the edge is smaller than the predetermined value, it is estimated that a user has designated the measurement designation point on the edge or in the vicinity of the edge. Therefore, the measurement mode determination unit 191 determines that the measurement mode is a line-based mode. In a case where the distance between the measurement designation point and the edge is larger than the predetermined value, it is estimated that a user has designated the measurement designation point on a plane. Therefore, the measurement mode determination unit 191 determines that the measurement mode is a plane-based mode.

The measurement mode determination unit 191 may determine whether the measurement designation point is located on a plane, on the basis of a variation in the three-dimensional coordinates of pixels in the vicinity of the measurement designation point. In a case where the variation is small, the measurement mode determination unit 191 determines that the measurement designation point is located on a plane. Therefore, the measurement mode determination unit 191 determines that the measurement mode is a plane-based mode. In a case where the variation is large, the measurement mode determination unit 191 determines that the measurement designation point is not located on a plane. Therefore, the measurement mode determination unit 191 determines that the measurement mode is a line-based mode.

In step S501, in a case where the measurement mode determination unit 191 determines that the measurement mode is a line-based mode, the information reading unit 188 reads out the first measurement mode information from the ROM 13 (step S502). The read-out first measurement mode information indicates the line-based measurement. Each unit of the CPU 18d executes a process specified in the line-based measurement.

After step S502, the process in step S122 is executed. After step S122, the process in step S103 is executed. After step S103, the processes in steps S105 to S107 are executed. After step S107, the process in step S109 is executed. These processes are the same as the processes shown in FIG. 24.

In step S501, in a case where the measurement mode determination unit 191 determines that the measurement mode is a plane-based mode, the information reading unit 188 reads out the second measurement mode information from the ROM 13 (step S503). The read-out second measurement mode information indicates the plane-based measurement. Each unit of the CPU 18d executes a process specified in the plane-based measurement.

After step S503, the process in step S322 is executed. After step S322, the process in step S304 is executed. After step S304, the processes in steps S306 to S309 are executed. These processes are the same as the processes shown in FIG. 26.

After step S109 or S309, the display control unit 181 causes the display unit 5 to display a measurement result. That is, the display control unit 181 causes the display unit 5 to display the three-dimensional distance calculated in step S109 or S309 (step S504). The process in step S504 is executed, and thus the three-dimensional measurement is terminated.

Figure 30A:
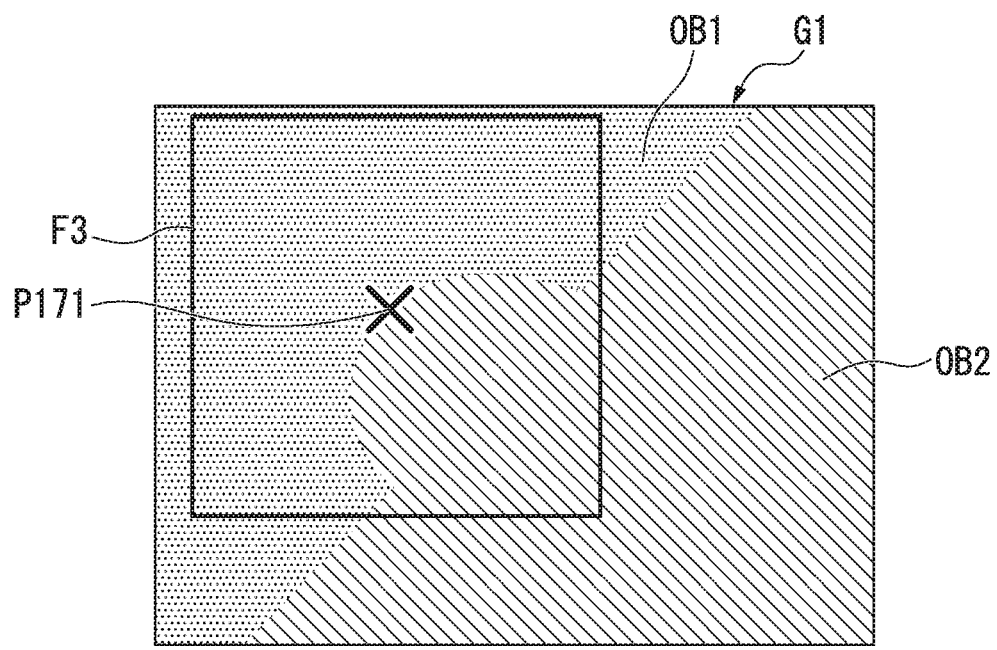
FIGS. 30A and 30B are diagrams showing a first example of an image displayed on a display unit according to the seventh embodiment of the present invention.

FIG. 30A shows a first example of an image displayed on the display unit 5. As shown in FIG. 30A, an image G1 including images of a subject OB1 and a subject OB2 is displayed. In step S500, a measurement designation point P171 on the edge of the subject OB1 is set. Since the measurement designation point P171 is located on the edge, it is determined that the measurement mode is a line-based mode in step S501.

In the line-based mode, the line-based measurement in the fifth embodiment is executed. In step S122, the reference designation point setting unit 182 sets a frame F3 based on the measurement designation point P171. The reference designation point setting unit 182 detects an edge within the frame F3.

Figure 30B:
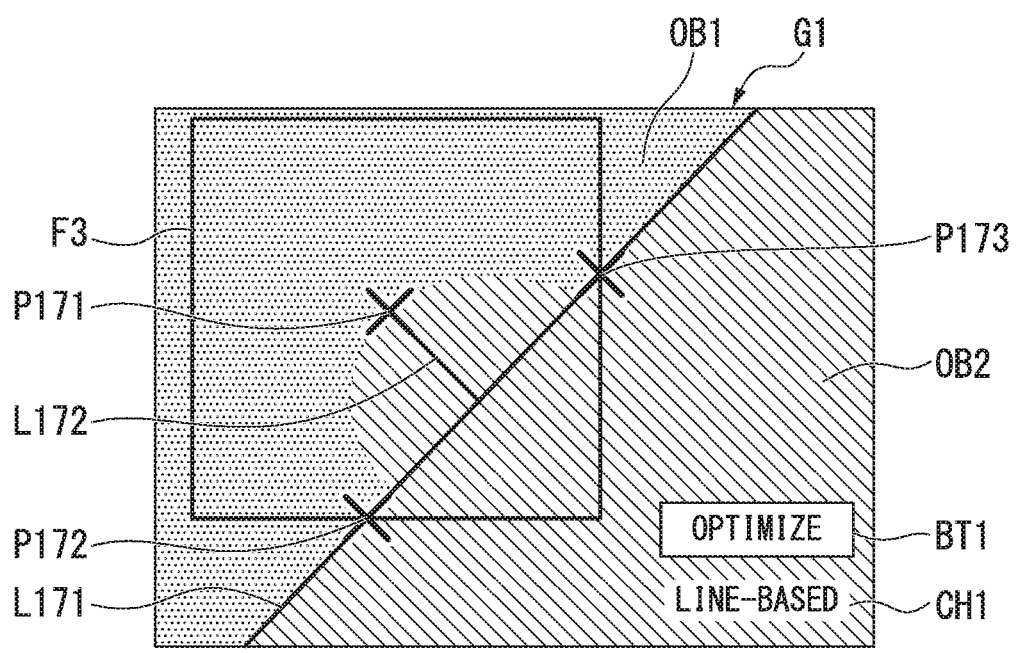

As shown in FIG. 30B, the reference designation point setting unit 182 sets a first reference designation point P172 and a second reference designation point P173 at the positions of two points of intersection between the detected edge and the frame F3. The first reference designation point P172 and the second reference designation point P173 are displayed on the image G1.

In step S103, a first reference line is calculated. A two-dimensional first reference line L171 and a two-dimensional first auxiliary line L172 are displayed on the image G1.

A button BT1 is displayed on the image G1. When the button BT1 is pressed, an instruction for the optimization of a reference point is input in step S105.

Figure 31A:
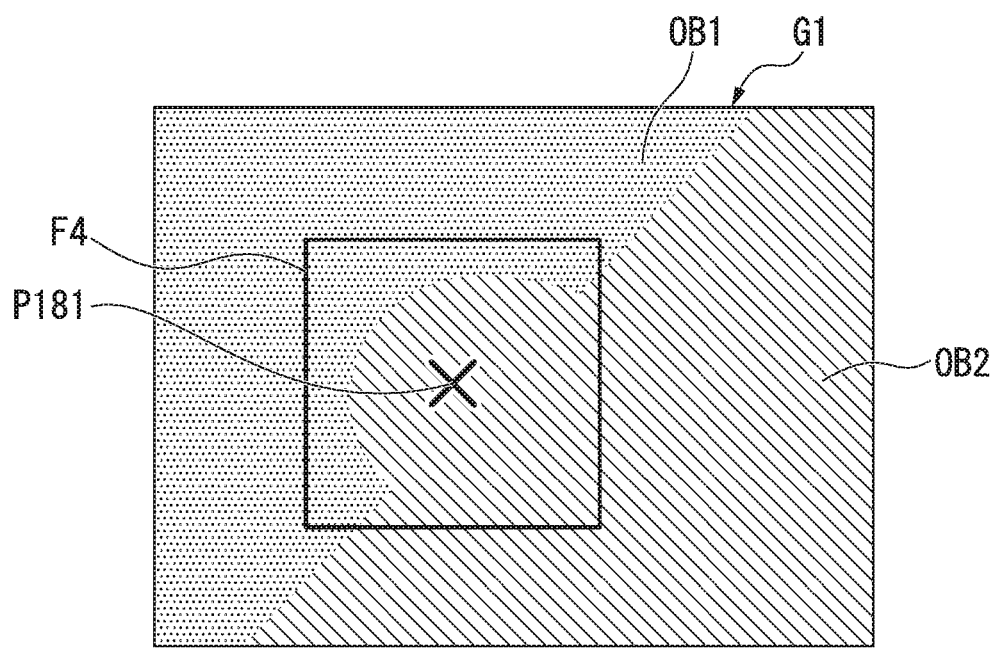
FIGS. 31A and 31B are diagrams showing a second example of an image displayed on the display unit according to the seventh embodiment of the present invention.

FIG. 31A shows a second example of an image displayed on the display unit 5. As shown in FIG. 31A, an image G1 including images of a subject OB1 and a subject OB2 is displayed. In step S500, a measurement designation point P181 is set on the subject OB2. Since the measurement designation point P181 is located on a plane, it is determined that the measurement mode is a plane-based mode in step S501.

In the plane-based mode, the plane-based measurement in the sixth embodiment is executed. In step S322, the reference designation point setting unit 182 sets a frame F4 based on the measurement designation point P181. The reference designation point setting unit 182 divides a region within the frame F4 into a plurality of partial regions.

Figure 31B:
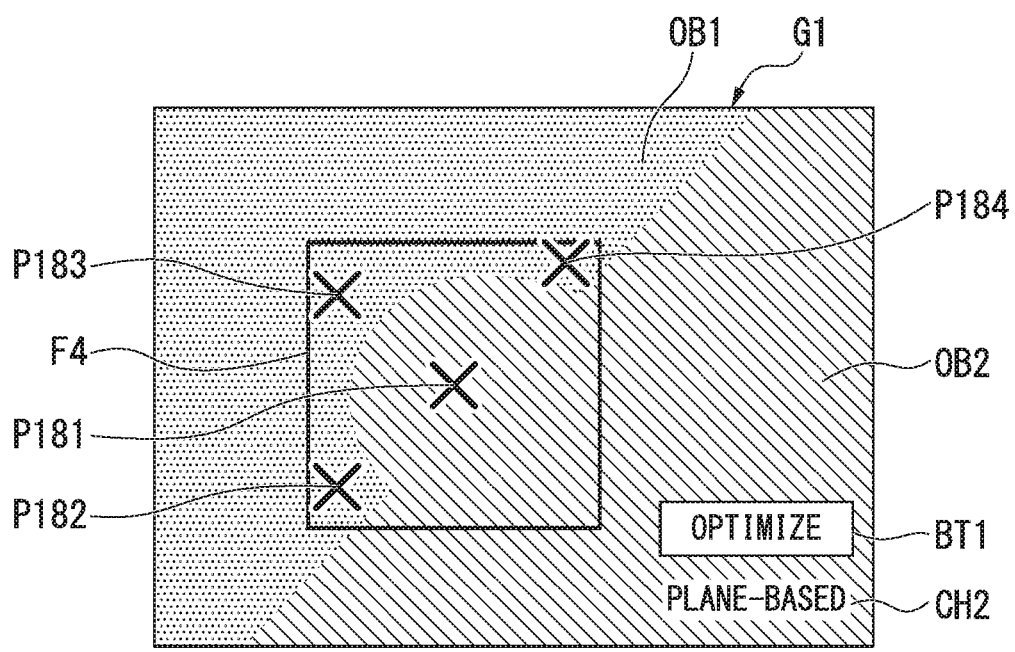

As shown in FIG. 31B, the reference designation point setting unit 182 sets any three points within a partial region different from the partial region in which the measurement designation point P181 is set, to a first reference designation point P182, a second reference designation point P183, and a third reference designation point P184. The first reference designation point P182, the second reference designation point P183, and the third reference designation point P184 are displayed on the image G1. A first auxiliary line connecting the three reference designation points in order is displayed on the image G1. In FIG. 31B, the display of the first auxiliary line is omitted.

In step S304, a first reference plane is calculated. A region which is coincident with the surface of the subject OB1 in the first reference plane is displayed on the image G1. The display of the region is omitted in FIG. 31B.

A button BT1 is displayed on the image G1. When the button BT1 is pressed, an instruction for the optimization of a reference point is input in step S306.

In the process shown in FIG. 29, the measurement mode is determined on the basis of the position of the measurement designation point. A method of determining the measurement mode is not limited thereto. In a case where it is difficult to determine the measurement mode based on the measurement designation point and an image in the vicinity of the measurement designation point, information of the reference designation point may be used in the determination of the measurement mode, in addition to information of the measurement designation point.

After step S107, a user may determine whether the first reference point and the second reference point are adopted as formal reference points. For example, in a case where the button BT2 shown in FIG. 5B is displayed and the button BT2 is pressed, the process in step S109 may be executed. Alternatively, in a case where the button BT3 shown in FIG. 5B is displayed and the button BT3 is pressed, the process in step S500 may be executed.

After step S103, the process in step S106 may be executed. That is, the process in step S105 may be omitted.

After step S308, a user may determine whether the first reference point, the second reference point, and the third reference point are adopted as formal reference points. For example, in a case where the button BT2 shown in FIG. 5B is displayed and the button BT2 is pressed, the process in step S309 may be executed. Alternatively, in a case where the button BT3 shown in FIG. 5B is displayed and the button BT3 is pressed, the process in step S500 may be executed.

After step S304, the process in step S307 may be executed. That is, the process in step S306 may be omitted.

As described above, the measurement mode determination unit 191 determines a measurement mode on the basis of information of at least one of the reference designation point and the measurement designation point designated by a user. In the endoscope device 1 configured such that the measurement mode can be switched between the line-based measurement and the plane-based measurement, a user does not need to set the measurement mode in advance. Therefore, the endoscope device 1 can reduce the burden of a user's operation.

Modification Example of Seventh Embodiment

In a modification example of the seventh embodiment of the present invention, the measurement mode determination unit 191 determines a measurement mode on the basis of the numbers of reference designation points and measurement designation points designated by a user.

Figure 32A:
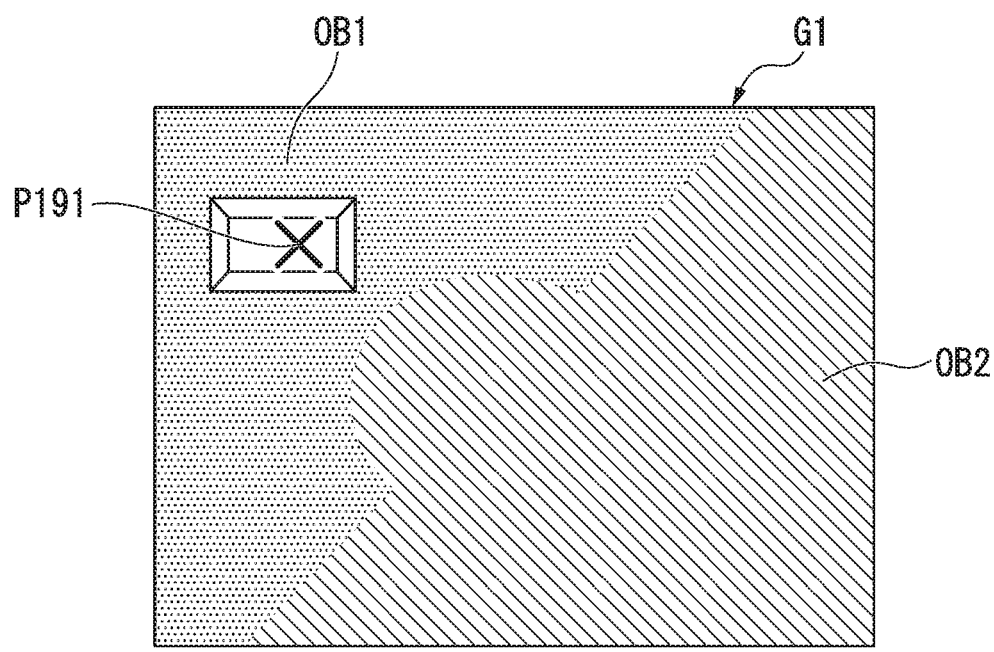
FIGS. 32A and 32B are diagrams showing an example of an image displayed on a display unit according to a modification example of the seventh embodiment of the present invention.
Figure 32B:
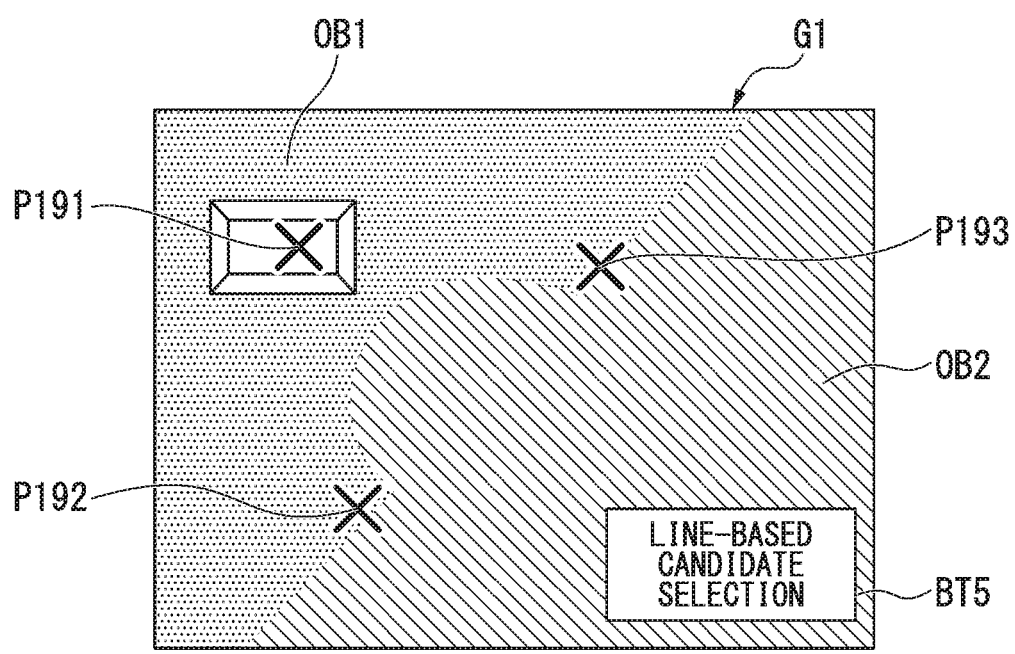

FIG. 32A shows an example of an image displayed on the display unit 5. As shown in FIG. 32A, an image G1 including images of a subject OB1 and a subject OB2 is displayed. A measurement designation point P191 is set in a convex portion on the subject OB1 on the basis of a user's instruction. The measurement designation point P191 is displayed on the image G1. Thereafter, as shown in FIG. 32B, a first reference designation point P192 and a second reference designation point P193 are set in the vicinity of the edge of the subject OB1 on the basis of a user's instruction. The first reference designation point P192 and the second reference designation point P193 are displayed on the image G1.

After the two reference designation points are set, a button BT5 is displayed on the image G1. A user can press the button BT5 through the same operation as the operation of the button BT1 shown in FIG. 5A. When the button BT5 is pressed, an instruction for the optimization of a reference point for the line-based measurement is input. Thereby, the two reference designation points are settled. Therefore, the measurement mode determination unit 191 determines that the measurement mode is a line-based mode.

Figure 33A:
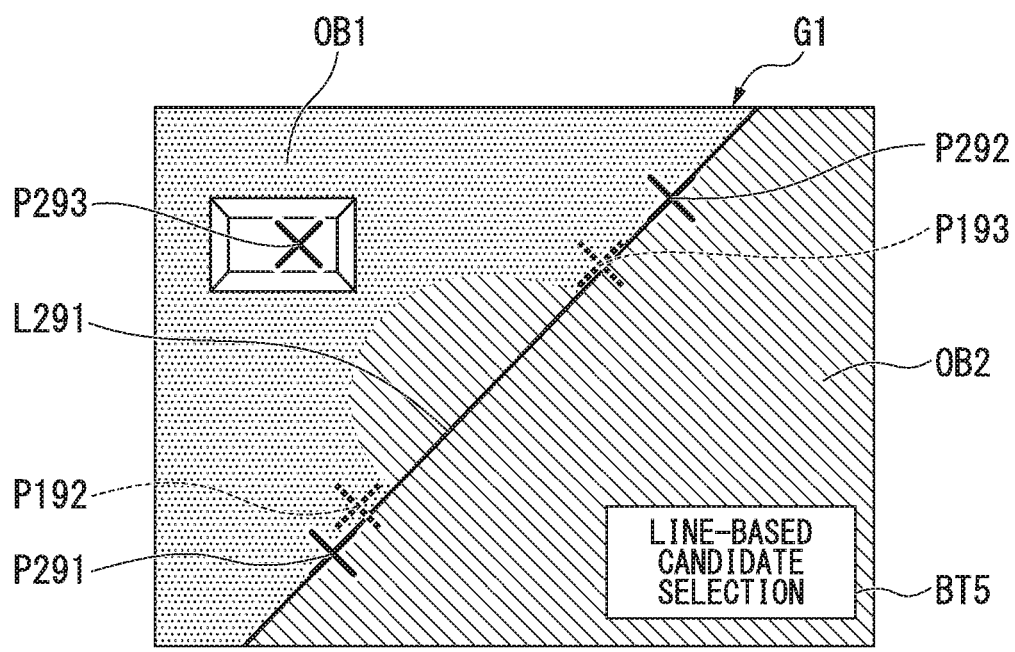
FIGS. 33A and 33B are diagrams showing an example of an image displayed on the display unit according to the modification example of the seventh embodiment of the present invention.

FIG. 33A shows an example of an image displayed on the display unit 5 when the button BT5 shown in FIG. 32B is pressed. A first reference point P291 and a second reference point P292 are calculated on the basis of the first reference designation point P192 and the second reference designation point P193. The first reference point P291 and the second reference point P292 are displayed on the image G1. A measurement point P293 is displayed at the same position as that of the measurement designation point P191. A second reference line is calculated, and a two-dimensional second reference line L291 is displayed on the image G1.

Figure 33B:
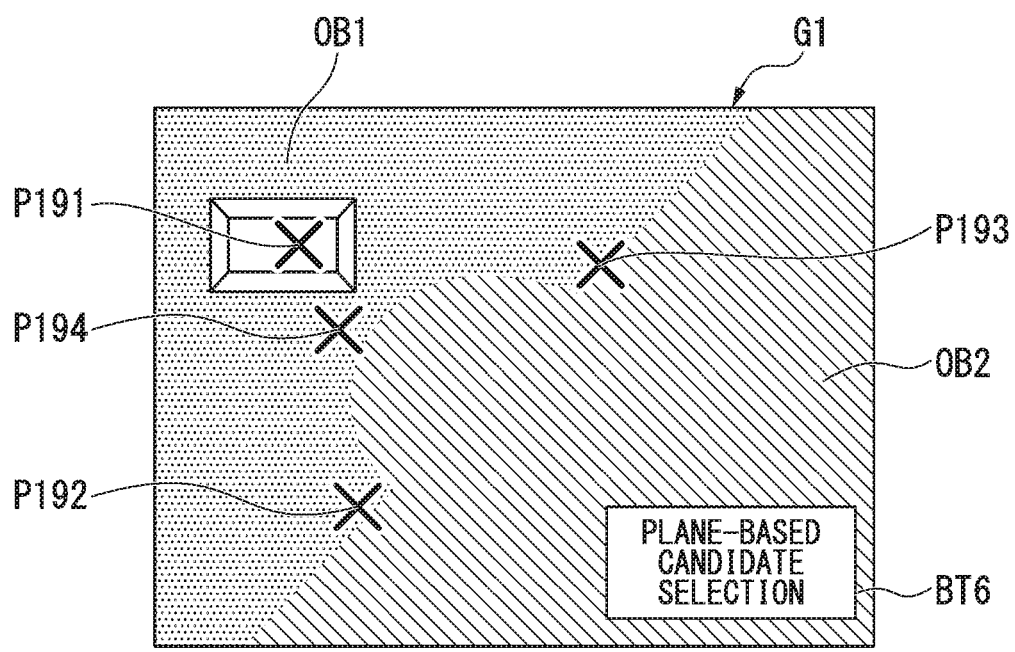

FIG. 33B shows an example of an image displayed on the display unit 5 when a third reference designation point is set without the button BT5 shown in FIG. 32A being pressed. After the first reference designation point P192 and the second reference designation point P193 are set, a user can designate a third reference designation point without pressing the button BT5. A third reference designation point P194 is set in the vicinity of the edge of the subject OB1 on the basis of a user's instruction.

After the three reference designation points are set, a button BT6 is displayed on the image G1. A user can press the button BT6 through the same operation as the operation of the button BT1 shown in FIG. 5A. When the button BT6 is pressed, an instruction for the optimization of a reference point for the plane-based measurement is input. Thereby, the three reference designation points are settled. Therefore, the measurement mode determination unit 191 determines that the measurement mode is a plane-based mode.

Figure 34:
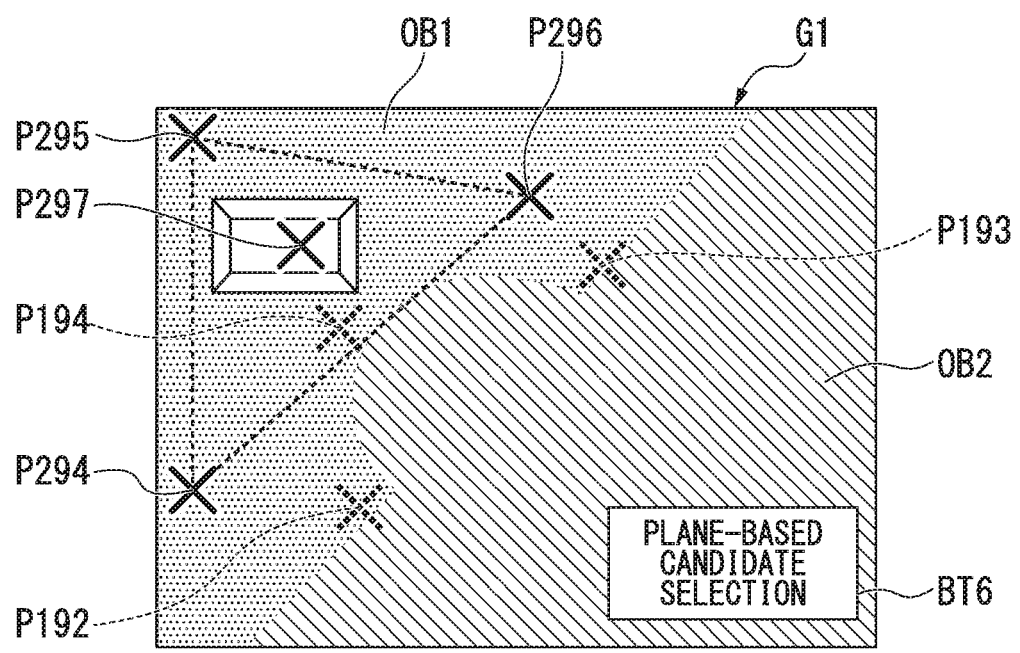
FIG. 34 is a diagram showing an example of an image displayed on the display unit according to the modification example of the seventh embodiment of the present invention.

FIG. 34 shows an example of an image displayed on the display unit 5 when the button BT6 shown in FIG. 33B is pressed. A first reference point P294, a second reference point P295, and a third reference point P296 are calculated on the basis of the first reference designation point P192, the second reference designation point P193, and the third reference designation point P194. The first reference point P294, the second reference point P295, and the third reference point P296 are displayed on the image G1. A measurement point P297 is displayed at the same position as that of the measurement designation point P191. A second reference plane is calculated. A region which is coincident with the surface of the subject OB1 in the second reference plane is displayed on the image G1. In FIG. 34, the display of the region is omitted.

The measurement mode determination unit 191 may determine a measurement mode in accordance with a time elapsed after a user has designated the reference designation point. For example, in a case where a predetermined time has elapsed from a point of time at which the second reference designation point is set without the third reference designation point being designated by a user, the measurement mode determination unit 191 determines that the measurement mode is a line-based mode. Alternatively, the third reference designation point is set before a predetermined time has elapsed from a point of time at which the second reference designation point is set. In that case, the measurement mode determination unit 191 determines that the measurement mode is a plane-based mode.

As described above, the measurement mode determination unit 191 determines a measurement mode on the basis of the numbers of reference designation points and measurement designation points designated by a user. A user does not need to set a measurement mode through multiple operations of a menu including a large number of items. Therefore, the endoscope device 1 can reduce the burden of a user's operation.

Eighth Embodiment

An endoscope device 1 according to an eighth embodiment of the present invention has a line-based measurement function. In addition, a reference designation point and a measurement designation point are designated on an image indicating the three-dimensional shape of a subject. The eighth embodiment will be described using the CPU 18*a* shown in FIG. 3.

In the eighth embodiment, the three-dimensional coordinate calculation unit 185 calculates the three-dimensional coordinates of a plurality of pixels in an image acquired by the CCU 9. The display control unit 181 causes the display unit 5 to display an image (second image) based on the image (first image) acquired by the CCU 9. Specifically, the display control unit 181 causes the display unit 5 to display an image having a three-dimensional shape of a subject constituted by the three-dimensional coordinates calculated by the three-dimensional coordinate calculation unit 185.

The reference designation point setting unit 182 sets a plurality of reference designation points in the image acquired by the CCU 9 and displayed on the display unit 5, on the basis of a position (first position) designated by a user in the image displayed on the display unit 5. The measurement designation point setting unit 183 sets a measurement designation point in the image acquired by the CCU 9 and displayed on the display unit 5, on the basis of a position (second position) designated by a user in the image displayed on the display unit 5. The reference line calculation unit 186 (reference calculation unit) calculates a reference line on the basis of the plurality of reference designation points set by the reference designation point setting unit 182. The reference line is used in a measurement mode indicated by measurement mode information. The reference point calculation unit 184 calculates a plurality of reference points leading to higher reliability of a measurement result instead of the plurality of reference designation points for calculating the reference line.

The reference designation point setting unit 182 may set a plurality of reference designation points in an image having a three-dimensional shape of a subject, on the basis of the position (first position) designated by a user in the image displayed on the display unit 5. The measurement designation point setting unit 183 may set a measurement designation point in the image having a three-dimensional shape of a subject, on the basis of the position (second position) designated by a user in the image displayed on the display unit 5.

Figure 35:
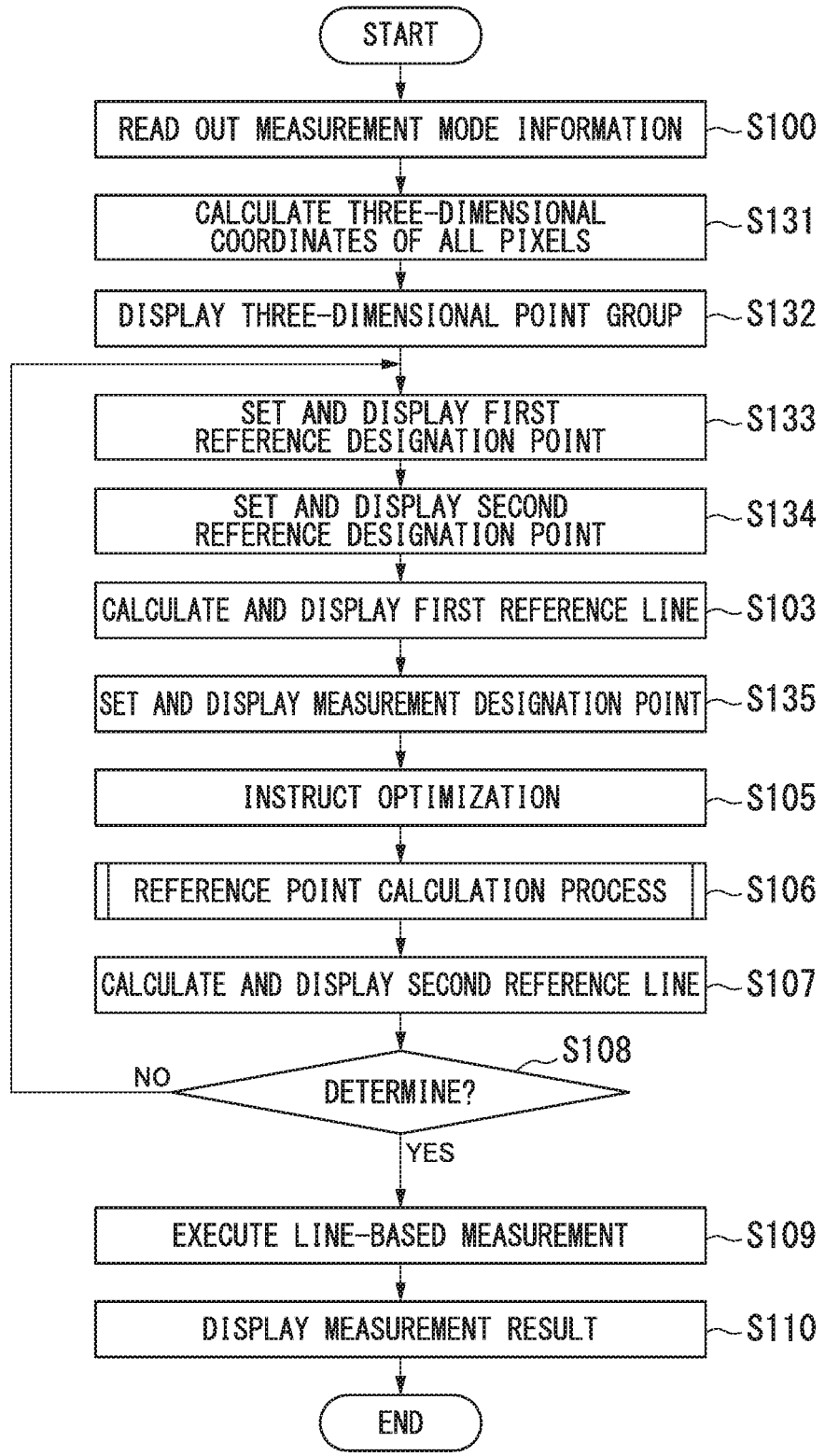
FIG. 35 is a flow diagram showing a procedure of three-dimensional measurement in an eighth embodiment of the present invention.

Three-dimensional measurement in the eighth embodiment will be described with reference to FIG. 35. FIG. 35 shows a procedure of the three-dimensional measurement. Regarding a process shown in FIG. 35, points different from those of the process shown in FIG. 4 will be described.

After step S100, the three-dimensional coordinate calculation unit 185 calculates the three-dimensional coordinates of all pixels in an image (step S131). After step S131, a three-dimensional point group constituted by the calculated three-dimensional coordinates is displayed on the display unit 5 (step S132). The three-dimensional point group constitutes the three-dimensional shape of a subject. A user can designate the reference designation point and the measurement designation point on the displayed three-dimensional point group.

After step S132, the reference designation point setting unit 182 determines a position designated as the reference designation point by a user on the three-dimensional point group, on the basis of the operation result of the operation unit 4. The reference designation point setting unit 182 sets a first reference designation point at a position on a two-dimensional image corresponding to the position designated on the three-dimensional point group. The display control unit 181 displays the first reference designation point on the three-dimensional point group (step S133).

After step S133, the reference designation point setting unit 182 determines the position designated as the reference designation point by a user on the three-dimensional point group, on the basis of the operation result of the operation unit 4. The reference designation point setting unit 182 sets a second reference designation point at a position on a two-dimensional image corresponding to the position designated on the three-dimensional point group. The display control unit 181 displays the second reference designation point on the three-dimensional point group (step S134). After step S134, the process in step S103 is executed.

After step S103, the measurement designation point setting unit 183 determines a position designated as the measurement designation point by a user on the three-dimensional point group, on the basis of the operation result of the operation unit 4. The measurement designation point setting unit 183 sets a measurement designation point at a position on a two-dimensional image corresponding to the position designated on the three-dimensional point group. The display control unit 181 displays a measurement reference designation point on the three-dimensional point group (step S135). After step S135, the process in step S105 executed.

In step S108, in a case where the control unit 180 determines that the first reference point and the second reference point are not adopted as formal reference points by a user, the process in step S133 is executed.

Regarding points other than those stated above, the process shown in FIG. 35 is the same as the process shown in FIG. 4.

Figure 36A:
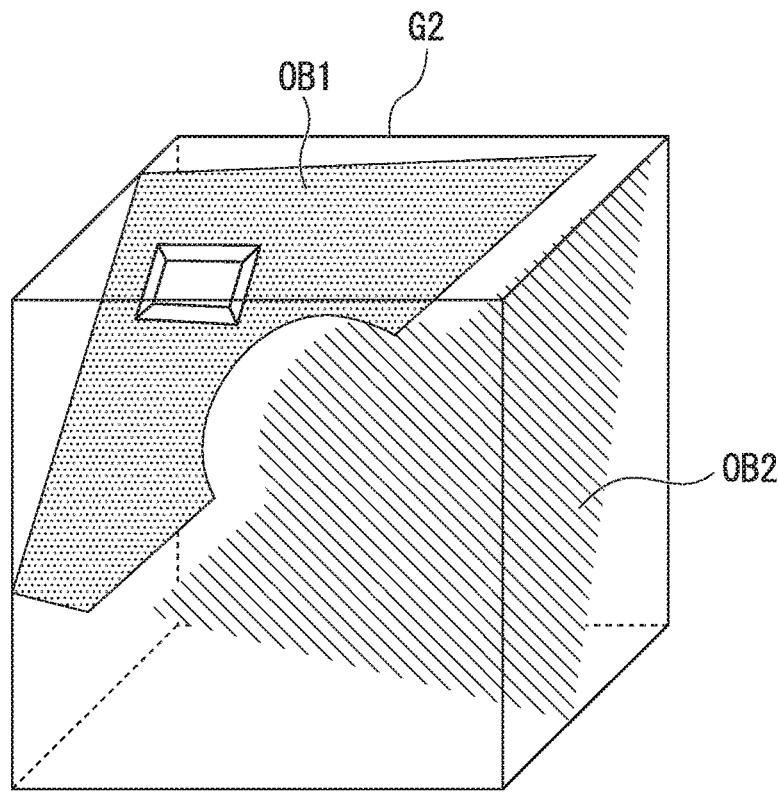
FIGS. 36A and 36B are diagrams showing an example of an image displayed on a display unit according to the eighth embodiment of the present invention.

FIG. 36A shows an example of an image displayed on the display unit 5. As shown in FIG. 36A, an image G2 is displayed in step S132. The image G2 includes a three-dimensional point group of the subject OB1 and a three-dimensional point group of the subject OB2. The RGB value of each point constituting the three-dimensional point group is the same as the RGB value of a pixel of a two-dimensional image corresponding to the point.

Figure 36B:
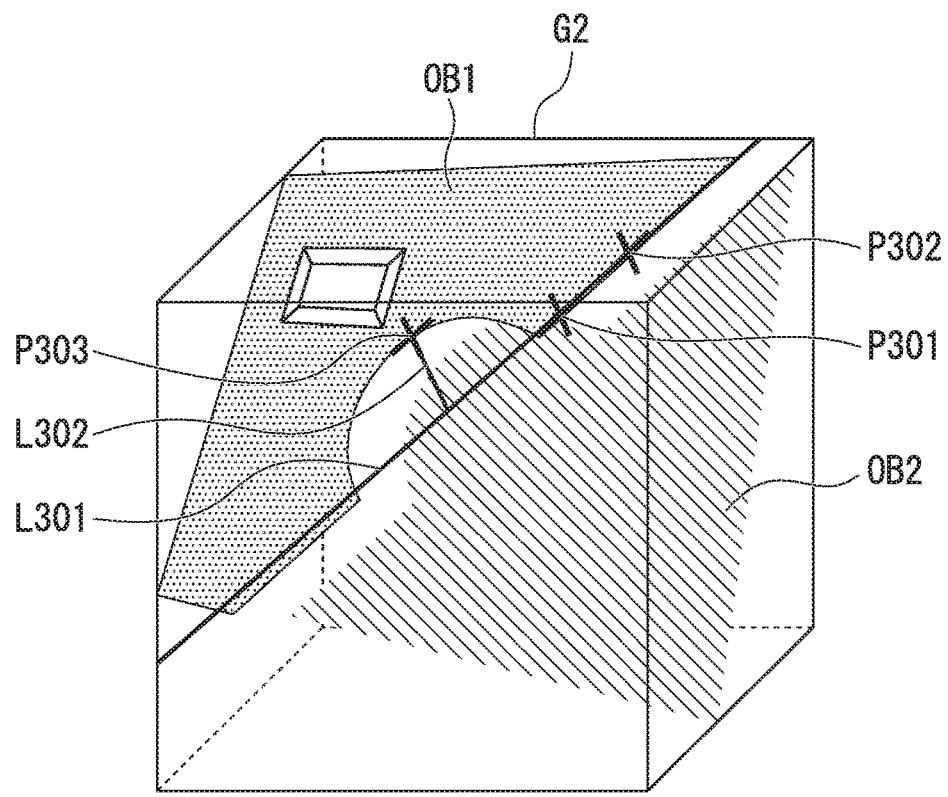

The image G2 after the measurement designation point is designated in step S135 is shown in FIG. 36B. In step S133, a first reference designation point P301 on the edge of the subject OB1 is set. In step S134, a second reference designation point P302 on the edge of the subject OB1 is set. The first reference designation point P301 and the second reference designation point P302 are displayed on the image G2. In step S103, a first reference line is calculated. A two-dimensional first reference line L301 is displayed on the image G2. In step S135, a measurement designation point P303 on the edge of the subject OB1 is set. The measurement designation point P303 and a two-dimensional first auxiliary line L302 are displayed on the image G2.

Figure 37:
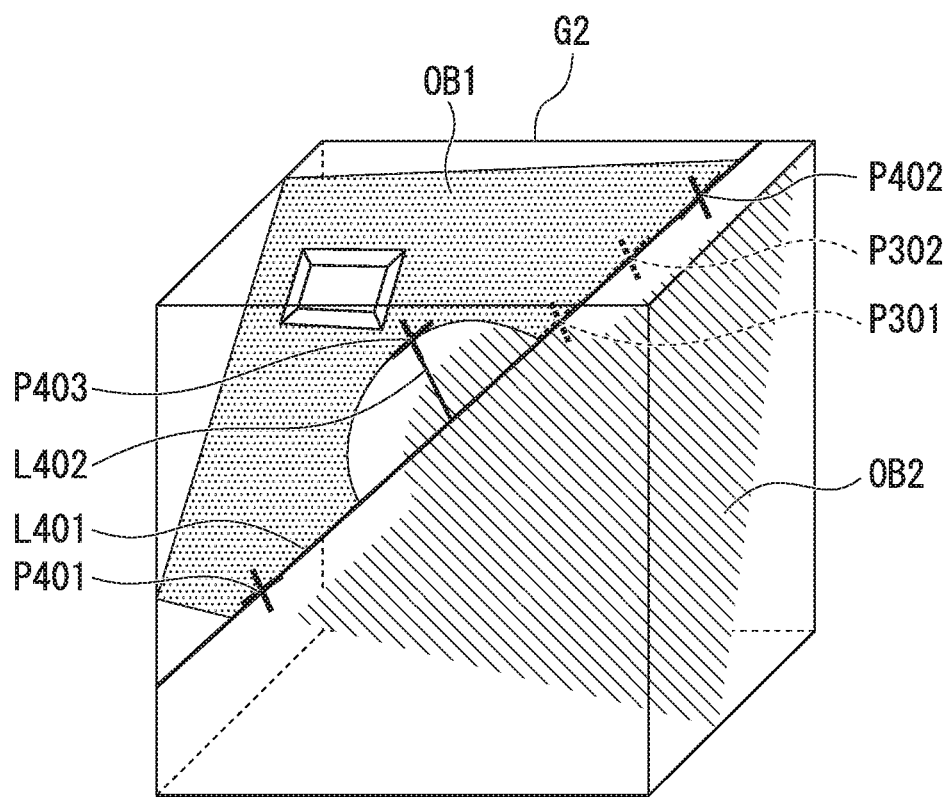
FIG. 37 is a diagram showing an example of an image displayed on the display unit according to the eighth embodiment of the present invention.

FIG. 37 shows an example of an image displayed on the display unit 5 when an instruction for the optimization of a reference point is input in step S105. In step S106, a first reference point P401 and a second reference point P402 are calculated. The first reference point P401 and the second reference point P402 are displayed on the image G2.

A measurement point P403 is displayed at the same position as that of the measurement designation point P303. In step S107, a second reference line is calculated. A two-dimensional second reference line L401 is displayed on the image G2. A two-dimensional second auxiliary line L402 is displayed on the image G2.

A user can change the viewpoint position of the three-dimensional point group on the image G2. Therefore, a user can confirm the three-dimensional shape of a subject at a plurality of angles different from each other.

In the above example, the reference designation point and the measurement designation point are designated on the image having a three-dimensional shape. In the eighth embodiment, one or more points among a plurality of points including the reference designation point and the measurement designation point are designated on the image having a three-dimensional shape.

In the above example, the line-based measurement is performed. In the plane-based measurement, one or more points among a plurality of points including the reference designation point and the measurement designation point may be designated on the image having a three-dimensional shape.

After step S135, the process in step S106 may be executed. That is, the process in step S105 may be omitted.

After step S107, the process in step S109 may be executed. That is, the process in step S108 may be omitted.

The display control unit 181 may cause the display unit 5 to display an image acquired by the CCU 9 and an image having a three-dimensional shape of a subject. In that case, a user's designation of a reference designation point or the like may be performed on either of the two images.

As shown in FIG. 37, the display control unit 181 causes the display unit 5 to display the plurality of reference points calculated by the reference point calculation unit 184 on an image having a three-dimensional shape. As shown in FIG. 37, the display control unit 181 causes the display unit 5 to display the second reference line, determined on the basis of the plurality of reference points calculated by the reference point calculation unit 184, on an image having a three-dimensional shape.

As shown in FIG. 36B and FIG. 37, the display control unit 181 causes the display unit 5 to display the plurality of reference points calculated by the reference point calculation unit 184 and the plurality of reference designation points set by the reference designation point setting unit 182, on an image having a three-dimensional shape. The reference point and the reference designation point may be displayed simultaneously.

As shown in FIG. 36B and FIG. 37, the display control unit 181 causes the display unit 5 to display the second reference line and the first reference line. The second reference line is determined on the basis of the plurality of reference points calculated by the reference point calculation unit 184. The first reference line is determined on the basis of the plurality of reference designation points set by the reference designation point setting unit 182. The second reference line and the first reference line may be displayed simultaneously.

In a case where the plane-based measurement is performed, the display control unit 181 may cause the display unit 5 to display a second reference plane, determined on the basis of the plurality of reference points calculated by the reference point calculation unit 184, on an image having a three-dimensional shape.

In a case where the plane-based measurement is performed, the display control unit 181 may cause the display unit 5 to display the second reference plane and a first reference plane on an image having a three-dimensional shape. The second reference plane is determined on the basis of the plurality of reference points calculated by the reference point calculation unit 184. The first reference plane is determined on the basis of the plurality of reference designation points set by the reference designation point setting unit 182. The second reference plane and the first reference plane may be displayed simultaneously.

As described above, an image having a three-dimensional shape of a subject is displayed, and the reference designation point and the measurement designation point are set on the basis of the positions designated on the image. Therefore, a user can designate the reference designation point and the measurement designation point while confirming the three-dimensional shape of a subject.

Ninth Embodiment

Figure 38:
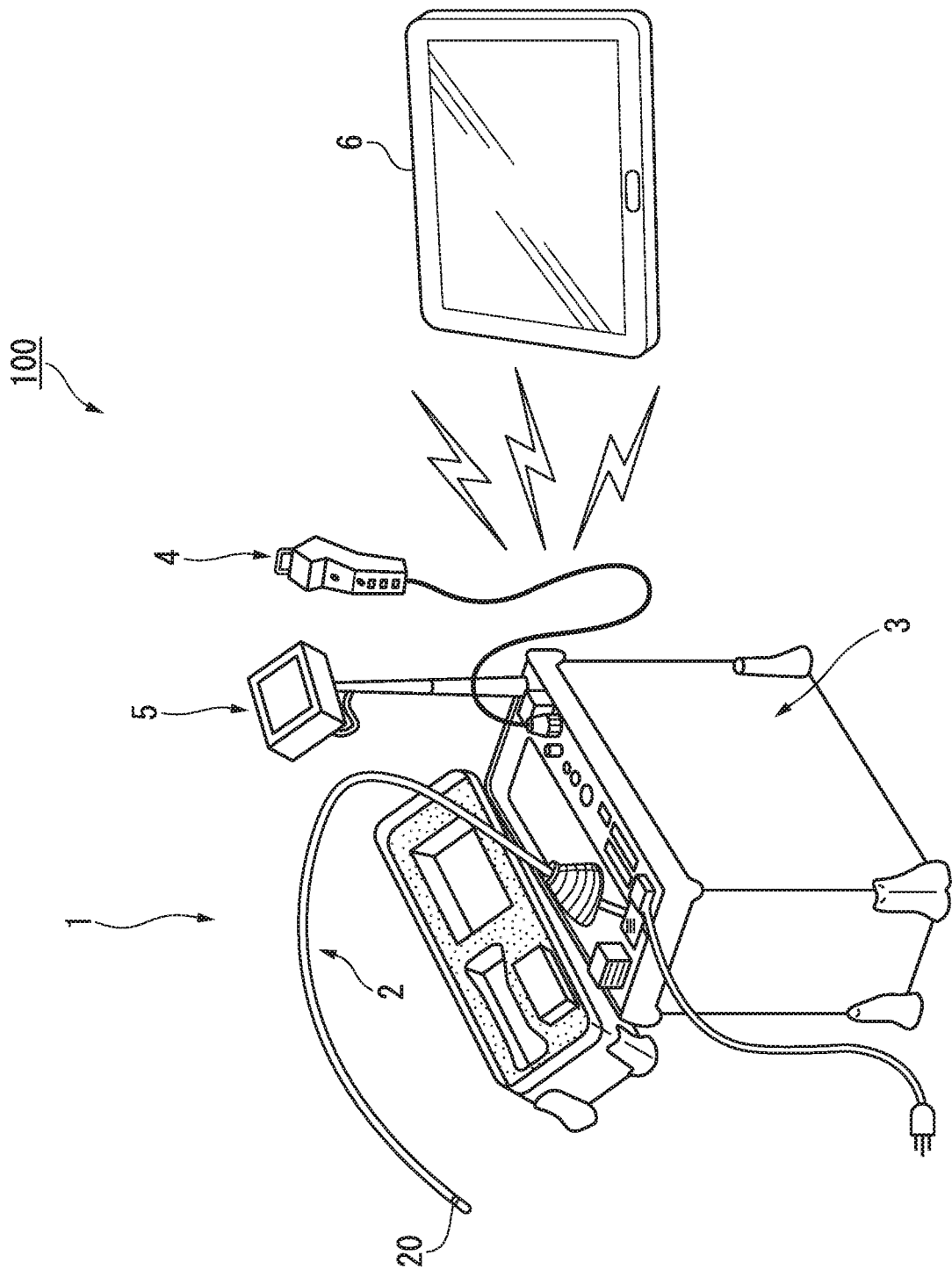
FIG. 38 is a perspective view showing an entire configuration of an endoscope system according to a ninth embodiment of the present invention.

In a ninth embodiment of the present invention, a device that acquires an image of a subject and a device having a measurement function mounted therein are different from each other. FIG. 38 shows a configuration of an endoscope system 100 (measurement system) according to the ninth embodiment. As shown in FIG. 38, the endoscope system 100 includes an endoscope device 1 (image acquisition device) and an external terminal device 6 (measurement device). The endoscope device 1 acquires an image (first image) of a subject. The image acquired by the endoscope device 1 is input to the external terminal device 6. The external terminal device 6 executes the measurement of a subject using the input image.

The configuration of the endoscope device 1 is the same as the configuration shown in FIG. 2. The external device interface 16 performs communication with the external terminal device 6. Specifically, the external device interface 16 transmits an image of a subject and measurement mode information to the external terminal device 6.

For example, the external device interface 16 is a wireless module, and performs wireless communication with the external terminal device 6. The endoscope device 1 and the external terminal device 6 are connected to each other through a cable such as a local area network (LAN) cable, and the external device interface 16 may perform communication with the external terminal device 6 through the cable.

For example, the external terminal device 6 is a mobile terminal such as a tablet terminal. The external terminal device 6 may be a fixed terminal. The form of the external terminal device 6 is not limited thereto.

The CPU 18a controls communication between the external device interface 16 and the external terminal device 6. That is, the CPU 18a causes the external device interface 16 to transmit an image acquired by the CCU 9 and measurement mode information read out from the ROM 13, to the external terminal device 6. The CPU 18a does not need to include at least one of the display control unit 181, the reference designation point setting unit 182, the measurement designation point setting unit 183, the reference point calculation unit 184, the three-dimensional coordinate calculation unit 185, the reference line calculation unit 186, the measurement unit 187, and the information reading unit 188 which are shown in FIG. 3.

Figure 39:
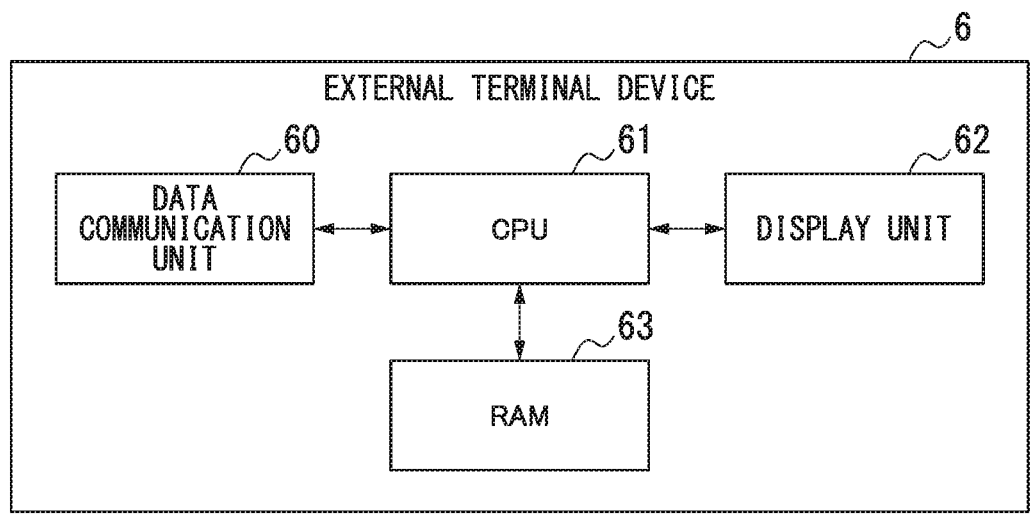
FIG. 39 is a block diagram showing a functional configuration of an external terminal device according to the ninth embodiment of the present invention.

FIG. 39 shows a functional configuration of the external terminal device 6. As shown in FIG. 39, the external terminal device 6 includes a data communication unit 60, a CPU 61, a display unit 62, and a RAM 63.

The data communication unit 60 receives an image of a subject and measurement mode information from the endoscope device 1. For example, the data communication unit 60 is a wireless module, and performs wireless communication with the endoscope device 1. The data communication unit 60 may perform communication with the endoscope device 1 through a cable. The data communication unit 60 functions as an image acquisition unit that acquires an image of a subject.

CPU 61 is configured similarly to the CPU 18*a* shown in FIG. 3. In addition, the CPU 61 controls communication between the data communication unit 60 and the endoscope device 1. That is, the CPU 61 causes the data communication unit 60 to receive the image of the subject and the measurement mode information from the endoscope device 1.

The CPU 61 may read a program including a command for specifying the operation of the CPU 61, and execute the read program. That is, the function of the CPU 61 may be realized by software. An implementation form for this program is the same as an implementation form for a program for realizing the function of the endoscope device 1.

The display unit 62 has a display screen, and displays an image, an operation menu and the like on the display screen. The display unit 62 is a monitor (display) such as an LCD.

The RAM 63 temporarily stores information used for the CPU 61 to control the external terminal device 6.

The external terminal device 6 may include a recording medium having measurement mode information recorded therein in advance. In that case, the endoscope device 1 does not need to transmit the measurement mode information to the external terminal device 6.

Figure 40:
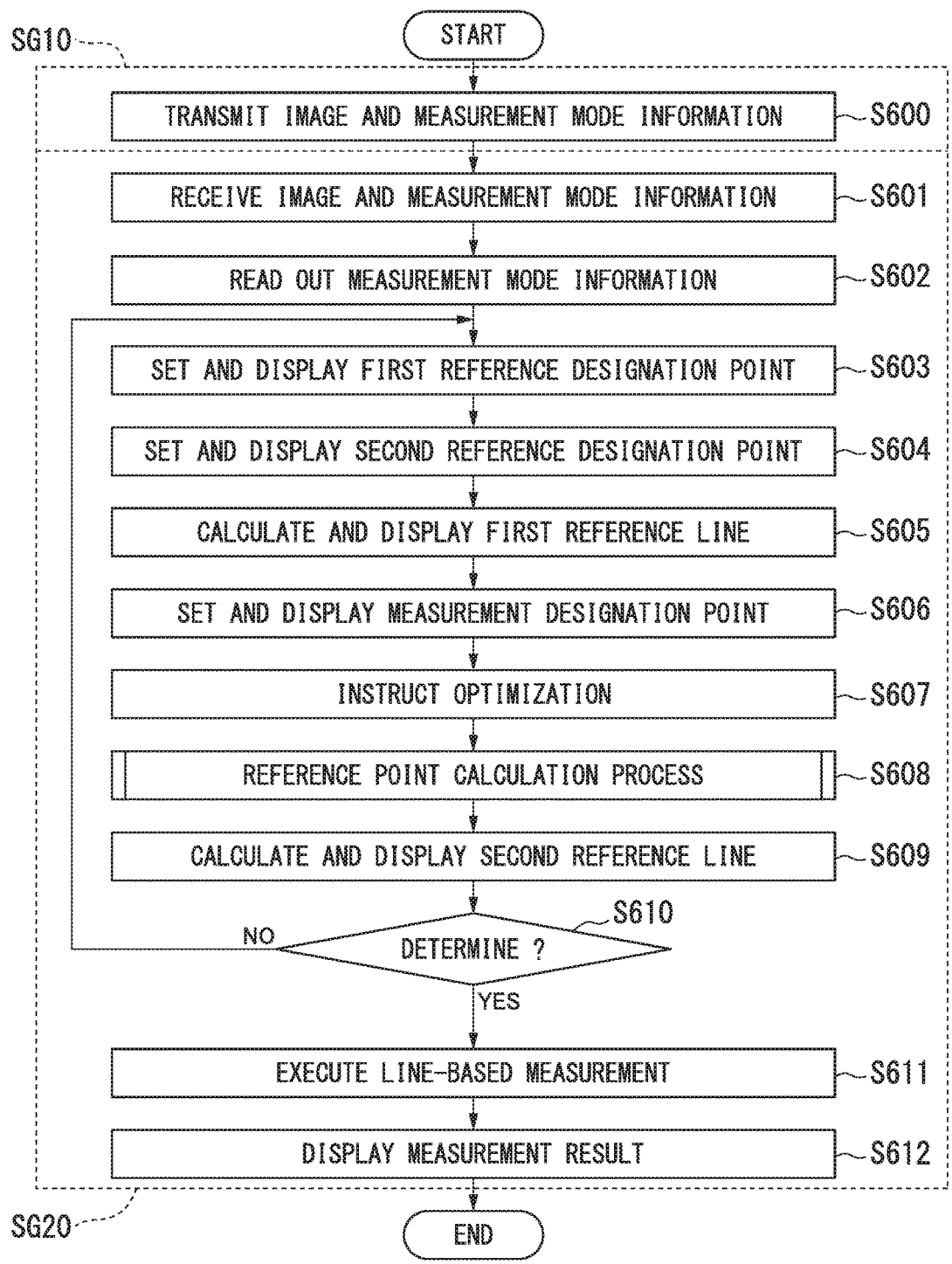
FIG. 40 is a flow diagram showing a procedure of three-dimensional measurement in the ninth embodiment of the present invention.
Figure 41A:
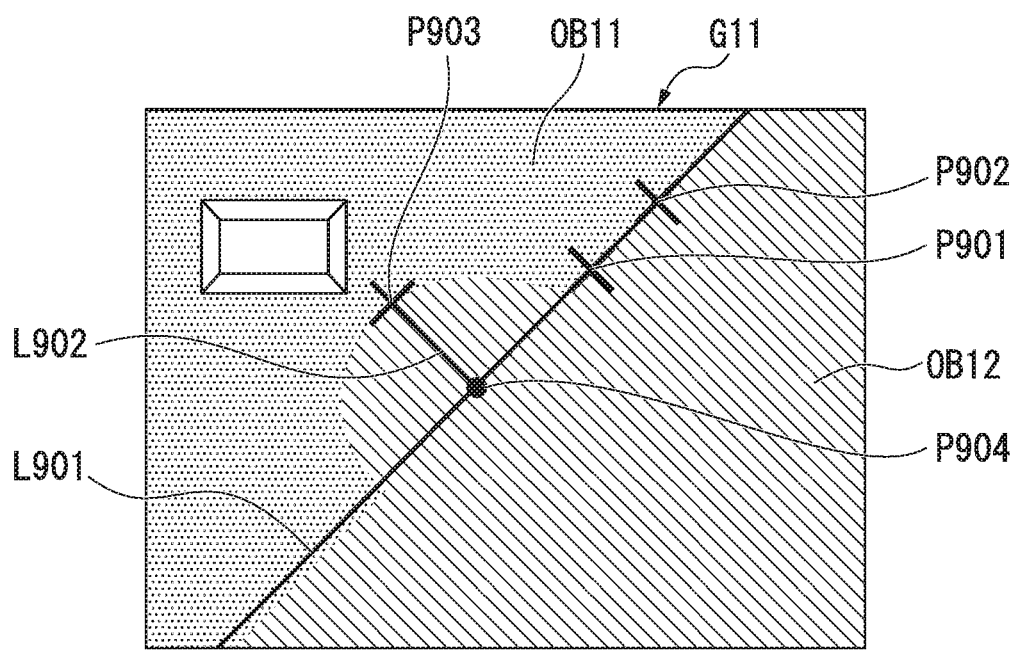
FIGS. 41A and 41B are diagrams showing an example of a measurement point and reference points in line-based measurement.
Figure 41B:
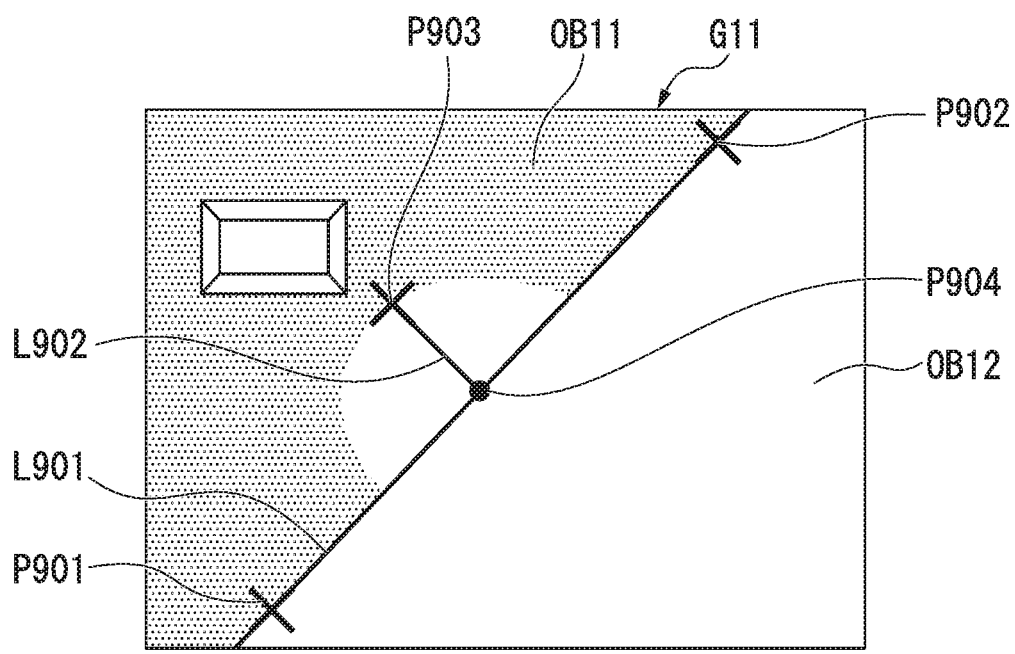

Three-dimensional measurement in the ninth embodiment will be described with reference to FIG. 40. FIG. 40 shows a procedure of the three-dimensional measurement. Processes executed in the three-dimensional measurement include a process SG10 in the endoscope device 1 and a process SG20 in the external terminal device 6. Processes executed by the endoscope device 1 will be described.

The CPU 18*a* outputs the image of the subject and the measurement mode information to the external device interface 16. The CPU 18*a* causes the external device interface 16 to issue a command for transmitting the image of the subject and the measurement mode information to the external terminal device 6. Thereby, the external device interface 16 transmits the image of the subject and the measurement mode information to the external terminal device 6 (step S600). The process in step S600 is executed, and thus the processes in the endoscope device 1 are terminated.

A process executed by the external terminal device 6 will be described. The CPU 61 causes the data communication unit 60 to receive the image of the subject and the measurement mode information from the endoscope device 1. Thereby, the data communication unit 60 receives the image of the subject and the measurement mode information from the endoscope device 1 (step S601). The received image of the subject and measurement mode information are stored in the RAM 63.

After step S601, the process in step S602 is executed. As shown in FIG. 40, the processes in steps S602 to S612 are executed. The processes in steps S602 to S612 are the same as the processes in steps S100 to S110 shown in FIG. 4, respectively. The process in step S612 is executed, and thus the processes in the external terminal device 6 are terminated.

The CPU 61 may be configured similarly to the CPU 18*b* shown in FIG. 9. The CPU 61 may be configured similarly to the CPU 18*c* shown in FIG. 11. In that case, the external terminal device 6 may execute the same processes as the processes shown in FIG. 12, instead of the processes in steps S602 to S612 shown in FIG. 40.

The external terminal device 6 may execute the same processes as the processes shown in any one of FIGS. 20, 22, 24, 26, and 35, instead of the processes in steps S602 to S612 shown in FIG. 40.

The CPU 61 may be configured similarly to the CPU 18*d* shown in FIG. 28. In that case, the external terminal device 6 may execute the same processes as the processes shown in FIG. 29, instead of the processes in steps S602 to S612 shown in FIG. 40.

In the first to eighth embodiments, various forms capable of being applied to the endoscope device 1 can be similarly applied to the endoscope system 100 of the ninth embodiment.

The endoscope system 100 can simplify a user's designation of the reference point, and improve the reliability of the measurement result.

Addition

A measurement system according to one aspect of the present invention includes an image acquisition device and a measurement device. The image acquisition device acquires a first image of a subject. The first image acquired by the image acquisition device is input to the measurement device. The measurement device executes measurement of the subject using the first image. The measurement device includes a display control unit, an information reading unit, a reference designation point setting unit, a reference calculation unit, a measurement point setting unit, a measurement unit, and a reference point calculation unit. The display control unit causes a monitor to display at least one of the first image and a second image based on the first image. The information reading unit reads out measurement mode information indicating a measurement mode from a recording medium having the measurement mode information recorded therein. The reference designation point setting unit sets a plurality of reference designation points in one of the first image and the second image displayed on the monitor, on the basis of a first position designated by a user in one of the first image and the second image displayed on the monitor. The reference calculation unit calculates one of a reference line and a reference plane on the basis of the plurality of reference designation points. The reference line and the reference plane are used in the measurement mode indicated by the measurement mode information. The measurement point setting unit sets a measurement point in one of the first image and the second image displayed on the monitor, on the basis of a second position designated by the user in one of the first image and the second image displayed on the monitor. The measurement unit executes measurement of the subject on the basis of one of the reference line and the reference plane, the measurement point, and the measurement mode. The reference point calculation unit calculates a plurality of reference points leading to higher reliability of a measurement result instead of the plurality of reference designation points, on the basis of one of the first image and the second image in which the measurement point is set, the plurality of reference designation points, the measurement mode, and the measurement point. The reference calculation unit calculates one of a new reference line and a new reference plane on the basis of the plurality of reference points.

While preferred embodiments of the present invention have been described and shown above, it should be understood that these are exemplars of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A measurement device comprising:
   an image sensor configured to acquire a first image of a subject; and
   a controller configured to:
   display at least one of the first image and a second image based on the first image;
   read out measurement mode information indicating a measurement mode from a recording medium having the measurement mode information recorded therein;
   set a plurality of reference designation points in one of the displayed first image and the displayed second image on the basis of a first position designated by a user in one of the displayed first image and the displayed second image;
   calculate one of a reference line and a reference plane on the basis of the plurality of reference designation points, the reference line and the reference plane being used in the measurement mode indicated by the measurement mode information;
   set a measurement point in one of the displayed first image and the displayed second image, on the basis of a second position designated by the user in one of the displayed first image and the displayed second image;
   execute measurement of the subject;
   calculate a plurality of reference points leading to higher reliability of a measurement result instead of the plurality of reference designation points, on the basis of one of the first image and the second image in which the measurement point is set, the plurality of reference designation points, the measurement mode, and the measurement point,
   calculate one of a new reference line and a new reference plane on the basis of the plurality of reference points, and
   execute the measurement on the basis of one of the new reference line and the new reference plane, the measurement point, and the measurement mode.

2. The measurement device according to claim 1, wherein the controller is configured to calculate a portion of the plurality of reference points using a point, located at the same position as that of the reference designation point included in the plurality of reference designation points, as the reference point.

3. The measurement device according to claim 1, wherein the controller is configured to calculate the plurality of reference points such that distances between the plurality of reference points increase.

4. The measurement device according to claim 1,
   wherein the plurality of reference points are at least three reference points, and
   the controller is configured to calculate the at least three reference points such that an area of a polygon with vertices at the at least three reference points increases.

5. The measurement device according to claim 1, wherein the controller is configured to calculate the plurality of reference points such that one of a first intersection point and a second intersection point comes close to a centroid of the plurality of reference points, the first intersection point being an intersection point of a perpendicular line from the measurement point to the new reference line with the new reference line, and the second intersection point being an intersection point of a perpendicular line from the measurement point to the new reference plane with the new reference plane.

6. The measurement device according to claim 1, wherein the controller is configured to calculate the plurality of reference points such that a degree to which the new reference line approximates an end of the subject becomes higher.

7. The measurement device according to claim 1, wherein the controller is configured to calculate the plurality of reference points such that a degree to which the new reference plane approximates a surface of the subject becomes higher.

8. The measurement device according to claim 1, wherein the controller is configured to calculate at least one reference point included in the plurality of reference points such that distances between the plurality of reference points become larger than distances between the plurality of reference designation points.

9. The measurement device according to claim 1,
   wherein the plurality of reference designation points are at least three reference designation points,
   the plurality of reference points are at least three reference points,
   the controller is configured to calculate the at least three reference points such that a first area becomes larger than a second area,
   the first area is an area of a polygon with vertices at the at least three reference points, and
   the second area is an area of a polygon with vertices at the at least three reference designation points.

10. The measurement device according to claim 1,
    wherein the controller is configured to calculate the plurality of reference points such that a first distance becomes smaller than a second distance,
    the first distance is a distance between one of a first intersection point and a second intersection point and a centroid of the plurality of reference points, the first intersection point being an intersection point of a perpendicular line from the measurement point to the new reference line with the new reference line, and the second intersection point being an intersection point of a perpendicular line from the measurement point to the new reference plane with the new reference plane, and
    the second distance is a distance between one of a third intersection point and a fourth intersection point and a centroid of the plurality of reference designation points, the third intersection point being an intersection point of a perpendicular line from the measurement point to the reference line with the reference line, and the fourth intersection point being an intersection point of a perpendicular line from the measurement point to the reference plane with the reference plane.

11. The measurement device according to claim 1,
wherein the controller is configured to calculate the plurality of reference points such that a first degree becomes higher than a second degree,
the first degree is a degree to which one of the new reference line and the new reference plane determined on the basis of the plurality of reference points approximates a surface of the subject, and
the second degree is a degree to which one of the reference line and the reference plane determined on the basis of the plurality of reference designation points approximates the surface of the subject.

12. The measurement device according to claim 1, wherein the controller is configured to calculate at least one reference point included in the plurality of reference points such that a position of the at least one reference point satisfies a criterion according to characteristics of the measurement mode indicated by the measurement mode information.

13. The measurement device according to claim 12, wherein the controller is configured to:
set a plurality of temporary reference points in one of the displayed first image and the displayed second image,
select combinations, each including at least two temporary reference points included in the plurality of temporary reference points,
calculate an evaluation value indicating a degree to which the at least two temporary reference points included in the combination are suitable for the criterion, for each combination, and
in a case where a first degree indicated by the evaluation value of a first combination is higher than a second degree indicated by the evaluation value of a second combination, set at least one of the at least two temporary reference points included in the first combination as the reference point.

14. The measurement device according to claim 1, wherein the controller is configured to to display the plurality of reference points on at least one of the displayed first image and the displayed second image.

15. The measurement device according to claim 1, wherein the controller is configured to display one of the reference line and the reference plane determined on the basis of the plurality of reference points on at least one of the displayed first image and the displayed second image.

16. The measurement device according to claim 1, wherein the controller is configured to display the plurality of reference points and the plurality of reference designation points on at least one of the displayed first image and the displayed second image.

17. The measurement device according to claim 1, wherein the controller is configured to display the new reference line determined on the basis of the plurality of reference points and the reference line determined on the basis of the plurality of reference designation points on at least one of displayed the first image and the displayed second image.

18. The measurement device according to claim 1, wherein the controller is configured to display the new reference plane determined on the basis of the plurality of reference points and the reference plane determined on the basis of the plurality of reference designation points on at least one of the displayed first image and the displayed second image.

19. A method of operating a measurement device, the method comprising:
acquiring a first image of a subject;
displaying at least one of the first image and a second image based on the first image;
reading out measurement mode information indicating a measurement mode from a recording medium having the measurement mode information recorded therein;
setting a plurality of reference designation points in one of the displayed first image and the displayed second image, on the basis of a first position designated by a user in one of the displayed first image and the displayed second image;
calculating one of a reference line and a reference plane on the basis of the plurality of reference designation points, the reference line and the reference plane being used in the measurement mode indicated by the measurement mode information;
setting a measurement point in one of the displayed first image and the displayed second image, on the basis of a second position designated by the user in one of the displayed first image and the displayed second image;
calculating a plurality of reference points leading to higher reliability of a measurement result instead of the plurality of reference designation points, on the basis of one of the first image and the second image in which the measurement point is set, the plurality of reference designation points, the measurement mode, and the measurement point;
calculating one of a new reference line and a new reference plane on the basis of the plurality of reference points; and
executing measurement of the subject on the basis of one of the new reference line and the new reference plane, the measurement point, and the measurement mode.

20. A computer-readable non-transitory recording medium having a program recorded therein, the program causing a computer to:
acquire a first image of a subject;
display at least one of the first image and a second image based on the first image;
read out measurement mode information indicating a measurement mode from a recording medium having the measurement mode information recorded therein;
set a plurality of reference designation points in one of the displayed first image and the displayed second image, on the basis of a first position designated by a user in one of the displayed first image and the displayed second image;
calculate one of a reference line and a reference plane on the basis of the plurality of reference designation points, the reference line and the reference plane being used in the measurement mode indicated by the measurement mode information;
set a measurement point in one of the displayed first image and the displayed second image, on the basis of a second position designated by the user in one of the displayed first image and the displayed second image;
calculate a plurality of reference points leading to higher reliability of a measurement result instead of the plurality of reference designation points, on the basis of one of the first image and the second image in which the measurement point is set, the plurality of reference designation points, the measurement mode, and the measurement point;

calculate one of a new reference line and a new reference plane on the basis of the plurality of reference points; and execute measurement of the subject on the basis of one of the new reference line and the new reference plane, the measurement point, and the measurement mode.

* * * * *